(12) United States Patent
Coburn et al.

(10) Patent No.: US 9,504,690 B2
(45) Date of Patent: Nov. 29, 2016

(54) TETRACYCLIC XANTHENE DERIVATIVES AND METHODS OF USE THEREOF FOR THE TREATMENT OF VIRAL DISEASES

(75) Inventors: Craig A. Coburn, Royersford, PA (US); Stuart B. Rosenblum, West Orange, PA (US); Joseph A. Kozlowski, Princeton, NJ (US); Richard Soll, San Diego, CA (US); Hao Wu, Shanghai (CN); Bin Hu, Shanghai (CN); Bin Zhong, Shanghai (CN); Dahai Wang, Shanghai (CN); Changmao Shen, Shanghai (CN); Fei Sun, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 99 days.

(21) Appl. No.: 14/005,430

(22) PCT Filed: Mar. 16, 2012

(86) PCT No.: PCT/US2012/029446
§ 371 (c)(1),
(2), (4) Date: Mar. 21, 2014

(87) PCT Pub. No.: WO2012/125926
PCT Pub. Date: Sep. 20, 2012

(65) Prior Publication Data
US 2014/0199264 A1   Jul. 17, 2014

(30) Foreign Application Priority Data
Mar. 17, 2011  (WO) ............... PCT/CN2011/071897

(51) Int. Cl.
| A61K 31/535 | (2006.01) |
| A61K 31/5383 | (2006.01) |
| C07D 491/06 | (2006.01) |
| C07D 498/06 | (2006.01) |
| A61K 31/4178 | (2006.01) |
| A61K 45/06 | (2006.01) |
| C07D 493/06 | (2006.01) |

(52) U.S. Cl.
CPC ....... *A61K 31/5383* (2013.01); *A61K 31/4178* (2013.01); *A61K 45/06* (2013.01); *C07D 491/06* (2013.01); *C07D 493/06* (2013.01); *C07D 498/06* (2013.01)

(58) Field of Classification Search
CPC .............. A61K 31/4178; A61K 31/5383; A61K 45/06; C07D 498/06; C07D 491/06; C07D 493/06
USPC ............. 514/229, 397; 544/99; 548/311.7
See application file for complete search history.

(56) References Cited

U.S. PATENT DOCUMENTS

| 7,153,848 B2 | 12/2006 | Hudyma et al. |
| 7,662,809 B2 | 2/2010 | Ercolani et al. |
| 7,973,040 B2 | 7/2011 | Harper et al. |
| 8,080,654 B2 | 12/2011 | Harper et al. |

(Continued)

FOREIGN PATENT DOCUMENTS

| CN | 101336248 A | 12/2008 |
| CN | WO 2012003642 A1 * | 1/2012 ......... A61K 31/4178 |

(Continued)

OTHER PUBLICATIONS

Wilson, et al., "Tunable DNA Photocleavage by an Acridine-Imidazole Conjugate", Inorganic Chemistry, 2005, vol. 44, No. 18, pp. 6159-6173.

(Continued)

*Primary Examiner* — My-Chau T Tran
(74) *Attorney, Agent, or Firm* — Jeffrey P. Bergman; Catherine D. Fitch

(57) ABSTRACT

The present invention relates to novel Tetracyclic Xanthene Derivatives of Formula (I) and pharmaceutically acceptable salts thereof, wherein A, $Y^1$, $Y^2$, Z, $R^a$, $R^b$, $R^{1a}$, $R^{1b}$ and $R^2$ are as defined herein. The present invention also relates to compositions comprising at least one Tetracyclic Xanthene Derivative, and methods of using the Tetracyclic Xanthene Derivatives for treating or preventing HCV infection in a patient.

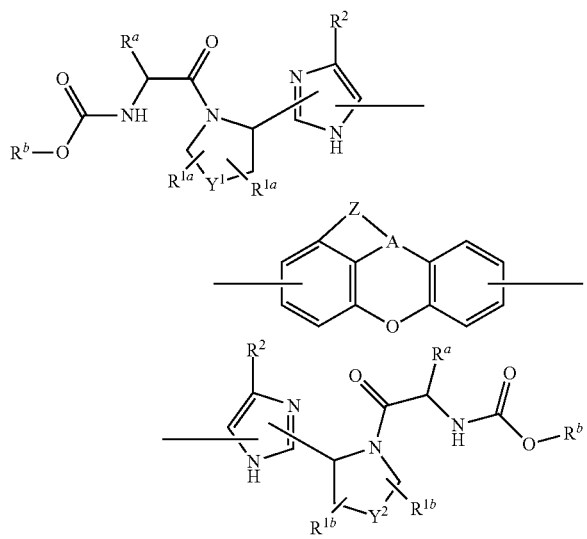

14 Claims, No Drawings

(56) References Cited

U.S. PATENT DOCUMENTS

| | | |
|---|---|---|
| 8,377,980 B2 | 2/2013 | Belema et al. |
| 2006/0019974 A1 | 1/2006 | Mederski et al. |
| 2006/0258682 A1 | 11/2006 | Liao et al. |
| 2007/0049593 A1 | 3/2007 | Oka et al. |
| 2007/0110708 A1 | 5/2007 | Miller et al. |
| 2007/0185175 A1 | 8/2007 | Liu et al. |
| 2008/0299075 A1 | 12/2008 | Bachand et al. |
| 2009/0004111 A1 | 1/2009 | Rice et al. |
| 2009/0042860 A1 | 2/2009 | Bergstrom et al. |
| 2010/0310512 A1 | 12/2010 | Guo et al. |
| 2010/0316607 A1 | 12/2010 | Or et al. |
| 2011/0104109 A1 | 5/2011 | Bennettm et al. |
| 2011/0130361 A1 | 6/2011 | Grimm et al. |
| 2011/0223134 A1 | 9/2011 | Nair et al. |
| 2011/0224211 A1 | 9/2011 | Schmitz et al. |
| 2012/0040962 A1 | 2/2012 | Li et al. |
| 2012/0083483 A1 | 4/2012 | Coburn et al. |
| 2013/0156731 A1 | 6/2013 | Chen et al. |
| 2013/0164258 A1 | 6/2013 | Chen et al. |
| 2013/0280214 A1 | 10/2013 | Vacca et al. |
| 2014/0170111 A1 | 6/2014 | Coburn et al. |
| 2014/0199264 A1 | 7/2014 | Coburn et al. |
| 2014/0377223 A1 | 12/2014 | Kozlowski et al. |

FOREIGN PATENT DOCUMENTS

| | | |
|---|---|---|
| EP | 1719773 A1 | 11/2006 |
| JP | 10101591 A1 | 4/1984 |
| WO | 2007009120 A2 | 1/2007 |
| WO | 2007084413 A2 | 7/2007 |
| WO | 2009023179 A2 | 2/2009 |
| WO | 2009102325 A1 | 8/2009 |
| WO | 2010041687 A1 | 4/2010 |
| WO | 2010065674 A1 | 6/2010 |
| WO | 2012040923 A1 | 4/2012 |
| WO | 2012050850 A1 | 4/2012 |
| WO | 20120401014 A1 | 4/2012 |

OTHER PUBLICATIONS

Marsilje, T.H., et al., "Optimization of small molecule agonists of the thrombopoietin (Tpo) receptor derived from a benzo[a]carbazole hit scaffold", Bioorganic and Medicinal Chem. Lett., 2008, vol. 18,pp. 5255-5258.

CAR RN 1025830-17-4, STN Entry, Jun. 5, 2008.

CAPLUS Accession No. 1980:471599.

CAPLUS Accession No. 2009:295362 (JP2009-054809).

Alper, P.B., et al., "Discovery and biological evaluation of benzo[a]carbazole-based small molecule agonists of the thrombopoietin (Tpo) receptor", Bioorganic and Medicinal Chem. Lett., 2008, vol. 18, pp. 5255-5258.

CN1474815—English Abstract—Corresponding to US Application No. US2006/0019974 cited herein.

* cited by examiner

TETRACYCLIC XANTHENE DERIVATIVES AND METHODS OF USE THEREOF FOR THE TREATMENT OF VIRAL DISEASES

CROSS-REFERENCE TO RELATED APPLICATIONS

This application is the national stage application under 35 U.S.C. 371 of International Patent Application No. PCT/US12/029446, filed Mar. 16, 2012, which claims priority to International Patent Application No. PCT/CN11/071879, filed Mar. 17, 2011. Each of the aforementioned PCT applications is incorporated by reference in its entirety.

REFERENCE TO SEQUENCE LISTING SUBMITTED ELECTRONICALLY

The sequence listing of the present application is being submitted electronically via EFS-Web as an ASCII formatted sequence listing with a file name "23041_Seq.txt", creation date of Sep. 5, 2013 and a size of 1 KB. This sequence listing submitted via EFS-Web is part of the specification and is herein incorporated by reference in its entirety.

FIELD OF THE INVENTION

The present invention relates to novel Tetracyclic Xanthene Derivatives, compositions comprising at least one Tetracyclic Xanthene Derivative, and methods of using the Tetracyclic Xanthene Derivatives for treating or preventing HCV infection in a patient.

BACKGROUND OF THE INVENTION

Hepatitis C virus (HCV) is a major human pathogen. A substantial fraction of these HCV-infected individuals develop serious progressive liver disease, including cirrhosis and hepatocellular carcinoma, which are often fatal. HCV is a (+)-sense single-stranded enveloped RNA virus that has been implicated as the major causative agent in non-A, non-B hepatitis (NANBH), particularly in blood-associated NANBH (BB-NANBH) (see, International Publication No. WO 89/04669 and European Patent Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliary cirrhosis.

It is well-established that persistent infection of HCV is related to chronic hepatitis, and as such, inhibition of HCV replication is a viable strategy for the prevention of hepatocellular carcinoma. Current therapies for HCV infection include α-interferon monotherapy and combination therapy comprising α-interferon and ribavirin. These therapies have been shown to be effective in some patients with chronic HCV infection, but suffer from poor efficacy and unfavorable side-effects and there are currently efforts directed to the discovery of HCV replication inhibitors that are useful for the treatment and prevention of HCV related disorders.

Current research efforts directed toward the treatment of HCV includes the use of antisense oligonucleotides, free bile acids (such as ursodeoxycholic acid and chenodeoxycholic acid) and conjugated bile acids (such as tauroursodeoxycholic acid). Phosphonoformic acid esters have also been proposed as potentially useful for the treatment of various viral infections, including HCV. Vaccine development, however, has been hampered by the high degree of viral strain heterogeneity and immune evasion and the lack of protection against reinfection, even with the same inoculum.

In light of these treatment hurdles, the development of small-molecule inhibitors directed against specific viral targets has become a major focus of anti-HCV research. The determination of crystal structures for NS3 protease, NS3 RNA helicase, NS5A, and NS5B polymerase, with and without bound ligands, has provided important structural insights useful for the rational design of specific inhibitors.

Recent attention has been focused toward the identification of inhibitors of HCV NS5A. HCV NS5A is a 447 amino acid phosphoprotein which lacks a defined enzymatic function. It runs as 56 kd and 58 kd bands on gels depending on phosphorylation state (Tanji, et al. *J. Virol.* 69:3980-3986 (1995)). HCV NS5A resides in replication complex and may be responsible for the switch from replication of RNA to production of infectious virus (Huang, Y, et al., *Virology* 364:1-9 (2007)).

Multicyclic HCV NS5A inhibitors have been reported. See U.S. Patent Publication Nos. US20080311075, US20080044379, US20080050336, US20080044380, US20090202483 and US2009020478. HCV NS5A inhibitors having fused tricyclic moieties are disclosed in International Patent Publication Nos. WO 10/065681, WO 10/065668, and WO 10/065674.

Other HCV NS5A inhibitors and their use for reducing viral load in HCV infected humans have been described in U.S. Patent Publication No. US20060276511.

SUMMARY OF THE INVENTION

In one aspect, the present invention provides Compounds of Formula (I):

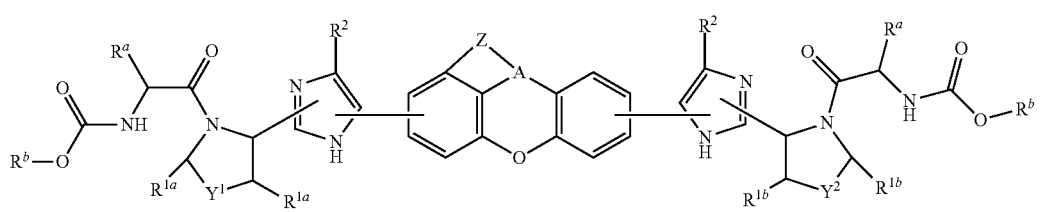

and pharmaceutically acceptable salts thereof,
wherein:

A is N or CH;

each of $Y^1$ and $Y^2$ is independently $—[C(R^1)_2]_w—$ or $—Si(R^b)_2$;

Z is $—C(R^a)=C(R^a)—$, $—[C(R^a)_2]_t—$, $—O—C(R^a)=$, $—N(R^a)—C(R^a)=$, $—C(R^a)=N—$, $—O—[C(R^a)_2]_w—$ or

—N($R^a$)—C($R^a$)$_2$—C($R^a$)$_2$—, such that when Z is —O—C($R^a$)= or —N($R^a$)—C($R^a$)=, then A is carbon;

each occurrence of $R^a$ is independently H, $C_1$-$C_6$ alkyl, $C_3$-$C_7$ cycloalkyl, $C_6$-$C_{10}$ aryl, 4- to 7-membered heterocycloalkyl or 5- to 6-membered heteroaryl;

each occurrence of $R^b$ is independently $C_1$-$C_6$ alkyl, $C_3$-$C_7$ cycloalkyl, 4- to 7-membered heterocycloalkyl or 5- to 6-membered heteroaryl;

each occurrence of $R^1$ is independently H, $C_1$-$C_6$ alkyl, halo, $C_1$-$C_6$ haloalkyl, —O—$C_1$-$C_6$ alkyl or —CN, or two $R^1$ groups that are attached to the same carbon atom, together with the common carbon atom to which they are attached, can join to form a spirocyclic $C_3$-$C_6$ cycloalkyl group or a spirocyclic 4- to 7-membered heterocycloalkyl group;

each occurrence of $R^{1a}$ is independently H, $C_1$-$C_6$ alkyl, CN, halo, $C_1$-$C_6$ haloalkyl, —OH, —O—($C_1$-$C_6$ alkyl), —O—($C_1$-$C_6$ haloalkyl), or two $R^{1a}$ groups, together with the carbon atoms to which they are attached, join to form a $C_3$-$C_6$ cycloalkyl group or a 4- to 7-membered heterocycloalkyl group, or when Y is carbon, one $R^{1a}$ group and $Y^1$, together with the carbon atoms to which they are attached, join to form a $C_3$-$C_6$ cycloalkyl group or a 4- to 7-membered heterocycloalkyl group;

each occurrence of $R^{1b}$ is independently H, $C_1$-$C_6$ alkyl, CN, halo, $C_1$-$C_6$ haloalkyl, —OH, —O—($C_1$-$C_6$ alkyl), —O—($C_1$-$C_6$ haloalkyl), or two $R^{1b}$ groups, together with the carbon atoms to which they are attached, join to form a $C_3$-$C_6$ cycloalkyl group or a 4- to 7-membered heterocycloalkyl group, or when $Y^2$ is carbon, one $R^{1b}$ group and $Y^2$, together with the carbon atoms to which they are attached, join to form a $C_3$-$C_6$ cycloalkyl group or a 4- to 7-membered heterocycloalkyl group;

each occurrence of $R^2$ is independently H, halo, or alkyl;

t is 1, 2 or 3; and each occurrence of w is independently 1 or 2.

The Compounds of Formula (I) (also referred to herein as the "Tetracyclic Xanthene Derivatives") and pharmaceutically acceptable salts thereof can be useful, for example, for inhibiting HCV viral replication or replicon activity, and for treating or preventing HCV infection in a patient. Without being bound by any specific theory, it is believed that the Tetracyclic Xanthene Derivatives inhibit HCV viral replication by inhibiting HCV NS5A.

Accordingly, the present invention provides methods for treating or preventing HCV infection in a patient, comprising administering to the patient an effective amount of at least one Tetracyclic Xanthene Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Tetracyclic Xanthene Derivatives, compositions comprising at least one Tetracyclic Xanthene Derivative, and methods of using the Tetracyclic Xanthene Derivatives for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refer's to an amount of Tetracyclic Xanthene Derivative and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood or severity of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl)$_n$, or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-cycloalkyl, —C(O)OH and —C(O)O alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

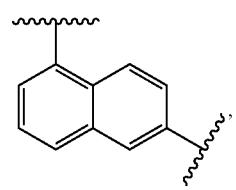 [SMILES: *c1ccc2c(*)cccc2c1]

is understood to represent both:

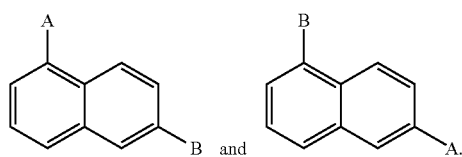

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

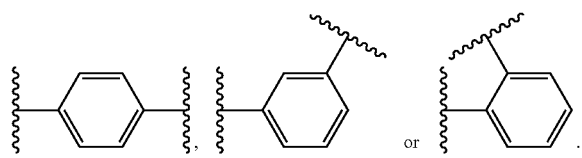

Unless otherwise indicated, an arylene group is unsubstituted.

The term "cycloalkyl," as used herein, refers to a non-aromatic mono- or multicyclic ring system comprising from 3 to about 10 ring carbon atoms. In one embodiment, a cycloalkyl contains from about 5 to about 10 ring carbon atoms. In another embodiment, a cycloalkyl contains from 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

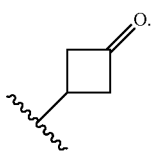 [SMILES: *C1CC(=O)C1]

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

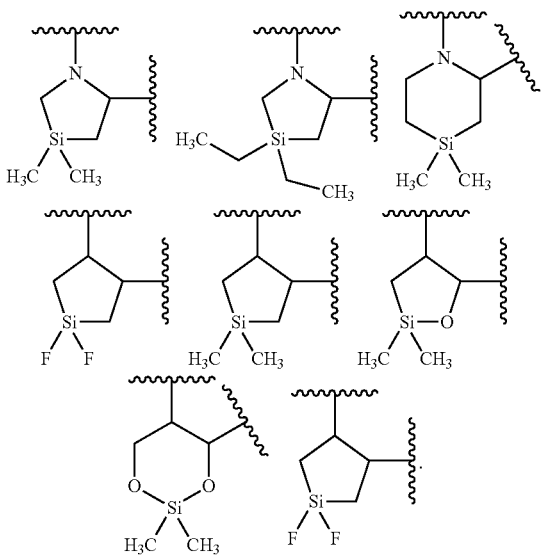

A ring carbon atom of a heterocycloalkyl group may be functionalized as a carbonyl group. An illustrative example of such a heterocycloalkyl group is:

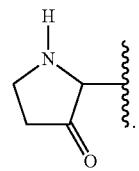

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, -Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

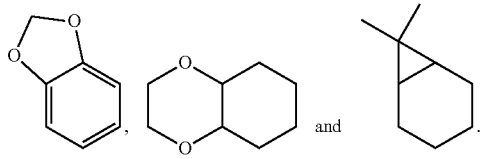

The term "silylalkyl," as used herein, refers to an alkyl group as defined above, wherein one or more of the alkyl group's hydrogen atoms has been replaced with a —Si(R$^x$)$_3$ group, wherein each occurrence of R$^x$ is independently C$_1$-C$_6$ alkyl, phenyl or a 3 to 6-membered cycloalkyl group. In one embodiment, a silylalkyl group has from 1 to 6 carbon atoms. In another embodiment, a silyl alkyl group contains a —Si(CH$_3$)$_3$ moiety. Non-limiting examples of silylalkyl groups include —CH$_2$—Si(CH$_3$)$_3$ and —CH$_2$CH$_2$—Si(CH$_3$)$_3$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, R$^6$, R$^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Tetracyclic Xanthene Derivative or a pharmaceutically acceptable salt of the compound. The transformation may occur by various mechanisms (e.g., by metabolic or chemical processes), such as, for example, through hydrolysis in blood.

For example, if a Tetracyclic Xanthene Derivative or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as (3-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a Tetracyclic Xanthene Derivative contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxyearbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a Tetracyclic Xanthene Derivative incorporates an amine functional group, a, prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)OY$^1$ wherein Y$^1$ is H, ($C_1$-$C_6$) alkyl or benzyl, —C(OY$^2$)Y$^3$ wherein Y$^2$ is ($C_1$-$C_4$) alkyl and Y$^3$ is ($C_1$-$C_6$)alkyl; carboxy ($C_1$-$C_6$)alkyl; amino($C_1$-$C_4$)alkyl or mono-N- or di-N,N—($C_1$-$C_6$)alkylaminoalkyl; —C(Y$^+$)Y$^5$ wherein Y$^+$ is H or methyl and Y$^5$ is mono-N- or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Tetracyclic Xanthene Derivatives can form salts which are also within the scope of this invention. Reference to a Tetracyclic Xanthene Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tetracyclic Xanthene Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Tetracyclic Xanthene Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Tetracyclic Xanthene Derivatives may be atropisomers (e.g., substituted biaryls) and are considered as part of this invention. Enantiomers can also be directly separated using chiral chromatographic techniques.

It is also possible that the Tetracyclic Xanthene Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Tetracyclic Xanthene Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Tetracyclic Xanthene Derivatives, and of the salts, solvates, hydrates, esters and prodrugs of the Tetracyclic Xanthene Derivatives, are intended to be included in the present invention.

The following abbreviations are used below and have the following meanings: AcOH or HOAc is acetic acid; $BH_3 \cdot SMe_2$ is borane-methyl sulfide complex; BOC or Boc is tert-butyloxycarbonyl; Bop reagent is [benzotriazol-1-yl-oxy-tris-(dimethylamino)phosphonium hexa-fluorophosphate]; DCM is dichloromethane; DIPEA or i-PrNEt$_2$ is diisopropylethylamine; DMF is N,N-dimethylformamide; dppf is diphenylphosphinoferrocene; DMSO is dimethylsulfoxide; esi is electron-spray ionization; EtOH is ethanol; EtOAc is ethyl acetate; TEA is triethylamine; HATU is O-(7-azabenzotriazol-1-yl)-N,N,N',N'-tetramethyluronium hexafluorophosphate; HPLC is high performance liquid chromatography; HRMS is high resolution mass spectrometry; KOAc is potassium acetate; LCMS is liquid chromatography/mass spectrometry; LDA is lithium diisopropylamide; MeI is iodomethane; MeOH is methanol; NBS is N-bromosuccinimide; NH$_4$OAc is ammonium acetate; Pd(OAc)$_2$ is palladium acetate; pinacol$_2$B$_2$ is bis(pinacolato)diboron; PPA is polyphosphoric acid; RPLC is reverse-phase liquid chromatography; THF is tetrahydrofuran; TLC is thin-layer chromatography; and Xantphos is (4,5-bis(diphenylphosphino)-9,9-dimethyl-xanthene).

The Compounds of Formula (I)

The present invention provides Tetracyclic Xanthene Derivatives of Formula (I):

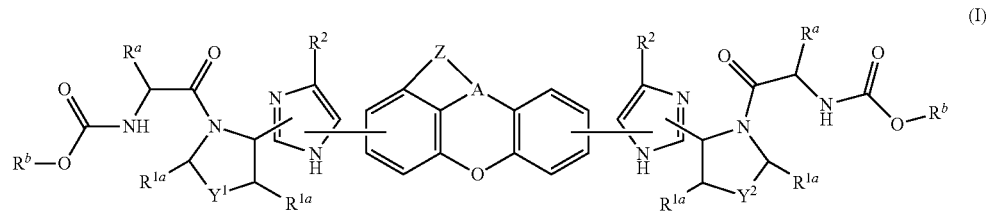

(I)

and pharmaceutically acceptable salts thereof, wherein A, $Y^1$, $Y^2$, Z, $R^a$, $R^b$, $R^{1a}$, $R^{1b}$ and $R^2$ are defined above for the Compounds of Formula (I).

In one embodiment, A is C.

In another embodiment, A is N.

In one embodiment, each of $Y^1$ and $Y^2$ is —[C(R$^1$)$_2$]$_w$—.
In one embodiment, each of $Y^1$ and $Y^2$ is —CH$_2$—, —CF$_2$— or —CHF—.
In another embodiment, each of $Y^1$ and $Y^2$ is —CH$_2$—.
In another embodiment, each of $Y^1$ and $Y^2$ is —CF$_2$—.
In still another embodiment, each of $Y^1$ and $Y^2$ is —CHF—.
In one embodiment, each of $Y^1$ and $Y^2$ is —Si(R$^b$)$_2$—.
In one embodiment, one of $Y^1$ and $Y^2$ is —[C(R$^1$)$_2$]$_w$— and the other is —Si(R$^b$)$_2$—.
In another embodiment, one of $Y^1$ and $Y^2$ is —CH$_2$— and the other is —Si(R$^b$)$_2$—.
In another embodiment, one of $Y^1$ and $Y^2$ is —CF$_2$— and the other is —Si(R$^b$)$_2$—.
In still another embodiment, one of $Y^1$ and $Y^2$ is —CHF— and the other is —Si(CH$_3$)$_2$—.
In one embodiment, Z is —OCH$_2$—, —OCH$_2$CH$_2$—, —O—CH═, —CH$_2$CH$_2$—, —CH$_2$CH$_2$CH$_2$—, —CH═CH— or —CH═N—.

In another embodiment, Z is —OCH$_2$—.
In another embodiment, Z is —OCH$_2$CH$_2$—.
In still another embodiment, Z is —O—CH═.
In another embodiment, Z is —CH$_2$CH$_2$—.
In yet another embodiment, Z is —CH$_2$CH$_2$CH$_2$—.
In another embodiment, Z is —CH═CH—.
In a further embodiment, Z is —CH═N—.
In one embodiment, each occurrence of $R^a$ is independently $C_1$-$C_6$ alkyl or $C_3$-$C_7$ cycloalkyl.
In another embodiment, each occurrence of $R^a$ is independently $C_1$-$C_6$ alkyl.
In another embodiment, each occurrence of $R^8$ is independently isopropyl, t-butyl or cyclopropyl.
In still another embodiment, each occurrence of $R^a$ is isopropyl.
In one embodiment, each occurrence of $R^b$ is $C_1$-$C_6$ alkyl.
In another embodiment, each occurrence of $R^b$ is methyl.
In one embodiment, each occurrence of $R^{1a}$ is H.
In another embodiment, each occurrence of $R^{1b}$ is H.
In another embodiment, each occurrence of $R^{1a}$ and $R^{1b}$ is H.
In one embodiment, each occurrence of $R^2$ is H.
In another embodiment, each occurrence of $R^a$ is independently $C_1$-$C_6$ alkyl or $C_3$-$C_7$ cycloalkyl and each occurrence of $R^a$ is independently $C_1$-$C_6$ alkyl.
In another embodiment, each occurrence of $R^8$ is isopropyl and each occurrence of $R^a$ is methyl.
In one embodiment, A is N Z is —CH$_2$CH$_2$— or —CH═CH—.
In another embodiment, each of $Y^1$ and $Y^2$ is independently —CH$_2$—, —CF$_2$— or —CHF—; each occurrence of $R^a$ is independently $C_1$-$C_6$ alkyl or $C_3$-$C_7$ cycloalkyl; and each occurrence of $R^b$ is independently $C_1$-$C_6$ alkyl.

In another embodiment, each of $Y^1$ and $Y^2$ is —CH$_2$—; each occurrence of $R^8$ is independently $C_1$-$C_6$ alkyl or $C_3$-$C_7$ cycloalkyl; and each occurrence of $R^b$ is independently $C_1$-$C_6$ alkyl.
In another embodiment, each of $Y^1$ and $Y^2$ is —CF$_2$—; each occurrence of $R^a$ is independently $C_1$-$C_6$ alkyl or $C_3$-$C_7$ cycloalkyl; and each occurrence of $R^b$ is independently $C_1$-$C_6$ alkyl.
In still another embodiment, each of $Y^1$ and $Y^2$ is —CHF— each occurrence of $R^a$ is independently $C_1$-$C_6$ alkyl or $C_3$-$C_7$ cycloalkyl; and each occurrence of $R^b$ is independently $C_1$-$C_6$ alkyl.
In another embodiment, each of $Y^1$ and $Y^2$ is —CH$_2$—; each occurrence of $R^8$ is isopropyl; and each occurrence of $R^b$ is methyl.
In another embodiment, each of $Y^1$ and $Y^2$ is —CF$_2$—; each occurrence of $R^a$ is isopropyl; and each occurrence of $R^b$ is methyl.
In one embodiment, the Compounds of Formula (I) have the formula (Ia):

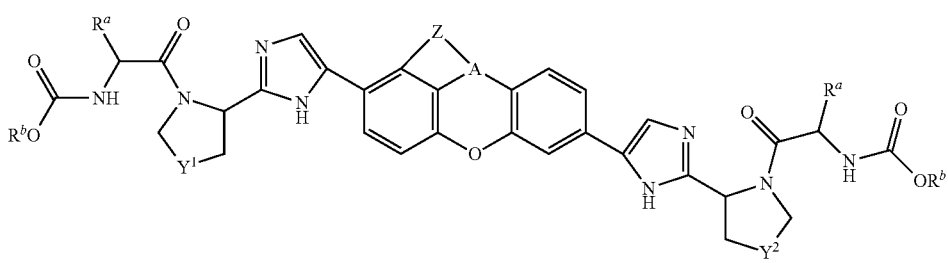

(Ia)

and pharmaceutically acceptable salts thereof,
wherein:
A is N or CH;
each of $Y^1$ and $Y^2$ is independently —CH$_2$—, —CF$_2$— or —CHF—;
Z is —OCH$_2$—, —OCH$_2$CH$_2$—, —O—CH═, —CH$_2$CH$_2$—, —CH$_2$CH$_2$CH$_2$—, —CH═CH— or —CH═N—, such that when Z is —O—CH═, then A is carbon;
each occurrence of $R^a$ is independently $C_1$-$C_6$ alkyl, $C_6$-$C_{10}$ aryl or $C_3$-$C_7$ cycloalkyl; and
each occurrence of $R^b$ is independently $C_1$-$C_6$ alkyl.
In one embodiment, for the Compounds of Formula (Ia), A is C.
In another embodiment, for the Compounds of Formula (Ia), A is N.
In one embodiment, for the Compounds of Formula (Ia), each of $Y^1$ and $Y^2$ is —CH$_2$—.
In another embodiment, for the Compounds of Formula (Ia), each of $Y^1$ and $Y^2$ is —CF$_2$—.
In another embodiment, for the Compounds of Formula (Ia), each of $Y^1$ and $Y^2$ is —CHF—.
In one embodiment, for the Compounds of Formula (Ia), one of $Y^1$ and $Y^2$ is —CH$_2$— and the other is —CF$_2$—.
In another embodiment, for the Compounds of Formula (Ia), one of $Y^1$ and $Y^2$ is —CH$_2$— and the other is —CHF—.
In another embodiment, for the Compounds of Formula (Ia), one of $Y^1$ and $Y^2$ is —CHF— and the other is —CF$_2$—.
In one embodiment, for the Compounds of Formula (Ia), Z is —OCH$_2$—.
In another embodiment, for the Compounds of Formula (Ia), Z is —OCH$_2$CH$_2$—.
In another embodiment, for the Compounds of Formula (Ia), Z is —O—CH═.

In still another embodiment, for the Compounds of Formula (Ia), Z is —CH$_2$CH$_2$—.

In another embodiment, for the Compounds of Formula (Ia), Z is —CH$_2$CH$_2$CH$_2$—.

In yet another embodiment, for the Compounds of Formula (Ia), Z is —CH=CH—.

In a further embodiment, for the Compounds of Formula (Ia), Z is —CH=N—.

In one embodiment, for the Compounds of Formula (Ia), each occurrence of R$^a$ is independently isopropyl, t-butyl or cyclopropyl.

In still another embodiment, for the Compounds of Formula (Ia), each occurrence of R$^a$ is isopropyl.

In one embodiment, for the Compounds of Formula (Ia), each occurrence of R$^b$ is methyl.

In another embodiment, for the Compounds of Formula (Ia), each occurrence of R$^a$ is isopropyl and each occurrence of R$^b$ is methyl.

In one embodiment, for the Compounds of Formula (Ia),
A is N or CH;
each of Y$^1$ and Y$^2$ is independently —CH$_2$—, —CF$_2$— or —CHF—;
Z is —OCH$_2$—, —OCH$_2$CH$_2$—, —O—CH=, —CH$_2$CH$_2$—, —CH$_2$CH$_2$CH$_2$—, —CH=CH— or —CH=N—, such that when Z is —O—CH=, then A is carbon;
each occurrence of R$^a$ is independently isopropyl, t-butyl or cyclopropyl; and
each occurrence of R$^b$ is independently methyl.

In another embodiment, for the Compounds of Formula (Ia),
A is N;
each of Y$^1$ and Y$^2$ is independently —CH$_2$—, —CF$_2$— or —CHF—;
Z is —CH$_2$CH$_2$— or —CH=CH—;
each occurrence of R$^a$ is independently isopropyl; and
each occurrence of R$^b$ is independently methyl.

In another embodiment, for the Compounds of Formula (Ia),
A is N;
each of Y$^1$ and Y$^2$ is independently —CH$_2$—;
Z is —CH$_2$CH$_2$— or —CH=CH—;
each occurrence of R$^a$ is independently isopropyl; and
each occurrence of R$^b$ is independently methyl.

In one embodiment, the Compounds of Formula (I) have the formula (Ib):

(Ib)

and pharmaceutically acceptable salts thereof, wherein:
A is N or CH;
each of Y$^1$ and Y$^2$ is independently —CH$_2$—, —CF$_2$— or —CHF—;
Z is —OCH$_2$—, —OCH$_2$CH$_2$—, —CH$_2$CH$_2$—, —CH$_2$CH$_2$CH$_2$—, —CH=CH— or —CH=N—, such that when Z is —O—CH=, then A is carbon;

each occurrence of R$^b$ is independently C$_1$-C$_6$ alkyl, C$_6$-C$_{10}$ aryl or C$_3$-C$_7$ cycloalkyl; and
each occurrence of R$^b$ is independently C$_1$-C$_6$ alkyl.

In one embodiment, for the Compounds of Formula (Ib), A is C.

In another embodiment, for the Compounds of Formula (Ib), A is N.

In one embodiment, for the Compounds of Formula (Ib), each of Y$^1$ and Y$^2$ is —CH$_2$—.

In another embodiment, for the Compounds of Formula (Ib), each of Y$^1$ and Y$^2$ is —CF$_2$—.

In another embodiment, for the Compounds of Formula (Ib), each of Y$^1$ and Y$^2$ is —CHF—.

In one embodiment, for the Compounds of Formula (Ib), one of Y$^1$ and Y$^2$ is —CH$_2$— and the other is —CF$_2$—.

In another embodiment, for the Compounds of Formula (Ib), one of Y$^1$ and Y$^2$ is CH$_2$— and the other is —CHF—.

In another embodiment, for the Compounds of Formula (Ib), one of Y$^1$ and Y$^2$ is —CHF— and the other is —CF$_2$—.

In one embodiment, for the Compounds of Formula (Ib), Z is —OCH$_2$—.

In another embodiment, for the Compounds of Formula (Ib), Z is —OCH$_2$CH$_2$—.

In another embodiment, for the Compounds of Formula (Ib), Z is —O—CH=.

In still another embodiment, for the Compounds of Formula (Ib), Z is —CH$_2$CH$_2$—.

In another embodiment, for the Compounds of Formula (Ib), Z is —CH$_2$CH$_2$CH$_2$—.

In yet another embodiment, for the Compounds of Formula (Ib), Z is —CH=CH—.

In a further embodiment, for the Compounds of Formula (Ib), Z is —CH=N—.

In one embodiment, for the Compounds of Formula (Ib), each occurrence of R$^a$ is independently isopropyl, t-butyl or cyclopropyl.

In still another embodiment, for the Compounds of Formula (Ib), each occurrence of R$^a$ is isopropyl.

In one embodiment, for the Compounds of Formula (Ib), each occurrence of R$^b$ is methyl.

In another embodiment, for the Compounds of Formula (Ib), each occurrence of R$^a$ is isopropyl and each occurrence of R$^b$ is methyl.

In one embodiment, for the Compounds of Formula (Ib), A is N or CH;
each of Y$^1$ and Y$^2$ is independently —CH$_2$—, —CF$_2$— or —CHF—;
Z is —OCH$_2$—, —OCH$_2$CH$_2$—, —O—CH=, —CH$_2$CH$_2$—, —CH$_2$CH$_2$CH$_2$—, —CH=CH— or —CH=N—, such that when Z is —O—CH=, then A is carbon;
each occurrence of R$^a$ is independently isopropyl, t-butyl or cyclopropyl; and
each occurrence of R$^b$ is independently methyl.

In another embodiment, for the Compounds of Formula (Ib),

A is N;
each of $Y^1$ and $Y^2$ is independently —$CH_2$—, —$CF_2$— or —CHF—;
Z is —$CH_2CH_2$— or —CH=CH—;
each occurrence of $R^a$ is independently isopropyl; and
each occurrence of $R^b$ is independently methyl.

In another embodiment, for the Compounds of Formula (Ib),

A is N;
each of $Y^1$ and $Y^2$ is independently —$CH_2$—;
Z is —$CH_2CH_2$— or —CH=CH—;
each occurrence of $R^a$ is independently isopropyl; and
each occurrence of $R^b$ is independently methyl.

In one embodiment, variables A, $Y^1$, $Y^2$, Z, $R^a$, $R^b$, $R^{1a}$, $R^{1b}$ and $R^2$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-20 as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A-G below. Alternative synthetic pathways and analogous structures will be apparent to those skilled in the art of organic synthesis.

Scheme A shows methods useful for making the tetracyclic compounds of formula A9, which are useful intermediates for making the Compounds of Formula (I), wherein A is nitrogen and Z is —CH=CH—.

Scheme A

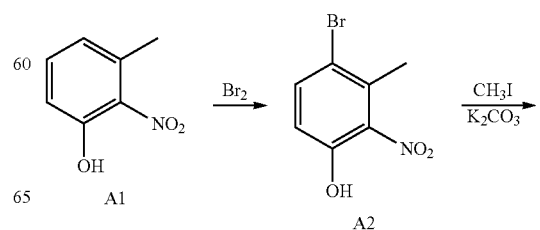

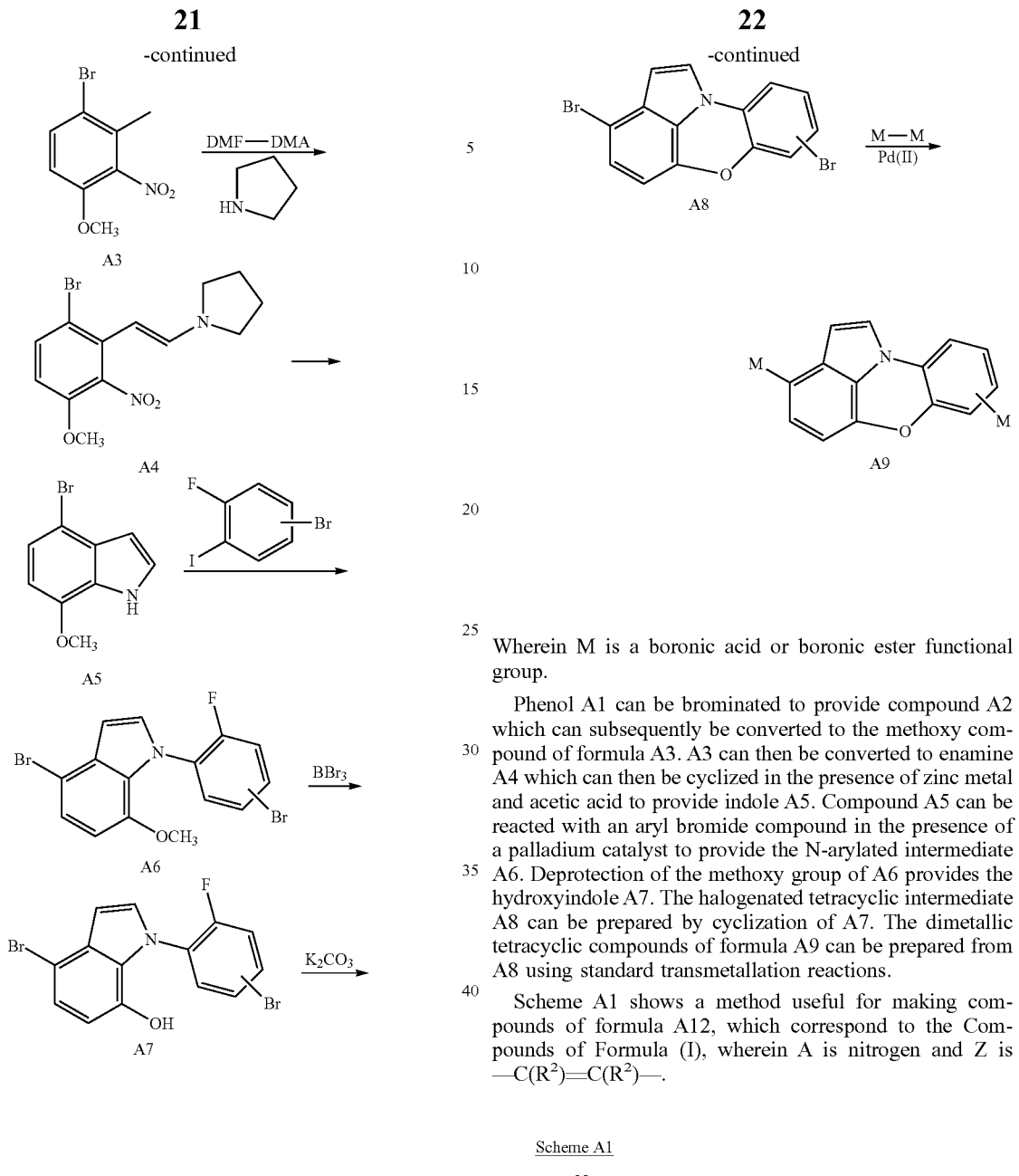

Wherein M is a boronic acid or boronic ester functional group.

Phenol A1 can be brominated to provide compound A2 which can subsequently be converted to the methoxy compound of formula A3. A3 can then be converted to enamine A4 which can then be cyclized in the presence of zinc metal and acetic acid to provide indole A5. Compound A5 can be reacted with an aryl bromide compound in the presence of a palladium catalyst to provide the N-arylated intermediate A6. Deprotection of the methoxy group of A6 provides the hydroxyindole A7. The halogenated tetracyclic intermediate A8 can be prepared by cyclization of A7. The dimetallic tetracyclic compounds of formula A9 can be prepared from A8 using standard transmetallation reactions.

Scheme A1 shows a method useful for making compounds of formula A12, which correspond to the Compounds of Formula (I), wherein A is nitrogen and Z is —C(R²)=C(R²)—.

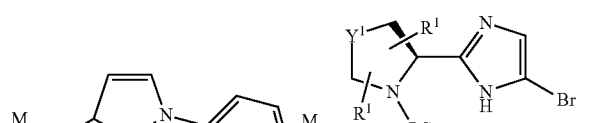

Scheme A1

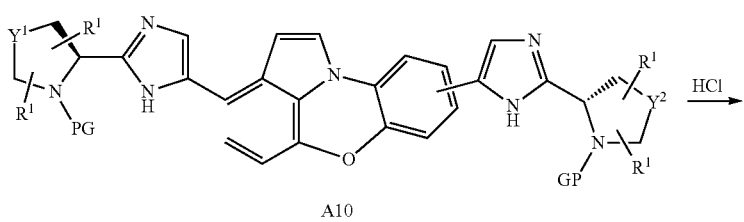

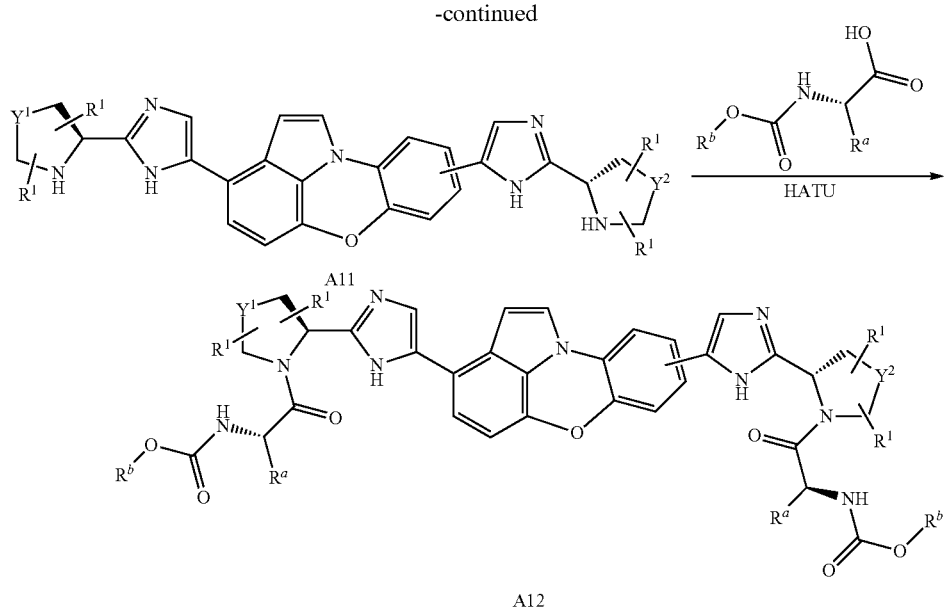

Wherein M is a boronic acid or boronic ester group and PG is a protecting group, such as Boc or a 4-methoxybenzyl group.

Scheme B shows methods useful for making the tetracyclic compounds of formula B5, which correspond to the Compounds of Formula (I), wherein A is nitrogen and the Z group is —C(R²)=N—.

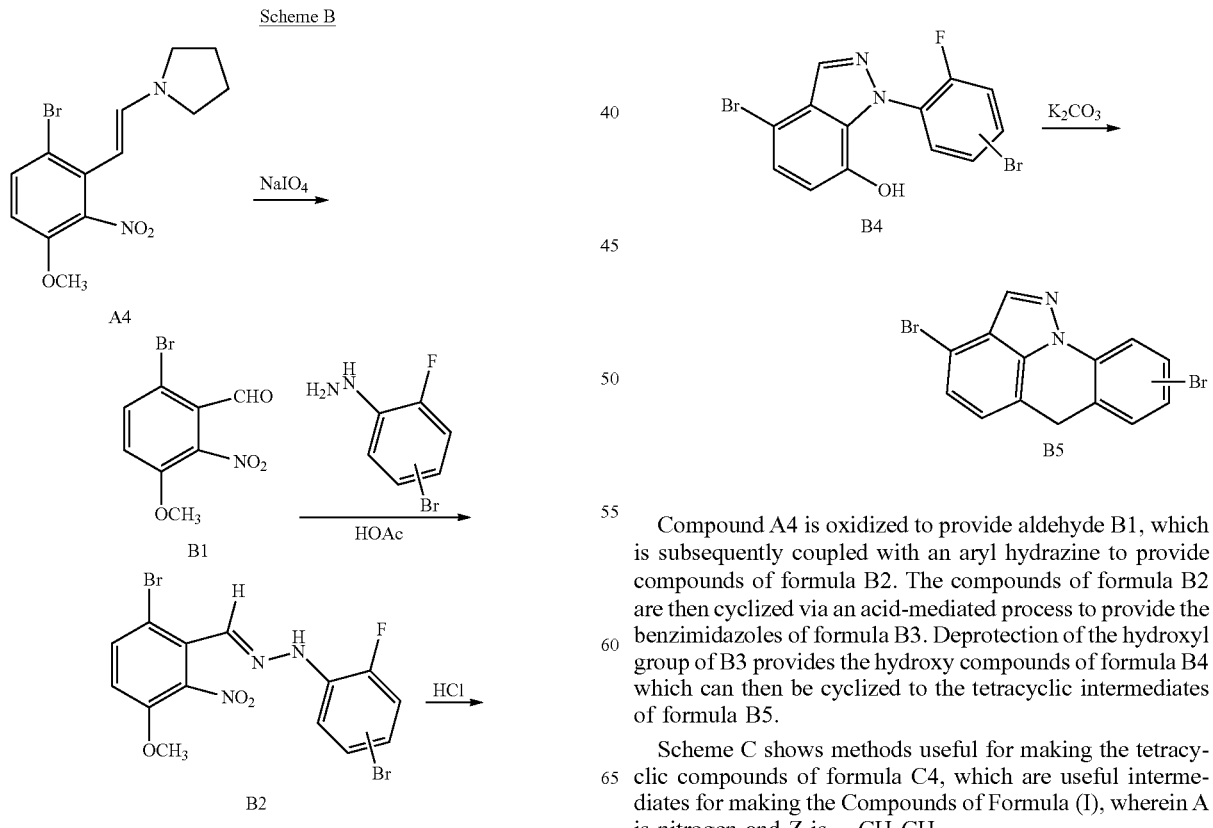

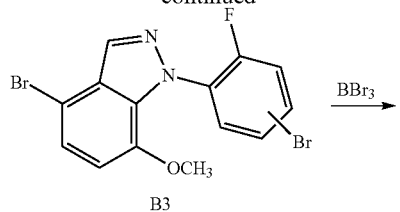

Compound A4 is oxidized to provide aldehyde B1, which is subsequently coupled with an aryl hydrazine to provide compounds of formula B2. The compounds of formula B2 are then cyclized via an acid-mediated process to provide the benzimidazoles of formula B3. Deprotection of the hydroxyl group of B3 provides the hydroxy compounds of formula B4 which can then be cyclized to the tetracyclic intermediates of formula B5.

Scheme C shows methods useful for making the tetracyclic compounds of formula C4, which are useful intermediates for making the Compounds of Formula (I), wherein A is nitrogen and Z is —CH₂CH₂—.

Scheme C

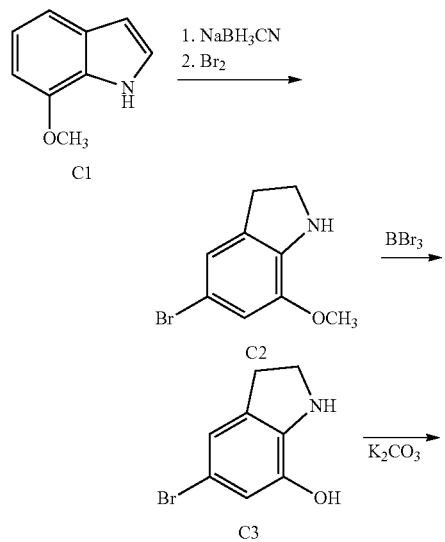

Indole C1 can be converted to the brominated compound of formula C2, followed by deprotection of the phenol hydroxyl group to provide C3. Compound C3 then be cyclicized in the presence of a carbonate base to provide the tetracyclic compounds of formula C4.

Scheme D shows methods useful for making the tetracyclic compounds of formula D6, which are useful intermediates for making the Compounds of Formula (I), wherein A is nitrogen and Z is —CH$_2$CH$_2$CH$_2$—.

Scheme D

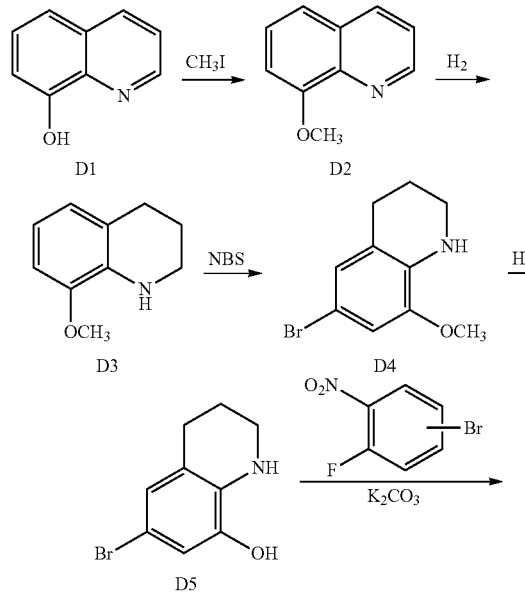

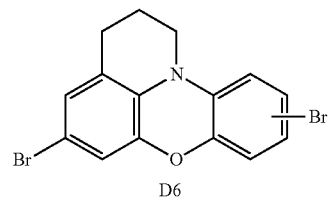

Compound D1 can be converted to the methoxy compound of formula D2, which is subsequently hydrogenated to provide compound D3. D3 can then be brominated to provide D4, which is deprotected to provide the hydroxyl compound D5. D5 is then reacted with a 2-fluoronitrobenzene derivative in the presence of a carbonate base to provide the tetracyclic compounds of formula D6

Scheme E shows methods useful for making the tetracyclic compounds of formula E9, which are useful intermediates for making the Compounds of Formula (I), wherein A is nitrogen and Z is —OCHCH$_2$—.

Scheme E

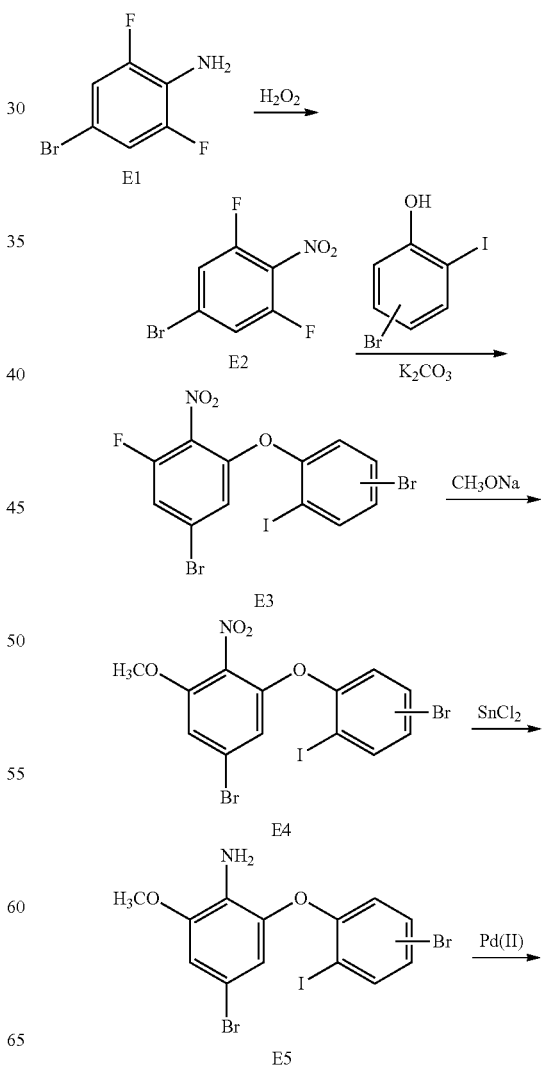

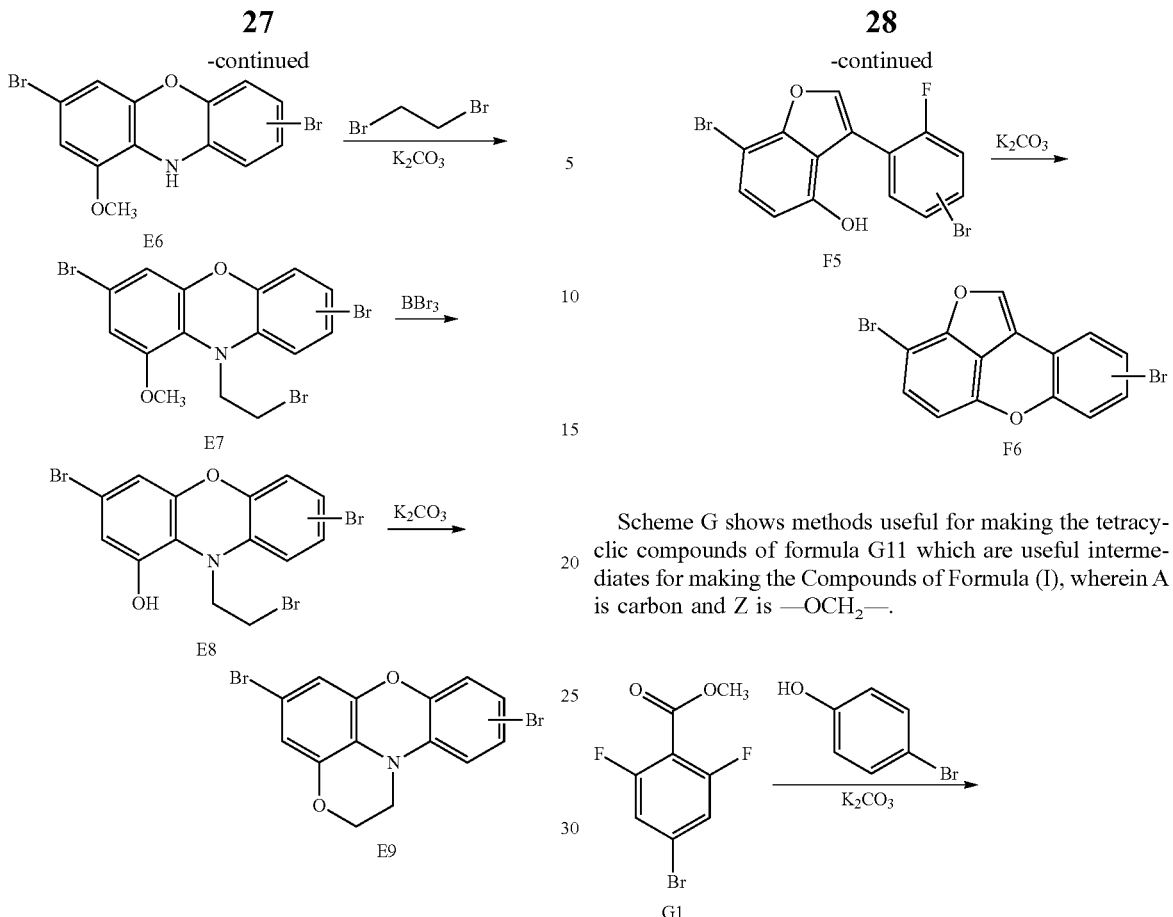

Scheme F shows methods useful for making the tetracyclic compounds of formula F6 which are useful intermediates for making the Compounds of Formula (I), wherein A is carbon and Z is —OCH=C—.

Scheme F shows methods useful for making the compounds of formula F6, which correspond to the Compounds of Formula (I), wherein Scheme G shows methods useful for making the tetracyclic compounds of formula G11 which are useful intermediates for making the Compounds of Formula (I), wherein A is carbon and Z is —OCH$_2$—.

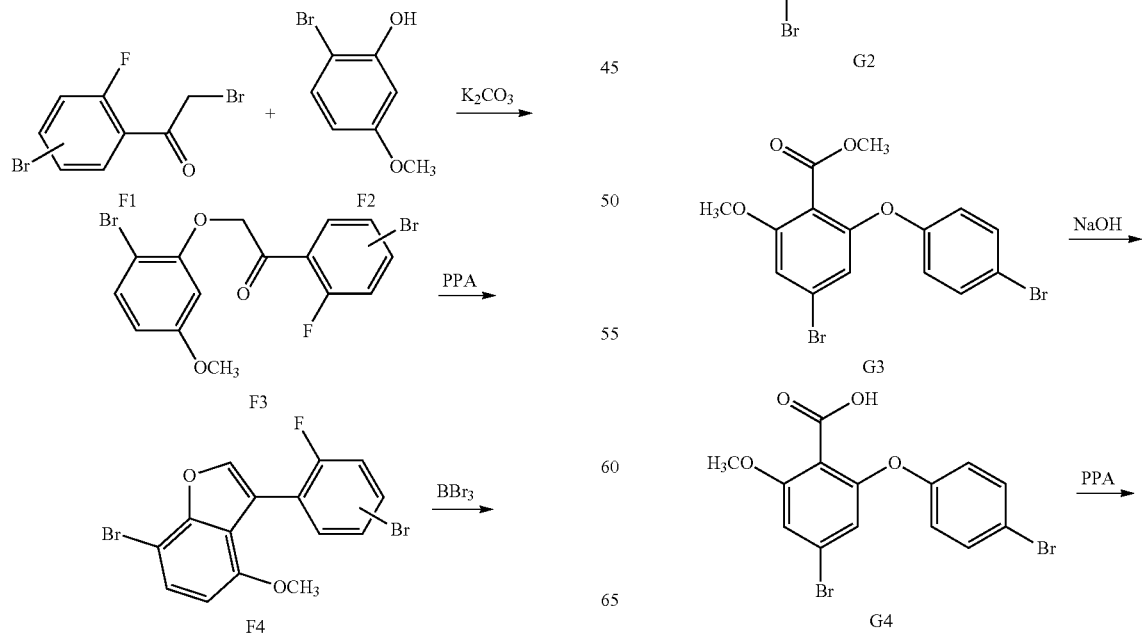

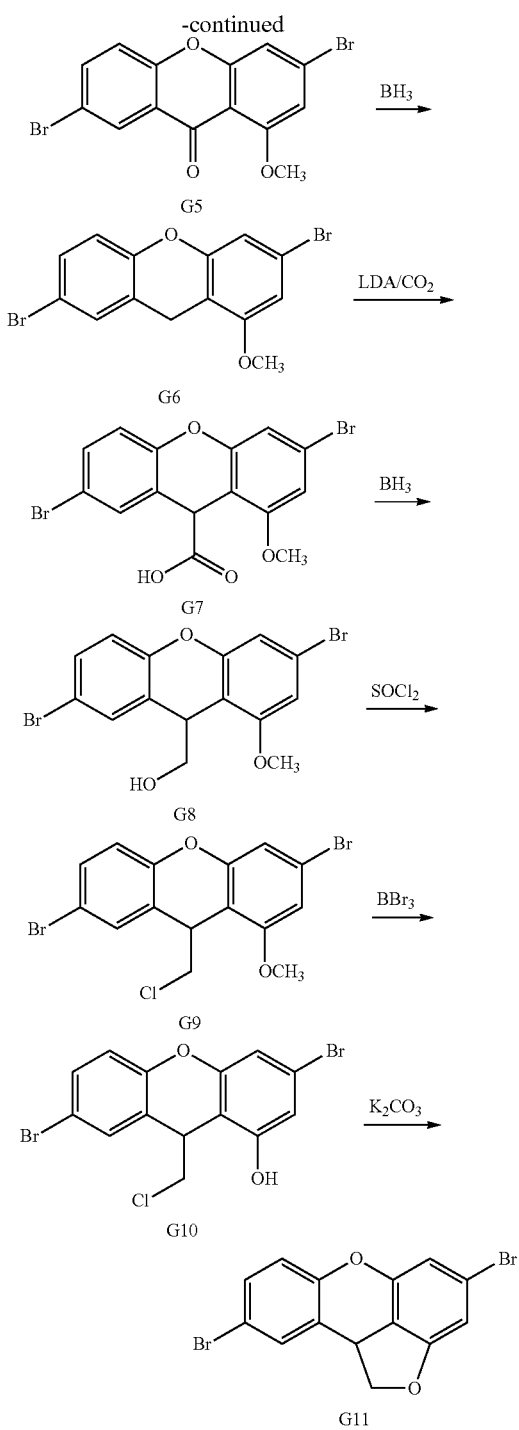

then deprotected to provide G10. G10 is then cyclized in the presence of a carbonate base to provide the tetracyclic compound G11.

Compounds of formula B5, C4, D6, E9, F6 and G11 can then be carried forth to the Compounds of Formula (I) using methods analogous to those described in Scheme A2 and in the Examples below.

In some of the Compounds of Formula (I) contemplated in Schemes A-G, amino acids (such as, but not limited to proline, 4-(R)-fluoroproline, 4-(S)-fluoroproline, 4,4-difluoroproline, 4,4-dimethylsilyiproline, aza-bicyclo[2.2.1]heptane carboxylic acid, aza-bicyclo[2.2.2]octane carboxylic acid, (S)-2-piperidine carboxylic acid, valine, alanine, norvaline, etc.) are incorporated as part of the structures. Methods have been described in the organic chemistry literature as well as in US Patent Publication No. US20090068140, for example, for the preparation of such amino acid-derived intermediates.

One skilled in the art of organic synthesis will recognize that the synthesis of fused tetracyclic cores contained in Compounds of Formula (I) may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the fused tetracyclic cores of the Compounds of Formula (I) may be more desirable depending on the choice of appendage substituents. Additionally, one skilled in the art will recognize that in some cases the order of reactions may differ from that presented herein to avoid functional group incompatibilities and thus adjust the synthetic route accordingly.

One skilled in the art of organic synthesis will recognize that the synthesis of certain fused tetracyclic cores of the Compounds of Formula (I) require the construction of an amide bond. Methods useful for making such amide bonds, include but are not limited to, the use of a reactive carboxy derivative (e.g., an acid halide, or ester at elevated temperatures) or the use of an acid with a coupling reagent (e.g., HOBt, EDCI, DCC, HATU, PyBrop) with an amine.

The preparation of multicyclic intermediates useful for making the fused tetracyclic ring systems of the Compounds of Formula (I) have been described in the literature and in compendia such as "Comprehensive Heterocyclic Chemistry" editions I, II and III, published by Elsevier and edited by A. R. Katritzky & R. JK Taylor. Manipulation of the required substitution patterns have also been described in the available chemical literature as summarized in compendia such as "Comprehensive Organic Chemistry" published by Elsevier and edited by DH R. Barton and W. D. Ollis; "Comprehensive Organic Functional Group Transformations" edited by edited by A. R. Katritzky & R. JK Taylor and "Comprehensive Organic Transformation" published by Wily-CVH and edited by R. C. Larock.

The Compounds Formula (I) may contain one or more silicon atoms. The compounds contemplated in this invention in general can be prepared using the carba-analog methodology unless otherwise noted. A recent review of the synthesis of silicon containing compounds can be found in "Silicon Chemistry: from Atom to Extended Systems", Ed P. Jutzi & U. Schubet; ISBN 978-3-527-30647-3. Preparation of silyl containing amino acids has been described. See The difluorobenzene derivative G1 can be coupled with a bromophenol to provide G2. G2 can then be converted to the corresponding methoxy compound G3, the ester group of which is subsequently hydrolyzed to provide the benzoic acid derivative G4. Cyclization of G4 to tricycle G5 is accomplished in the presence of acid and the keto group of G5 can then be reduced to provide compound G6. Carboxylation of G6 provides carboxylic acid G7, which is then reduced to the hyrdroxymethyl compound G8. The hydroxy group of G8 is converted to its chloro derivative using thionyl chloride and the phenolic hydroxy group of G9 is Bolm et al., *Angew. Chem. Int Ed.*, 39:2289 (2000). Descriptions of improved cellular update (Giralt, J. Am. Chem. Soc., 128:8479 (2006)) and reduced metabolic processing of silyl containing compounds have been described (Johansson et al., *Drug Metabolism & Disposition*, 38:73 (2009)).

The starting materials used and the intermediates prepared using the methods set forth in Schemes A-H may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from Me$_4$Si with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes-10% CH$_3$CN, 5 minutes-95% CH$_3$CN, 5-7 minutes—95% CH$_3$CN, 7 minutes—stop. The parent ion is given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Intermediate Compound Int-1a

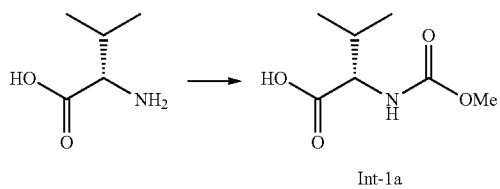

Int-1a

To a solution of L-valine (10.0 g, 85.3 mmol) in 1M aqueous NaOH solution (86 mL) at room temperature was added solid sodium carbonate (4.60 g, 43.4 mmol). The reaction mixture was cooled to 0° C. (ice bath), then methyl chloroformate (7.20 mL, 93.6 mmol) was added dropwise over 20 minutes. The reaction mixture was allowed to warm to room temperature and allowed to stir at this temperature for an additional 4 hours. The reaction mixture was then diluted with diethyl ether (100 mL), the resulting solution was cooled to 0° C., then concentrated hydrochloric acid (18 mL, 216 mmol) was added slowly. The resulting solution was extracted with EtOAc (3×100 mL) and the combined organics were dried over MgSO$_4$, filtered and concentrated in vacuo to provide Compound Int-la (13.5 g, 90%), which was used without further purification.

Example 2

Preparation of Intermediate Compound Int-2a

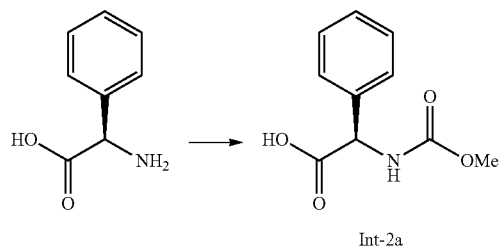 [SMILES: N[C@@H](C(=O)O)c1ccccc1 ; COC(=O)N[C@@H](C(=O)O)c1ccccc1]

Int-2a

To a solution of D-phenylglycine (10.0 g, 66.1 mmol) and NaOH (21.2 g, 265 mmol) in water (60 mL) at 0° C. was added methyl chloroformate (10.2 mL, 133 mmol) dropwise over 20 minutes. The resulting reaction was allowed to stir at 0° C. for 1 hour, then was acidified using concentrated hydrochloric acid (25 mL, 300 mmol). The acidic solution was extracted with EtOAc (3×100 mL) and the combined organics were dried over MgSO$_4$, filtered and concentrated in vacuo to provide compound Int-2a (12.6 g, 91%), which was used without further purification.

Example 3

Preparation of Intermediate Compounds Int-3a and 3b

The following intermediates can be prepared from L-tert-butylglycine and L-cyclopropylglycine with methyl chloroformate, respectively, using the method described in Example 2:

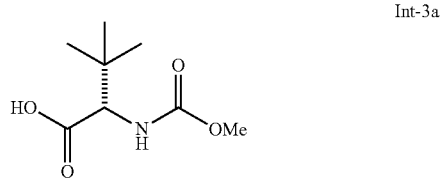

Int-3a

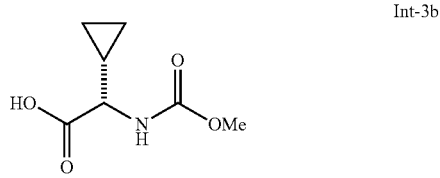

Int-3b

Example 4

Preparation of Intermediate Compound Int-4h

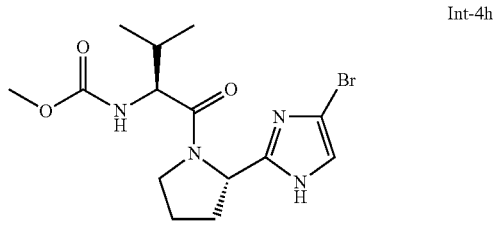 [SMILES: COC(=O)N[C@H](C(=O)N1CCC[C@H]1c1nc(Br)c[nH]1)C(C)C]

Int-4h

Step A—Synthesis of Compound Int-4b

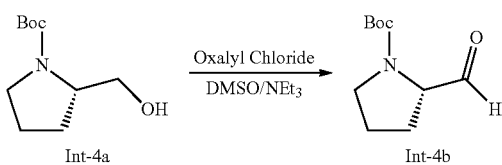 [SMILES: CC(C)(C)OC(=O)N1CCC[C@H]1CO ; CC(C)(C)OC(=O)N1CCC[C@H]1C=O]

A 2 L, 3-necked round bottomed flask equipped with an overhead stirrer and a N₂ inlet was charged with a solution of oxalyl chloride (130 mL, 0.26 mol) in dichloromethane (250 mL). The solution was cooled to −78° C., and a solution of DMSO (20 mL, 0.28 mol) in dichloromethane (3.0 mL) was added dropwise. After 30 minutes, a solution of (S)—N—Boc-prolinol, Int-4a (40 g, 0.20 mol) in dichloromethane (200 mL) was added dropwise. After 30 minutes, triethylamine (140 mL, 1.00 mol) was added to the reaction, and the flask was transferred to an ice/water bath and allowed to stir at reduced temperature for another 30 minutes. The reaction mixture was then diluted with dichloromethane (200 mL) and washed sequentially with H₂O, 1M HCl, saturated NaHCO₃, and brine, then the collected organic layer was dried over Na₂SO₄, filtered, and concentrated in vacuo to provide compound Int-4b (40 g) as oil, which was used without further purification.

Step B—Synthesis of Compound Int-4c

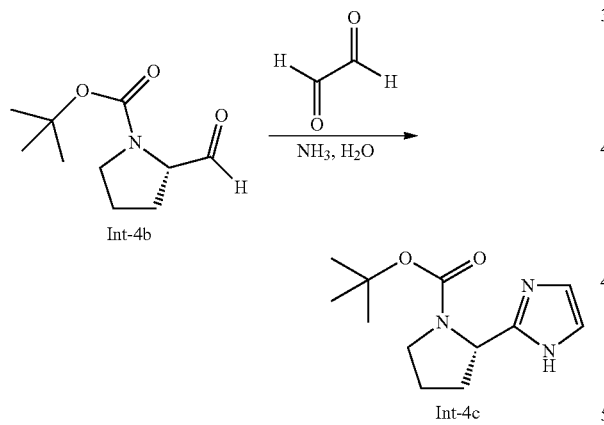

To Int-4b (crude, 80 g, 0.4 mol) was added a solution of ammonia in MeOH (prepared from 150 mL of 7 N ammonia/Meal and 200 mL MeOH, 1.05 mol, 260 mol %). An exotherm was noted with the reaction temperature rising to −30° C. The solution was allowed to stir for 0.5 hours at room temperature, then glyoxal (76 g, 0.52 mol, 130 mole %) was added over 5 minutes in portions, with the internal temperature rising to −60° C. and then returning to room temperature after 1 hour. The reaction was allowed to stir for an additional 15 hours and the reaction mixture was concentrated in vacuo. The residue obtained was diluted with dichloromethane (1 L) and water (0.5 L) and the organic phase was washed with water (0.25 L), dried over MgSO₄, filtered and concentrated in vacuo. The residue obtained was slurried with warm ethyl acetate (~100 mL) and hexane (100 mL), then was cooled and filtered. The solid obtained was washed with 30% ethyl acetate/hexane to provide compound Int-4c (66.2 g, 70% yield).

Step C—Synthesis of Compound Int-4d

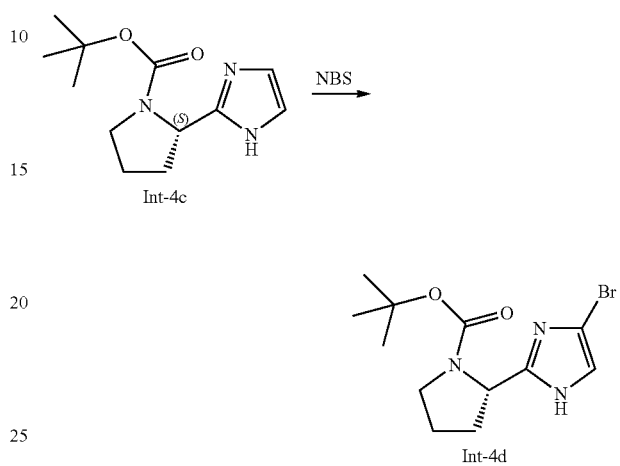

N-Bromosuccinimide (838.4 mg, 4.71 mmol) was added in portions over 15 minutes to a 0° C. solution of compound Int-4c (1.06 g, 4.50 mmol) in CH₂Cl₂ (20 mL). The reaction mixture was allowed to stir for 75 minutes at 0° C., then was concentrated in vacuo. The oily residue obtained was purified using silica-gel RPLC (acetonitrile/water/0.1% TFA) to separate the mono-bromide from its dibromo analog. The RPLC elute was neutralized with excess NH₃/MeOH, and the volatile component was removed in vacuo. The residue obtained was partitioned between CH₂Cl₂ and water, and the aqueous layer was extracted with water. The combined organic phases were dried (MgSO₄), filtered, and concentrated in vacuo to provide Compound Int-4d as a white solid (374 mg). ¹H NMR (DMSO) δ: 12.12 (br s, 1H), 7.10 (m, 1H), 4.70 (m, 1H), 3.31 (m, 1H; overlapped with water signal), 2.25-1.73 (m, 4H), 1.39/1.17 (s, 3.8H+5.2H).

Step D—Synthesis of Compound Int-4e

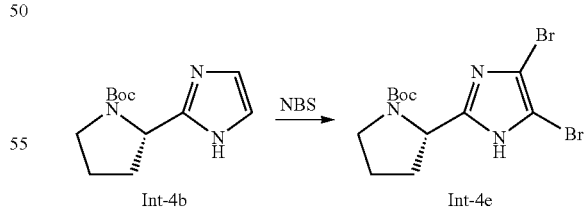

To a suspension of Int-4b (140 g, 0.59 mol) in THF (2000 mL) was added N-bromosuccinimide (200 g, 1.1 mol). The reaction was allowed to stir at room temperature under N₂ atmosphere for about 15 hours. The reaction mixture was then concentrated in vacuo, and the residue obtained was purified using silica-gel chromatography (ethyl acetate eluent) to provide 230 g of the desired dibromo compound, Int-4e. MS (ESI) m/e (M+H⁺): 396.

Step E—Synthesis of Compound Int-4f

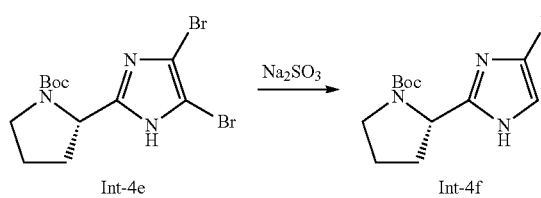

To a suspension of Int-4e (230 g, 0.58 mol) in EtOH/H$_2$O (1:1 ratio, 3000 mL) was added Na$_2$SO$_3$ (733 g, 5.8 mol). The resulting reaction was heated to reflux and allowed to stir at this temperature for about 15 hours. After cooling to room temperature, the reaction mixture was extracted with dichloromethane (2×1 L) and the combined organic extracts were concentrated in vacuo. The semi-solid residue obtained was purified using chromatography on silica gel (EtOAc eluent) to provide compound Int-4d. MS (ESI) m/e (M+H$^+$): 317.

Example 5

Preparation of Intermediate Compound Int-5f

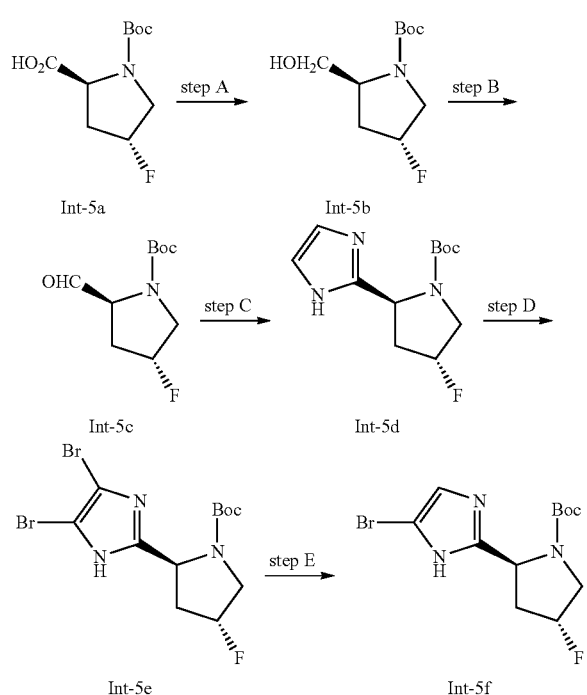

Step A—Synthesis of Compound Int-5b (2S,4R)-1-(tert-butoxycarbonyl)-4-fluoropyrrolidine-2-carboxylic acid (Int-5a, 20 g, 85.75 mmol) was dissolved in anhydrous THF and cooled to 0° C. BH$_3$.THF (1M in THF, 171 mL, 171 mmol) was added via an addition funnel and the reaction was allowed to warm to room temperature on its own and stir for a total of about 15 hours. MeOH was added to the reaction mixture until gas evolution ceased, then the resulting solution was concentrated in vacuo, and the residue obtained was purified using silica gel chromatography (330 g, 0% to 60% of EtOAc in Hexane) to provide Compound Int-5b (15.1 g, 80.3%)

Step B Synthesis of Compound Int-5c

To a dry 1000 mL round bottom flask was added oxalyl chloride (7.50 mL, 88.9 mmol) and dry dichloromethane (250 mL) and the resulting solution was cooled to −78° C. DMSO (6.80 mL, 95.8 mmol) in dichloromethane (20 mL) was added dropwise to the cooled solution and the resulting reaction was allowed to stir at −78° C. for 30 minutes. A solution of Int-10b (15.0 g, 68.4 mmol) in dichloromethane (50 mL) was then added via syringe and the reaction was allowed to stir at −78° C. for 30 minutes, after which time triethylamine (38.1 mL, 273.6 mmol) was added. The resulting reaction was allowed to stir at −78° C. for 30 minutes, then at 0° C. for 1 hour. The reaction mixture was diluted with dichloromethane (300 mL), then washed sequentially with water, 1N HCl, sat NaHCO$_3$, and brine. The organic phase was dried over anhydrous Na$_2$SO$_4$, filtered and concentrated in vacuo and the residue obtained was dried in vacuo for 1 hour to provide Compound Int-5c which was used without further purification.

Step C—Synthesis of Compound Int-5d

To a 1000 mL round bottom flask was added Int-5c and NH$_3$ (7N in MeOH, 150 mL). Glyoxal (15 mL, 40% in water, 131 mmol) slowly added and the resulting reaction was allowed to stir at room temperature for about 15 hours. Additional glyoxal (5 mL, 44 mmol) was added and the reaction was allowed to stir at room temperature for another 24 hours. The reaction was concentrated in vacuo and the residue obtained was purified using silica gel chromatography (240 g, 0% to 5% MeOH in dichloromethane, with 0.1% NH$_3$.H$_2$O) to provide Compound Int-5d.

Step D—Synthesis of Compound Int-5e

Compound Int-5d (8.5 g, 33.3 mmol) was taken up in enough CH$_3$CN to form a clear solution (~300 mL). To the resulting solution was added NBS (11.3 g, 63.3 mmol) in one portion and the resulting reaction was allowed to stir at room temperature for about 15 hours. The reaction mixture was concentrated in vacuo and the residue obtained was taken up in dichloromethane (50 mL) with stirring. The resulting suspension was filtered and the collected solid was washed with dichloromethane twice. The filtrate and combined washings were concentrated in vacuo to about 30 mL in volume and the resulting solution was filtered again. The filtrate was purified using silica gel chromatography (120 g, 20% to 80% of EtOAc in Hexane) to provide Compound Int-5e (11.88 g, 86.4%).

Step E—Synthesis of Compound Int-5f

To a 1000 mL round bottom flask was added Int-5d (11.88 g, 28.76 mmol), sodium sulfite (Na$_2$SO$_3$, 36.0 g, 288 mmol), EtOH (270 mL) and water (130 mL). The reaction mixture was heated to reflux and allowed to stir at this temperature for about 15 hours. Additional Na$_2$SO$_3$ (10 g, 79 mmol) was added and the reaction mixture was allowed to stir at reflux for another 24 hours, then cooled to room temperature. The reaction mixture was filtered and the collected solid was washed with EtOAc (3×200 mL). The filtrate and combined washings were concentrated in vacuo and the residue obtained was dissolved in a mixture of EtOAc (300 mL) and water (200 mL). The organic layer was separated and washed with brine, dried over anhydrous Na$_2$SO$_4$, filtered, and concentrated in vacuo. The residue obtained was purified using silica gel chromatography (240 g, 0% to 33% of EtOAc in hexanes) to provide Compound Int-5f (5.12 g, 53.3%).

Example 6

Preparation of Intermediate Compound Int-6c

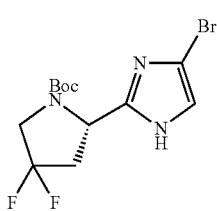

Int-6c

Step A—Synthesis of Compound Int-6b

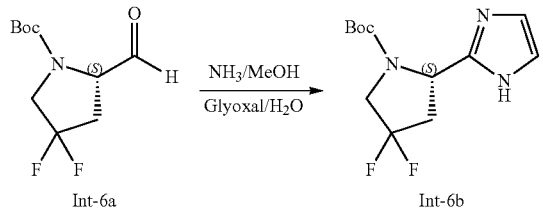

Aldehyde Int-6a (82 g, 0.35 mol, prepared from the commercially available corresponding alcohol using the method described in Example 10) was taken up in a 2.33 N ammonia/MeOH solution (600 mL, 4.0 eq., prepared from 200 mL 7N ammonia/MeOH diluted with 400 ml MeOH). The reaction was then heated to 35° C. and allowed to stir at this temperature for 2 hours, after which time a solution of 40 wt % glyoxal in water (80 mL, 2.0 eq.) was added dropwise over about 15 minutes. After stirring for an additional 2 hours, a solution of 7N ammonia/MeOH (100 mL, 2.0 eq.) was added and the reaction was allowed to stir at 35° C. for 1 hour. Additional glyoxal (40 mL, 1.0 eq.) was then added dropwise over 5 minutes and the resulting reaction was allowed to stir at 35° C. for 1 hour. The reaction mixture was then allowed to cool room temperature and stir for about 15 hours. Additional 7N ammonia/MeOH (50 mL, 1.0 eq.) was then added and the reaction was heated to 35° C. and allowed to stir at this temperature for 1 hour. An additional amount of glyoxal (20 mL, 0.5 eq.) was then added and the resulting reaction was allowed to stir at 35° C. for 1 hour, then the reaction mixture was cooled to room temperature and filtered. The filtrate was concentrated in vacuo and the residue obtained was diluted with dichloromethane and water (2 L, 1:1). The organic layer was separated, washed with 1 L of water, then brine and dried (MgSO$_4$), filtered and concentrated in vacuo. The brown foam residue obtained was further purified by being passed through a short silica gel column to provide Compound Int-6b (60 g, 62%).

Step B—Synthesis of Compound Int-6c

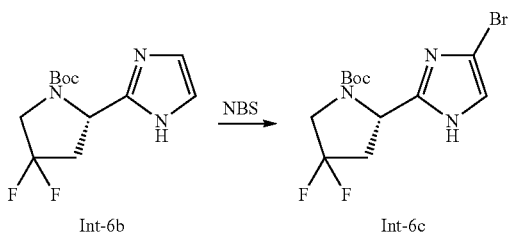

Int-6c was prepared from Int-6b using the method described in Example 5.

Example 7

Preparation of Intermediate Compounds Int-7d and Int-7e

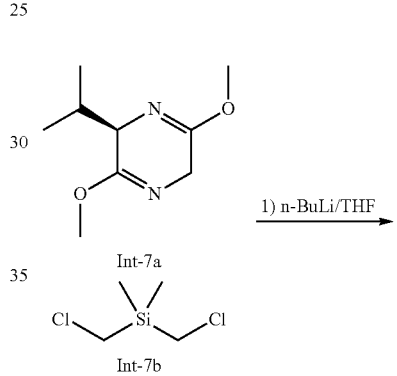

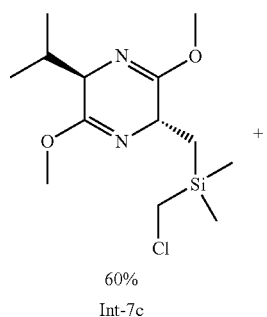

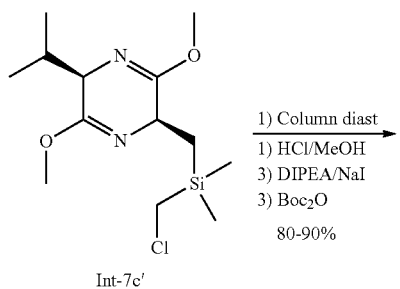

-continued

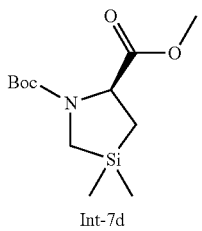

Int-7d

Step A—Synthesis of Compound Int-7c

A 5 liter, 3-neck round bottomed flask, equipped with a mechanical stirrer, temperature probe, addition funnel and $N_2$ inlet, was charged with the (R)-2,5-Dihydro-3,6-dimethoxy-2-isopropylpyrazine (Int-7a, 200 g, 1.09 mol, 1.0 eq), bis(chloromethyl) dimethylsilane (Int-71), 256 g, 1.63 mol, 1.5 eq), and THF (2 L, Aldrich anhydrous). The flask was cooled in a dry ice/2-propanol bath until the internal temperature reached $-75°$ C. n-Butyllithium (Aldrich 2.5 M in hexanes, 478 mL, 1.19 mol, 1.09 eq) was added via a dropping funnel over 1 hour while maintaining the internal reaction temperature between $-67°$ C. and $-76°$ C. The resulting orange-red solution was allowed to gradually warm to room temperature with stirring for about 15 hours. The reaction mixture was then cooled to $0°$ C. and quenched with 500 mL of water. Diethyl ether (2 L) was added and the layers were separated. The aqueous layer was extracted with 1 L of diethyl ether. The combined organic extracts was washed with water and brine, dried over $MgSO_4$, filtered and concentrated in vacuo. The orange oily residue was dried in vacuo for about 15 hours to provide 420 g of oil. The crude product was split into two batches and purified via silica gel chromatography on a 1.6 kg flash column (eluted with gradient of 0-4% $Et_2O$ in hexanes). The product fractions were concentrated in vacuo at a bath temperature at or below $40°$ C. to provide compound Int-7c (190 g, 60% yield).

Step B—Synthesis of Compound Int-7d

A 5 L, 3-necked round bottomed flask equipped with a mechanical stirrer, addition funnel, temperature probe, external water bath and $N_2$ inlet was charged with Compound Int-7c (196 g, 0.643 mol, 1.0 eq) and methanol (1.5 L). Aqueous HCl (500 mL of 10% by volume) was added at room temperature over 30 minutes, with a mild exotherm observed, during which the reaction temperature increased to $37°$ C. The reaction mixture was allowed to stir at room temperature for 3 hours then the reaction mixture was then concentrated in vacuo to an oil. Additional methanol (3×200 mL) was added to the oil and the reaction mixture was concentrated in vacuo. The resulting residue was dried under house vacuum for about 15 hours, then was taken up in $CH_2Cl_2$ (750 mL) and $Et_2O$ (1250 mL) and to the resulting solution was added sodium iodide (96.4 g, 0.643 mol, 1.0 eq). Diisopropylethylamine (336 mL, 1.929 mol, 3.0 eq) was then added slowly over 25 minutes with stirring, causing the temperature to temporarily increase to $35°$ C. After addition was complete, the reaction was allowed to stir at room temperature for 4 hours, then Boc-anhydride (281 g, 1.28 mol, 2.0 eq) was added. The resulting reaction was allowed to stir at room temperature for 48 hours, then the reaction mixture was diluted with EtOAc (2 L) and water (1 L), and the layers were separated. The aqueous phase was extracted with 500 mL of EtOAc and the combined organics were washed with water (500 mL), and brine (500 mL), dried with $MgSO_4$, filtered and concentrated in vacuo. The yellow oily residue obtained was divided into two separate portions of equal weight and each portion was purified using flash silica gel chromatography. Column conditions for each portion of crude product (180 g) were as follows: 180 grams of crude product was loaded onto a 191 g $SiO_2$ cartridge and purified on a 1.5 kg $SiO_2$ column. The column was eluted using a 0%-20% EtOAc/hexanes gradient as the mobile phase to provide 52 grams of pure Int-7d and additional fractions of Int-7d that contained a small amount of a Boc-valine impurity. The impure fractions from the two columns were recombined and re-purified. After chromatography, Compound Int-7d was obtained as an oil, which solidified to a white solid on standing (128 g, 65% yield over the three steps.)

Step C—Synthesis of Compound Int-7e

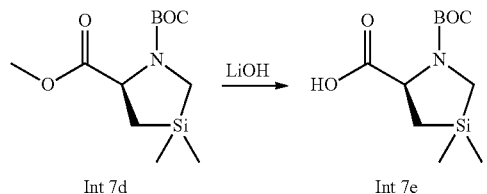

A solution of Int-7d (8.5 g, 31.1 mmol) in methanol (100 mL) and 1.0 M aqueous KOH solution (48 mL, 48 mmol) was allowed to stir at room temperature for about 15 hours. The reaction was then neutralized with 48 mL of 1.0 M aqueous HCl solution to pH ~5, and partially concentrated in vacuo. The aqueous layer was then extracted twice with dichloromethane (2×100 mL) and the combined organic extracts were concentrated in vacuo to provide Compound Int-7e as a gel (7.74 g, 96%). Note: Because of poor UV absorbance, the above reactions were monitored by TLC using Hanessian's stain. To prepare the visualization stain, combine 450 mL of water, 25 g ammonium molybdate, 5 g of eerie sulfate, and 50 mL of conc. HCl.

Example 8

Preparation of Intermediate Compound Int-8d

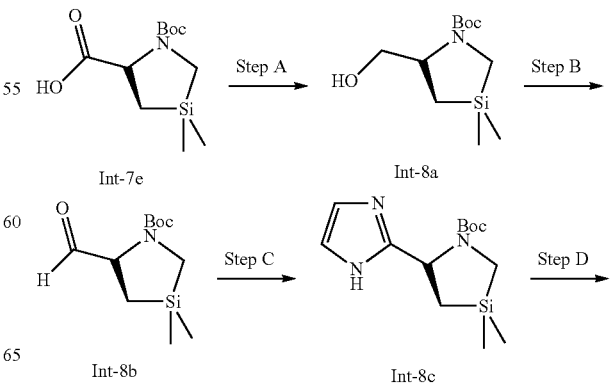

-continued

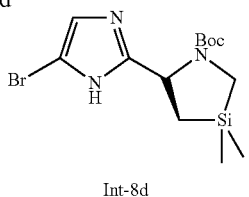

Int-8d

Step A—Synthesis of Compound Int-8a

To a mixture of carboxylic acid Int-7e (20 g, 77 mmol) in THF (400 mL) at 0° C. was added a solution of 1M $BH_3$ in THF (0.17 L, which was pre-cooled to 0° C.) via addition funnel. The cold bath was removed and the reaction was allowed to stir for about 15 hours, during which time the reaction mixture warmed to room temperature. The reaction was carefully quenched by addition of MeOH (~75 mL) until gas evolution ceased and the reaction mixture was concentrated in vacuo. The residue obtained was partitioned between EtOAc and $H_2O$ and the aqueous layer was extracted with EtOAc (2×200 mL). The organic phase and organic extracted were combined, washed with brine, dried ($Na_2SO_4$), and concentrated in vacuo to provide Compound Int-8a (18 g, 99%) as a clear oil, which was used without further purification. MS (ESI) m/e (M+H+Na)$^+$: 268.

Step B—Synthesis of Compound Int-8b

To a dry 2-necked flask equipped with a stir bar was added oxalyl chloride (8.2 mL, 96 mmol) and $CH_2Cl_2$ (280 mL). The solution was cooled to −78° C. whereupon a solution of DMSO (7.4 mL, 0.10 mol) in $CH_2Cl_2$ (22 mL) was added and the mixture was allowed to stir for 30 minutes at −78° C. A solution of alcohol Int-8a (18 g, 74 mmol) in $CH_2Cl_2$ (60 mL) was added dropwise via addition funnel over 30 minutes. The resulting solution was allowed to stir for an additional 30 minutes at −78° C. whereupon $Et_3N$ (42 mL, 0.30 mol) was added dropwise. The reaction was allowed to stir for 30 minutes at −78° C., warmed to 0° C., and allowed to stir at this temperature for an additional 1.5 hours. The reaction mixture was diluted with $CH_2Cl_2$ (400 mL) and transferred to a separatory funnel. The organic layer was washed with sat. aq $NH_4Cl$ (2×100 mL) and brine (2×100 mL), then was dried ($Na_2SO_4$), filtered and concentrated in vacuo to provide compound Int-8b, 18 g (99%) as a clear oil, which was used without further purification.

Step C—Synthesis of Compound Int-8c

A solution of aldehyde Int-8b (18 g, 74 mmol) in a solution of 7N $NH_3$ in MeOH (28 mL, 0.19 mol) in MeOH (37 mL) was allowed to stir for 30 minutes at room temperature, whereupon a solution of glyoxal (14 g, 96 mmol) was added over 5 minutes. The resulting reaction was allowed to stir for 12 hours at room temperature, then was concentrated in vacuo. The residue obtained was purified using column chromatography (gradient of 100% $CH_2Cl_2$ to 97.5% $CH_2Cl_2$/2.5% MeOH) to provide Compound Int-8c, (9.9 g, 48%) as yellow oil. MS (ESI) m/e (M+H)$^+$: 282.

Step D—Synthesis of Compound Int-8d

To a solution of compound Int-8c (1.0 g, 3.6 mmol) in $CH_2Cl_2$ (5 mL) at 0° C., was added a solution of NBS (0.44 g, 2.5 mmol) in $CH_2Cl_2$ (10 mL) dropwise via addition funnel. The resulting mixture was allowed to stir for 90 minutes at 0° C. whereupon the mixture was concentrated in vacuo. The residue obtained was partitioned between $CHCl_3$ (10 mL) and water (3 mL) and the layers were separated. The organic layer was washed with water (3×3 mL), dried ($Na_2SO_4$), filtered, and concentrated in vacuo. The residue obtained was purified using column chromatography (gradient of 100% hexanes to 65% hexanes/35% EtOAc) to provide Compound Int-8d (0.35 g, 27%) as a white solid. MS (ESI) m/e (M+H)$^+$: 360/362.

Example 9

Preparation of Methyl [(2S)-1-{(2S)-2-[5-(3-{2-[(2S)-1-{(2S)-2-[(methoxy carbonyl)amino]-3-methyl-butanoyl}pyrrolidin-2-yl]-1H-imidazol-5-yl}pyrrolo[3,2,1-kl]phenoxazin-8-yl)-1H-imidazol-2-yl]pyrrolidin-1-yl}-3-methyl-1-oxobutan-2-yl] carbamate (Compound 1)

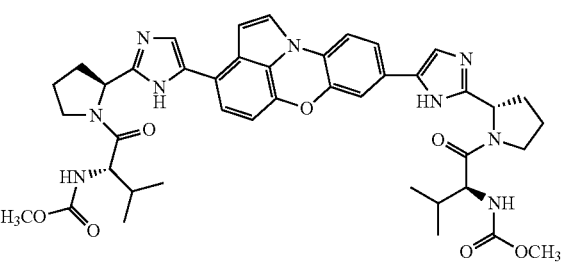

Step A—Synthesis of Compound Int-9a

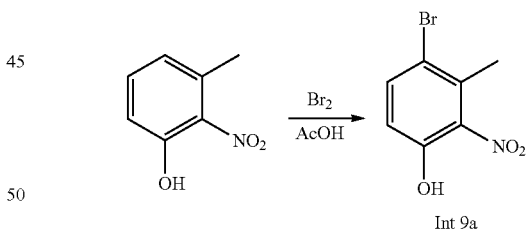

3-Methyl-2-nitrophenol (20 g, 0.13 mol) was dissolved in acetic acid (200 mL) and the solution was cooled to 0° C. Bromine (20.9 g, 0.13 mol, dissolved in 50 mL acetic acid) was added dropwise with stirring and the resulting reaction was allowed to stir for 1 hour at 0° C., then the reaction mixture was poured into ice water. The mixture was extracted with EtOAc (2×500 mL) and the combined organic extracts were washed with 5% $NaHCO_3$ (2×200 mL), dried over anhydrous $Na_2SO_4$, filtered and concentrated in vacuo to provide compound Int-9a as an orange solid (18.1 g, 60%). This material was used in the next step without further purification. $^1$H-NMR: (DMSO) δ: 11.1 (s, 1H), 7.61-7.58 (d, J=8 Hz, 1H), 6.89-6.87 (d, J=8 Hz, 1H), 2.24 (s, 3H).

Step B—Synthesis of Compound Int-9b

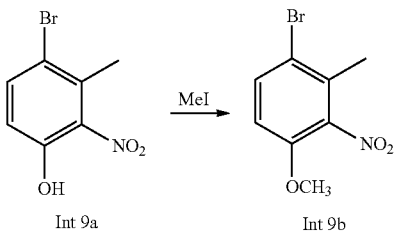

Int-9a (18.1 g, 78 mmol) was dissolved in acetone (200 mL) then K$_2$CO$_3$ (8.65 g, 156 mmol) was added followed by MeI (22.0 g, 156 mmol). The reaction mixture was allowed to stir at room temperature for 18 hours then the reaction mixture was concentrated in vacuo and H$_2$O was added to the resulting residue. The slurry obtained was extracted with CH$_2$Cl$_2$, dried over Na$_2$SO$_4$, filtered and concentrated in vacuo to provide compound Int 9b (18 g, 94%), which was used without further purification. $^1$H NMR: (DMSO) δ: 7.80-7.78 (d, J=7.8 Hz, 1H), 7.18-7.15 (d, J=7.8 Hz, 1H), 3.87 (s, 3H), 2.24 (s, 3H).

Step C—Synthesis of Compound Int-9c

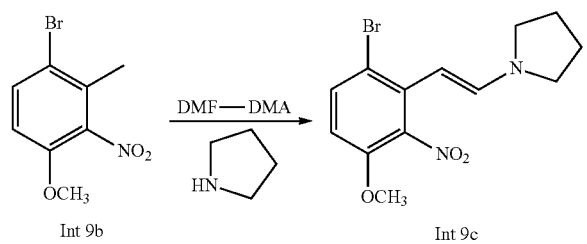

To a solution of compound Int-9b (9 g, 36.6 mol) in 60 mL of DMF was added N,N-dimethylformamide dimethylacetal (5.3 g, 44 mmol) and pyrrolidine (3.1 g, 44 mmol). The reaction mixture was heated to reflux and allowed to stir at this temperature for 3 hours under nitrogen and then cooled to room temperature. The reaction mixture was concentrated in vacuo and the red residue obtained was dissolved in 20 mL of methylene chloride and 0.2 L of methanol. The solution was concentrated in vacuo to a volume of about 0.2 L, then was cooled to 5° C. and filtered. The collected solid was washed twice with 20 mL of cold methanol and dried under vacuum to provide compound Int-9c (6 g, 51%) as red crystals, which was used without further purification. $^1$H NMR: (CDCl$_3$) δ 7.51-7.49 (d, J=5.6 Hz, 1H), 6.92-6.88 (d, J=14.4 Hz, 1H), 6.51-6.49 (d, J=8 Hz, 1H), 4.85-4.81 (d, J=14.4 Hz, 1H), 3.83 (s, 1H), 3.25-3.23 (m, 4H), 2.81 (s, 2H), 1.92-1.90 (d, J=6.8 Hz, 4H). MS (ESI) m/z (M+H)$^+$: 327.

Step D—Synthesis of Compound Int-9d

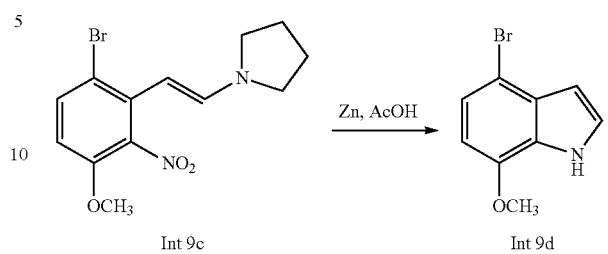

Compound Int-9c (1 g, 3.1 mmol) was dissolved in acetic acid, and added dropwise to a refluxing solution of Zn (1.0 g, 15.5 mmol) in acetic acid (40 mL). The reaction mixture was heated to reflux and allowed to stir at this temperature for 30 minutes, then allowed to cool to room temperature. Water was added and the mixture was neutralized with Na$_2$CO$_3$, extracted with CH$_2$Cl$_2$, dried over Na$_2$SO$_4$, filtered and concentrated in vacuo. The crude material was purified using column chromatography on silica to provide compound Int-9d as dark oil (500 mg, 71%). $^1$H NMR: (DMSO) δ 11.6 (s, 1H), 7.34 (s, 1H), 7.11-7.09 (d, J=8 Hz, 1H), 6.61-6.59 (d, J=8 Hz, 1H), 6.34 (s, 1H), 3.86 (s, 3H). MS (ESI) m/z (M+H)$^+$: 226.

Step E—Synthesis of Compound Int-9e

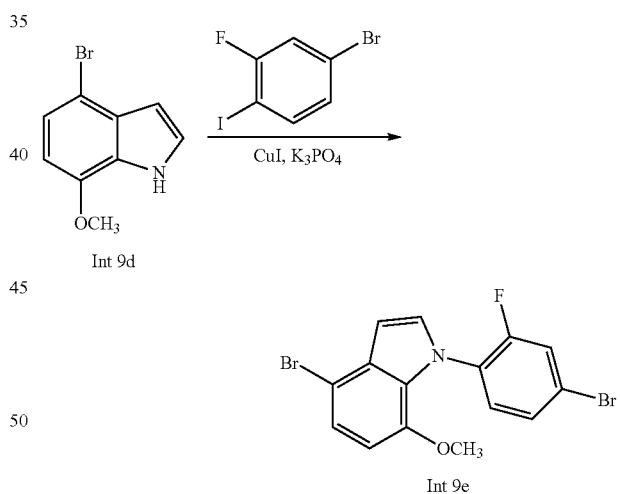

A suspension of compound Int-9d (2 g, 8.8 mmol), aryl iodide (2.6 g, 8.8 mmol), CuI (67 mg, 0.35 mmol) and K$_3$PO$_4$ (2.4 g, 17.6 mmol) in dioxane (50 mL) was put under N$_2$ atmosphere, heated to reflux, and allowed to stir at this temperature for about 15 hours. The reaction was cooled to room temperature and filtered and the filtrate was washed with water (50 mL) and extracted with EtOAc (200 mL). The organic extract was washed with brine, dried over anhydrous sodium sulfate, filtered and concentrated in vacuo. The residue obtained was purified using column chromatography to provide compound Int-9e (1.3 g, 37%). MS (ESI) m/z (M+H)$^+$: 400.

Step F—Synthesis of Compound Int-9f

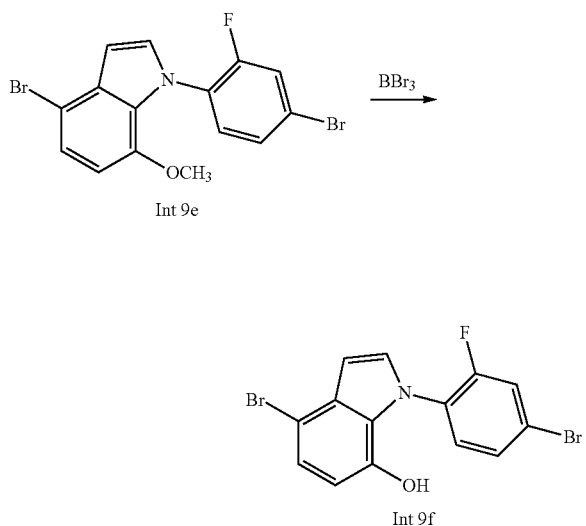

To a solution of compound Int-9e (1 g, 2.5 mmol) in dichloromethane (20 mL) was added a solution of BBr$_3$ (2.4 mL, 24 mmol) in dichloromethane and the suspension was allowed to stir at room temperature for about 15 hours. The reaction mixture was then added to an aqueous solution of saturated NaHCO$_3$ and extracted with dichloromethane. The organic extract was dried over sodium sulfate, filtered and concentrated in vacuo to provide compound Int-9f (0.5 g, 52%). MS (ESI) m/z (M+H)$^+$: 386.

Step G—Synthesis of Compound Int-9g

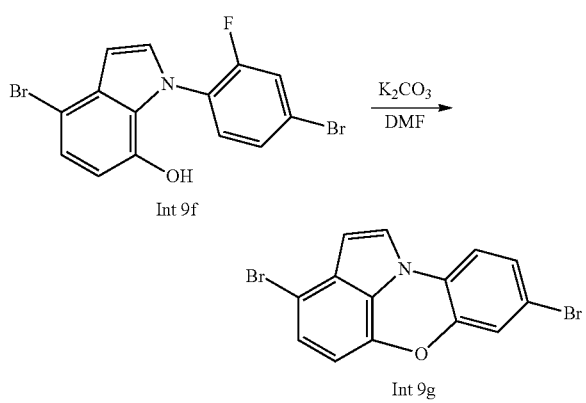

A suspension of compound Int-9f (0.5 g, 1.3 mmol) and K$_2$CO$_3$ (0.36 g, 2.6 mmol) in DMF (20 mL) was heated to reflux and allowed to stir at this temperature for 2 hours under N$_2$ atmosphere. The mixture was cooled and filtered and the filtrate was washed with water (50 mL) and extracted with EtOAc (100 mL). The extract was washed with brine, dried over anhydrous sodium sulfate, filtered and concentrated in vacuo. The residue obtained was purified using column chromatography to provide compound Int-9g (0.3 g, 64%). MS (ESI) m/z (M+H)$^+$: 366.

Step H—Synthesis of Compound Int-9h

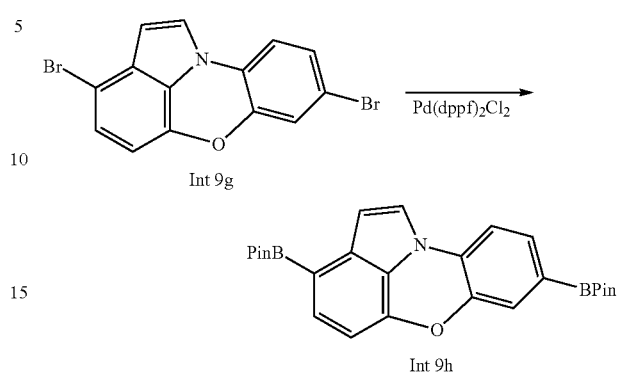

To a solution of compound Int-9g (300 mg, 0.8 mmol) in 1,4-dioxane was added bis(pinacolato)diboron (417 mg, 1.6 mmol), Pd(dppf)Cl$_2$ (58 mg, 0.08 mmol) and KOAc (203 mg, 2.0 mmol). The reaction was put under N$_2$ atmosphere, heated to 110° C. and allowed to stir at this temperature for about 15 hours. The reaction was cooled to room temperature, concentrated in vacuo, and the residue obtained was purified using column chromatography to provide compound Int-9h (200 mg, 55%). MS (ESI) m/z (M+H)$^+$: 460.

Step I—Synthesis of Compound Int-9i

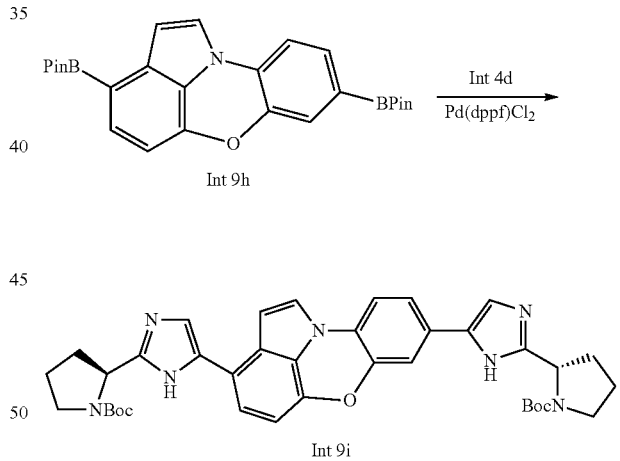

A suspension of compound Int-9h (200 mg, 0.43 mmol), compound Int-4d (271 mg, 0.86 mmol), Pd(dppf)Cl$_2$ (58 mg, 0.08 mmol) and Na$_2$CO$_3$ (182 mg, 1.72 mmol) in THF/H$_2$O (10:1, 15 mL) was heated to reflux and allowed to stir at this temperature for about 15 hours under a nitrogen atmosphere. The reaction mixture was cooled to room temperature, filtered and the filtrate was washed with water (20 mL) and extracted with EtOAc (50 mL). The combined organic extracts were washed with brine, dried over anhydrous sodium sulfate, filtered and concentrated in vacuo. The residue obtained was purified using column chromatography to provide compound Int-9i (150 mg, 51%). MS (ESI) m/z (M+H)$^+$: 678.

Step J—Synthesis of Compound Int-9j

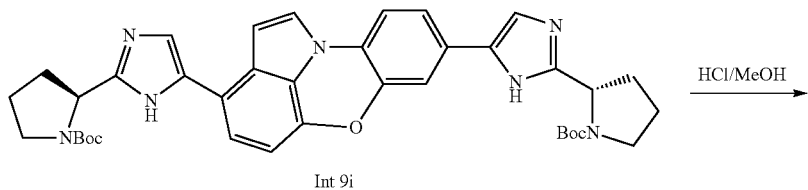

Int 9i

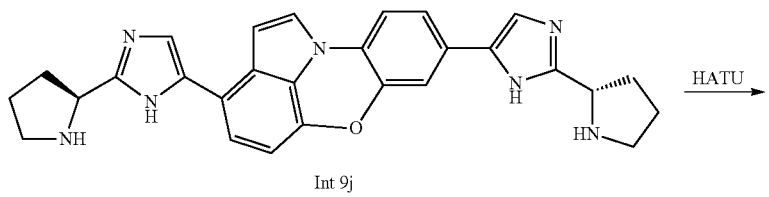

Int 9j

Compound Int-9i (150 mg, 0.22 mmol) was added into a solution of methanol (5 mL) that had been pre-saturated with HCl gas. The reaction was allowed to stir at room temperature for 2 hours then was concentrated in vacuo to provide compound Int-9i (100 mg, 80%) which was used without further purification. MS (ESI) m/z (M+H)$^+$: 478.

Step K—Synthesis of Compound 1

Int 9j

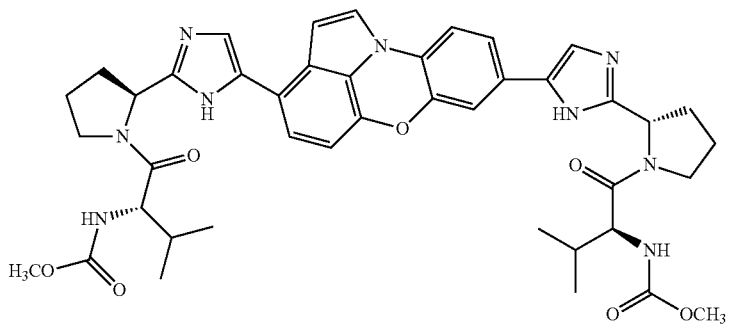

1

To a mixture of compound Int-9j (100 mg, 0.2 mmol), compound Int-1a (70 mg, 0.4 mmol) and DIPEA (155 mg, 1.2 mmol) in CH$_3$CN (5 mL) was added HATU (152 mg, 0.4 mmol). The resulting reaction was allowed to stir at room temperature for 5 hours, then the reaction mixture was filtered and the filtrate was purified using HPLC to provide the desired product (30 mg, 20%), washed with brine, dried over anhydrous sodium sulfate, filtered and concentrated in vacuo. The residue obtained was purified using reverse phase chromatography to provide compound 1. $^1$H NMR (MeOD) δ: 7.89 (s, 1H), 7.82 (d, J=4 Hz, 2H), 7.61 (d, J=8 Hz, 1H), 7.45-7.43 (m, 2H), 7.26 (d, J=8 Hz, 1H), 6.86 (s, 1H), 6.66 (d, J=8 Hz, 1H), 5.28-5.20 (m, 2H), 4.25-4.22 (m, 2H), 4.13-4.10 (m, 2H), 3.90-3.84 (m, 2H), 3.67 (s, 6H), 2.58-2.55 (m, 2H), 2.28-2.06 (m, 8H), 0.96-0.91 (m, 12H). MS (ESI) m/z (M+H)$^+$: 792.

The following compound of the present invention was made using the methods above, and substituting the appropriate reactants and/or reagents.

| Compound No. | LCMS (M + 1) |
|---|---|
| 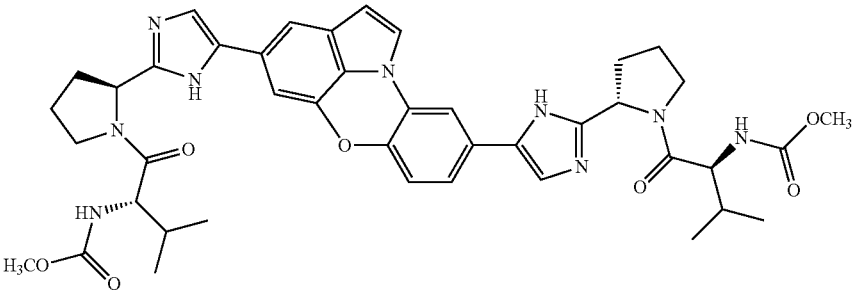 [SMILES: COC(=O)N[C@H](C(=O)N1CCC[C@H]1c1ncc(-c2ccc3c(c2)-n2ccc4cc(-c5cnc([C@@H]6CCCN6C(=O)[C@@H](NC(=O)OC)C(C)C)[nH]5)cc(c42)O3)[nH]1)C(C)C] 16 | 792.9 |

Example 10

Preparation of Methyl [(2S)-1-{(2S)-2-[5-(3-(2-[(2S)-1-(2S)-2-[(methoxycarbonyl)amino]-3,3-dimethylbutanoyl}pyrrolidin-2-yl]-1H-imidazol-5-yl pyrrolo[3,2,1-kl]phenoxazin-8-yl)-1H-imidazol-2-yl] pyrrolidin-1-yl)-3,3-dimethyl-1-oxobutan-2-yl]carbamate (Compound 2)

Compound Int-9j (100 mg, 0.2 mmol) and Compound Int-3a (76 mg, 0.4 mmol) were reacted according to the method described in Example 9, Step K to provide compound 2 (65 mg, 57%). $^1$H NMR (MeOD) δ: 7.87-7.78 (m, 3H), 7.59-7.57 (d, J=8.4 Hz, 1H), 7.43-7.41 (d, J=7.6 Hz, 2H), 7.24-7.22 (d, J=8 Hz, 1H), 6.84 (s, 1H), 6.64-6.62 (d, J=8 Hz, 1H), 5.22-5.19 (m, 2H), 4.30-4.29 (m, 2H), 4.13-4.11 (m, 2H), 3.85-3.84 (m, 2H), 3.67 (s, 6H), 2.55-2.53 (m, 2H), 2.27 (m, 2H), 2.19-2.12 (m, 4H), 0.98 (m, 18H). MS (ESI) m/z (M+H)$^+$: 821.

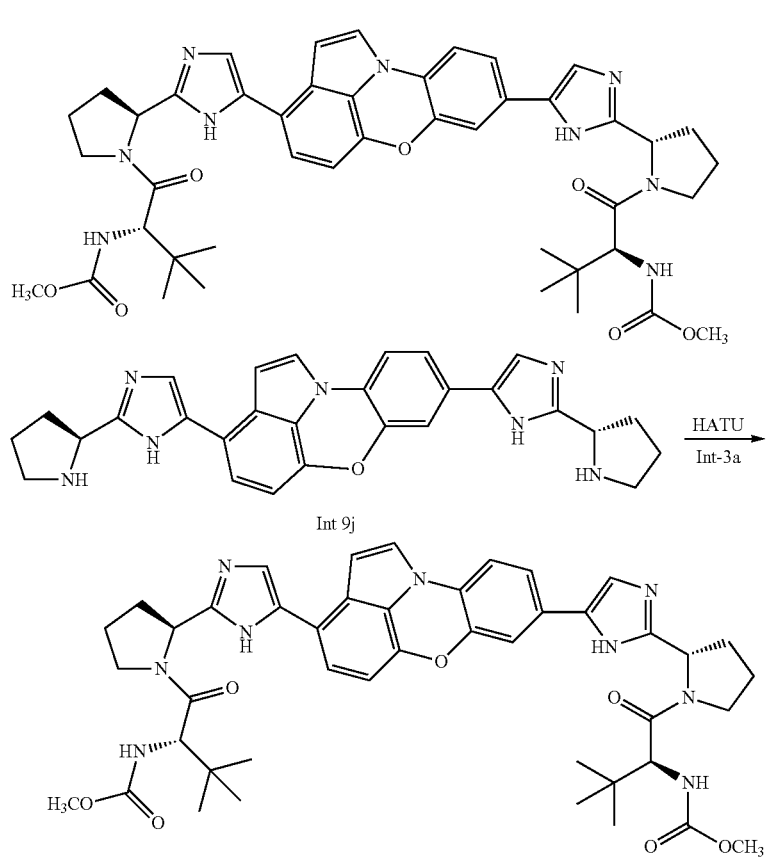

2

Example 11

Preparation of Dimethyl (pyrrolo[3,2,1-kl]phenoxazine-3,8-diylbis{1H-imidazole-5,2-diyl(2S) pyrrolidine-2,1-diyl[(1R)-2-oxo-1-phenylethane-2,1-diyl]}) biscarbamate (Compound 3)

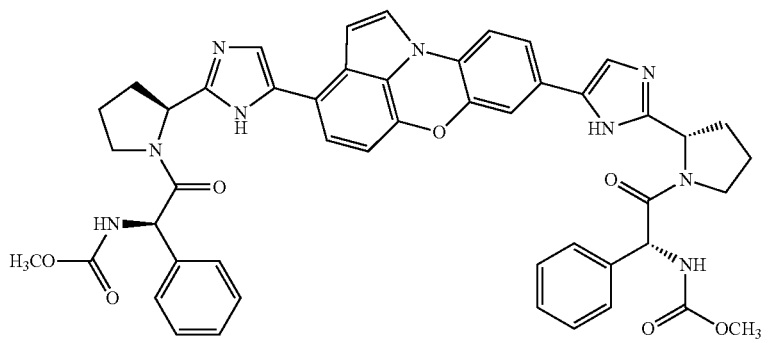

3

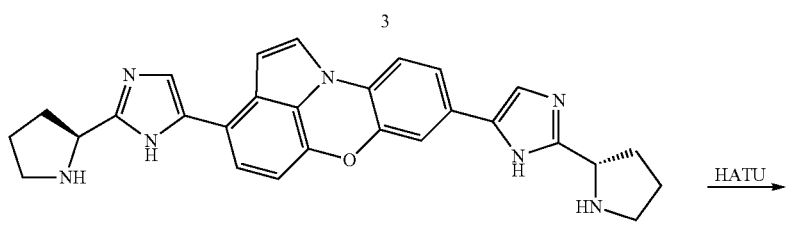

Int 9j

HATU →

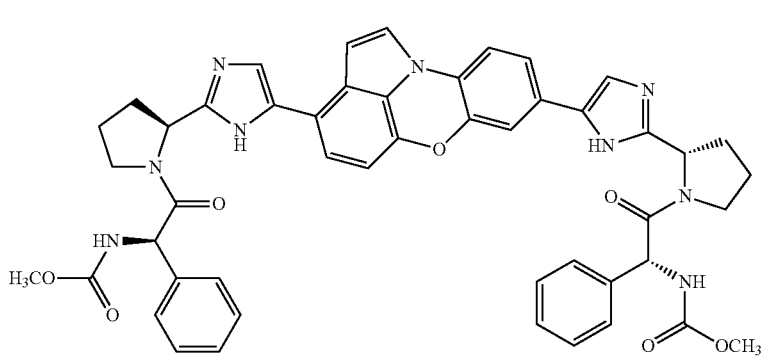

3

To a mixture of compound Int-9j (100 mg, 0.2 mmol), Int-2a (84 mg, 0.4 mmol) and DIPEA (155 mg, 1.2 mmol) in CH$_3$CN (5 mL) was added HATU (152 mg, 0.4 mmol). The resulting mixture was allowed to stir at room temperature for 5 hours. The mixture was filtered and the filtrate was purified using reverse phase HPLC to provide compound 3 (30 mg, 25%). $^1$H NMR (MeOD) δ: 7.92 (s, 1H), 7.82 (d, J=4.4 Hz, 1H), 7.64-7.62 (d, J=8.4 Hz, 1H), 7.53-7.35 (m, 13H), 7.15 (m, 1H), 6.91 (s, 1H), 6.69-6.67 (d, J=8 Hz, 1H), 5.53-5.52 (m, 2H), 5.35-5.29 (m, 2H), 4.82 (m, 2H), 4.15-4.07 (m, 2H), 3.71-3.67 (m, 6H), 3.67 (s, 6H), 2.43 (m, 2H), 2.19-2.03 (m, 4H), 2.03-2.01 (m, 2H). MS (ESI) m/z (M+H)$^+$: 860.

Example 12

Preparation of Dimethyl (pyrrolo[3,2,1-kl]phenoxazine-3,8-diylbis{1H-imidazole-5,2-diyl(2S)-pyrrolidine-2,1-diyl[(1S)-1-cyclopropyl-2-oxoethane-2,1-diyl]})biscarbamate (Compound 4)

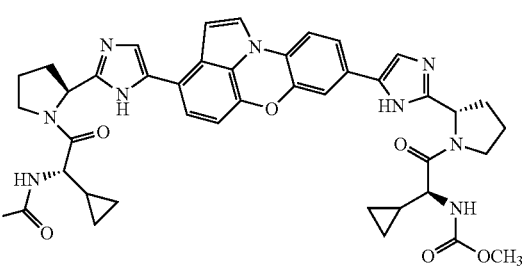

4

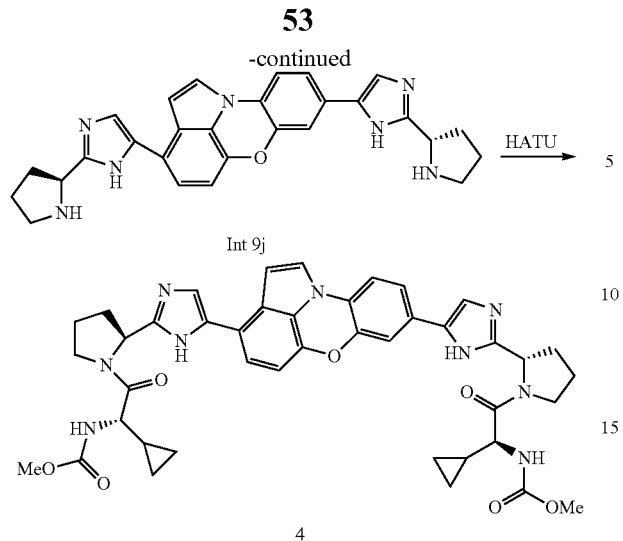

Int 9j

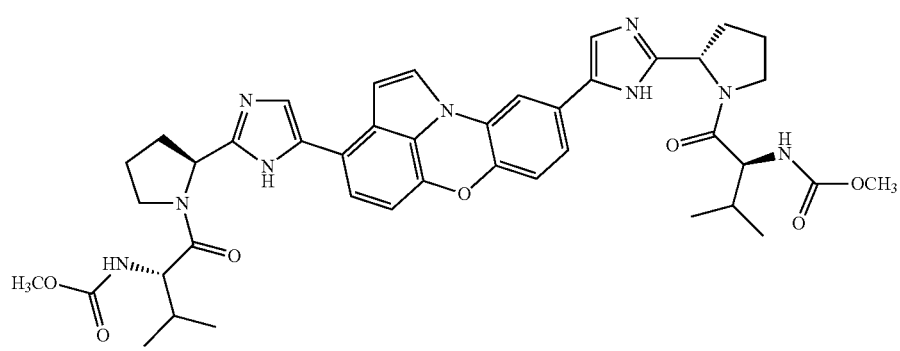

4

Compound 4 was made from Compound Int-9j using the method described in Example 11 and substituting compound Int-3b for compound Int-2a (32 mg, 30% yield). ¹H NMR (MeOD) δ: 7.87-7.77 (m, 3H), 7.57-7.54 (d, J=12.8 Hz, 1H), 7.43-7.41 (d, J=8.4 Hz, 2H), 7.26-7.24 (d, J=8 Hz, 1H), 6.82 (s, 1H), 6.62-6.60 (d, J=8 Hz, 1H), 5.53-5.52 (m, 2H), 5.27-5.21 (m, 2H), 4.01 (m, 2H), 3.83-3.79 (m, 4H), 3.71-3.67 (m, 6H), 2.55-2.52 (m, 2H), 2.21-2.20 (m, 2H), 2.18-2.15 (m, 4H), 1.13-1.09 (m, 2H), 0.60-0.57 (m, 4H), 0.55-0.49 (m, 4H). MS (ESI) m/z (M+H)⁺: 788.

Example 13

Preparation of Methyl [(2S)-1-{(2S)-2-[5-(3-{2-[(2S)-1-{(2S)-2-[(methoxycarbonyl)amino]-3-methyl-butanoyl}pyrrolidin-2-yl]-1H-imidazol-5-yl}pyrrolo[3,2,1-kl]phenoxazin-9-yl)-1H-imidazol-2-yl]pyrrolidin-1-yl}-3-methyl-1-oxobutan-2-yl]carbamate (Compound 5)

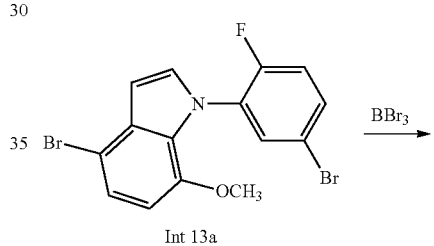

5

Step A—Synthesis of Compound Int-13a

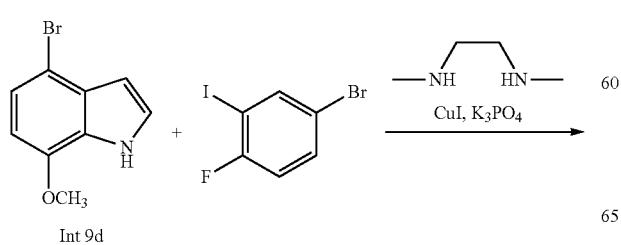

Int 9d

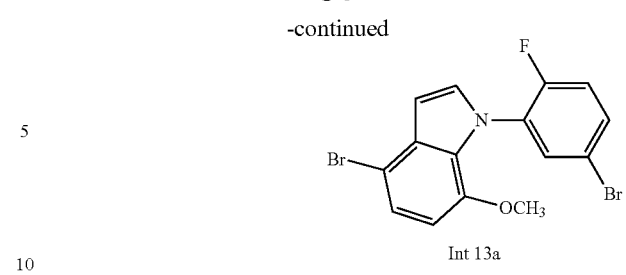

Int 13a

A suspension of compound Int-9d (5 g, 22.1 mmol), 4-bromo-1-fluoro-2-iodobenzene (6.6 g, 22.1 mmol), N,N'-dimethyl ethylenediamine (389 mg, 4.4 mmol), CuI (168 mg, 0.9 mmol) and K₃PO₄ (9.4 g, 44.2 mmol) in dioxane (150 mL) was heated to reflux and allowed to stir at this temperature for 48 hours under N₂ atmosphere. The reaction mixture was then cooled to room temperature and filtered. The filtrated was washed with water (50 mL), extracted with EtOAc (200 mL) and the organic extract was washed with brine, dried over anhydrous sodium sulfate, filtered and concentrated in vacuo. The residue obtained was purified using column chromatography to provide compound Int-13a (3.7 g, 36%). MS (ESI) m/z (M+H)⁺: 400.

Step B—Synthesis of Compound Int-13h

Int 13a

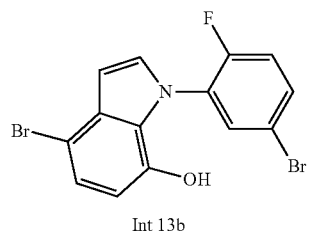

Int 13b

To a solution of compound Int-13a (2 g, 5 mmol) in dichloromethane (50 mL) was added a solution of BBr₃ (2.5 mL, 25 mmol) in dichloromethane and the resulting suspension was allowed to stir at room temperature for about 15 hours. The reaction mixture was then was added to a solution of saturated NaHCO₃ and extracted with dichloromethane. The organic extract was dried over sodium sulfate, filtered and concentrated in vacuo to provide compound Int-13b (1.76 g, 52%) which was used without further purification. MS (ESI) m/z (M+H)⁺: 386.

Step C—Synthesis of Compound Int-13c

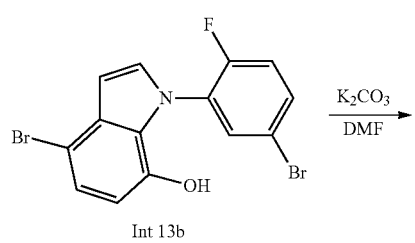

Int 13b

A suspension of compound Int-13b (1.76 g, 4.57 mmol) and K₂CO₃ (1.26 g, 9.14 mmol) in DMF (20 mL) was the reaction mixture was heated to reflux and allowed to stir at this temperature for 2 hours under N₂ atmosphere. The reaction mixture was cooled to room temperature and filtered and the filtrate was washed with water (50 mL) and extracted with EtOAc (100 mL). The organic extract was washed with brine, dried over anhydrous sodium sulfate, filtered and concentrated in vacuo. The residue obtained was purified using column chromatography to provide compound Int-13c (1.6 g, 84%). MS (ESI) m/z (M+H)⁺: 366.

Step D—Synthesis of Compound Int-13d

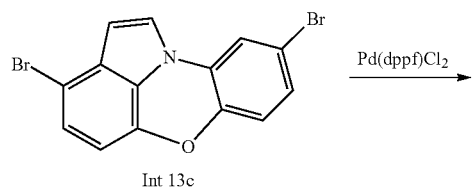

Int 13c

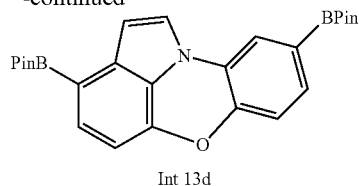

Int 13d

To a solution of compound Int-13c (300 mg, 0.8 mmol) in 1,4-dioxane was added bis(pinacolato)diboron (417 mg, 1.6 mmol), Pd(dppf)Cl₂ (58 mg, 0.08 mmol) and KOAc (203 mg, 2 mmol). The reaction was put under N₂ atmosphere, heated to 110° C. and allowed to stir at this temperature for about 15 hours. The mixture was cooled to room temperature, then concentrated in vacuo. The residue obtained was purified using column chromatography with silica gel to provide compound Int-13d (200 mg, 55%). MS (ESI) m/z (M+H)⁺: 460.

Step E—Synthesis of Compound Int-13e

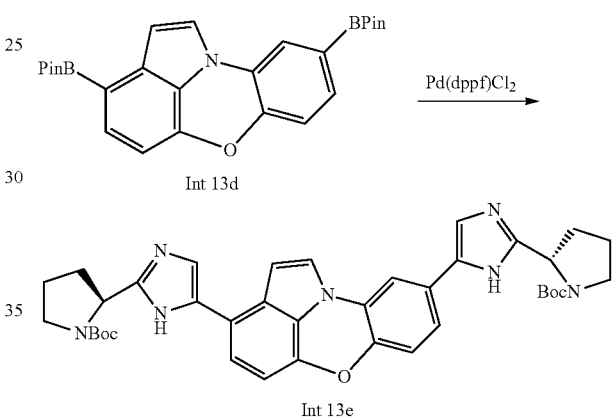

Int 13d

Int 13e

A suspension of compound Int-13d (200 mg, 0.43 mmol), Int-4h (271 mg, 0.86 mmol), Pd(dppf)Cl₂ (58 mg, 0.08 mmol), Na₂CO₃ (182 mg, 1.72 mmol) and in THF/H₂O (10:1, 15 mL) was heated to reflux and allowed to stir at this temperature for 2 hours under N₂ atmosphere. The reaction mixture was cooled to room temperature and filtered and the filtrate was washed with water (20 mL) and extracted with EtOAc (2×50 mL). The combined organic extracts were washed with brine, dried over anhydrous sodium sulfate, filtered and concentrated in vacuo. The residue obtained was purified using column chromatography to provide compound Int-13e (150 mg, 51%). MS (ESI) m/z (M+H)⁺: 678.

Step F— Synthesis of Compound Int-13f

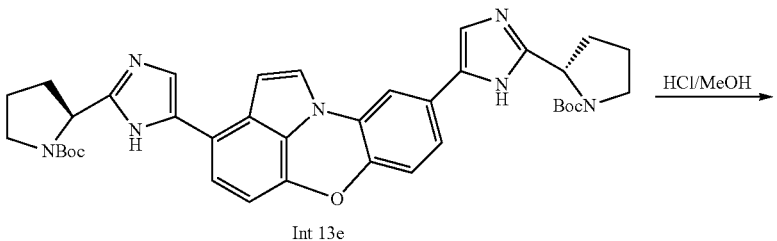

Int 13e

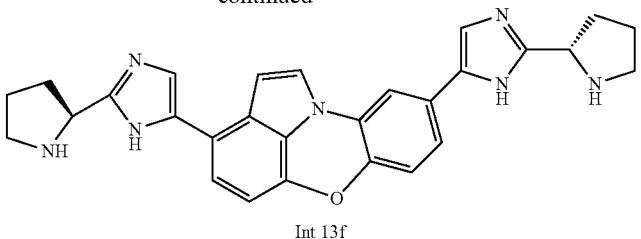

Int 13f

Compound Int-13e (150 mg, 0.22 mmol) was added into HCl/CH₃OH (5 mL). The mixture was allowed to stir at room temperature for 2 hours then concentrated in vacuo to provide compound Int-13f (100 mg, 90%). MS (ESI) m/z (M+H)$^+$: 478.

Step G—Synthesis of Compound 5

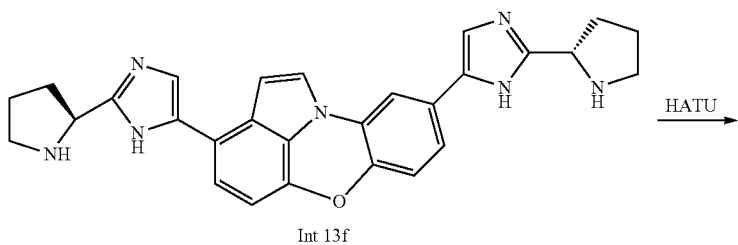

Int 13f

HATU →

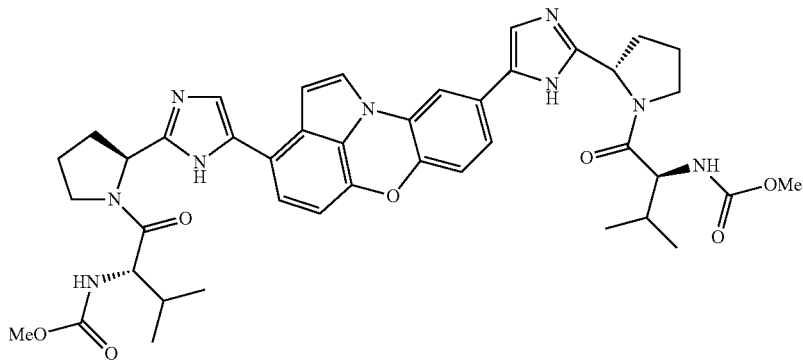

5

To a mixture of compound Int-13f (100 mg, 0.2 mmol), compound Int-1a (70 mg, 0.4 mmol) and DIPEA (155 mg, 1.2 mmol) in CH₃CN (5 mL) was added HATU (152 mg, 0.4 mmol). The resulting mixture was allowed to stir at room temperature for 4 hours and filtered. The filtrate was purified using HPLC to provide compound 5 (70 mg, 59%). $^1$H NMR (MeOD) δ 7.81 (m, 3H), 7.78 (s, 1H), 7.36 (d, J=4 Hz, 1H), 7.21-7.19 (d, J=8 Hz, 1H), 7.14-7.12 (d, J=8.4 Hz, 1H), 6.84 (s, 1H), 6.62-6.60 (d, J=8 Hz, 1H), 5.25-5.20 (m, 2H), 4.23-4.20 (m, 2H), 4.09-4.08 (m, 2H), 387-3.85 (m, 2H), 3.64-3.62 (m, 6H), 2.54-2.53 (m, 2H), 2.26 (m, 2H), 2.18-2.15 (m, 4H), 2.07-2.04 (m, 2H), 0.96-0.87 (m, 12H). MS (ESI) m/z (M+H)$^+$: 792.

Example 14

Preparation of Methyl [(2S)-1-{(2S)-2-[5-(4-{2-[(2S)-1-{(2S)-2-[(methoxycarbonyl)amino]-3-methyl butanoyl}pyrrolidin-2-yl]-1H-imidazol-5-yl}-1,2-dihydropyrrolo[3,2,1-kl]phenoxazin-9-yl)-1H-imidazol-2-yl]pyrrolidin-1-yl}-3-methyl-1-oxobutan-2-yl]carbamate (Compound 6)

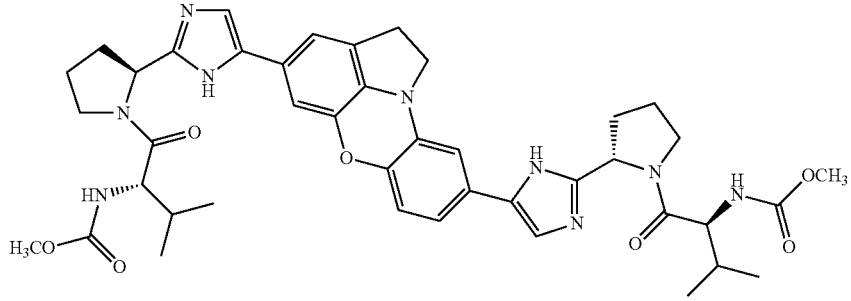

6

Step A—Synthesis of Compound Int-14a

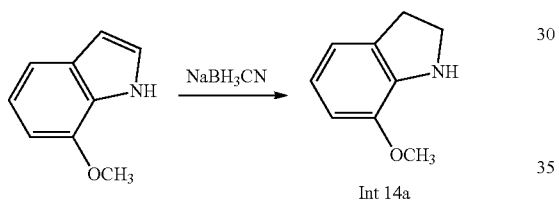

To a 0° C. solution of 7-methoxyindole (50 g; 0.34 mol) in AcOH (200 mL) was added NaBH$_3$CN (17.92 g; 0.51 mol) at a rate to keep the reaction temperature below 5° C. The reaction mixture was then stirred for 1 hour at room temperature, water (0.4 mL) was added, and the resulting solution was concentrated in vacuo. The residue obtained was diluted to 200 mL with EtOAc and the resulting solution was washed with 5% NaHCO$_3$, brine, dried over anhydrous Na$_2$SO$_4$, filtered and concentrated in vacuo to provide compound Int-14a (47 g, 93%). MS (ESI) m/z (M+H)$^+$: 149.

Step B—Synthesis of Compound Int-14b

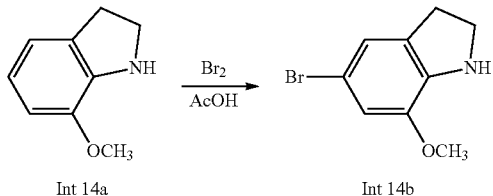

To a mixture of compound Int-14a (47.4 g, 6.33 mol) in AcOH (100 mL) was added a solution of Br$_2$ (32 g, 6.2 mol) in AcOH (100 mL) dropwise at room temperature over 4 hours. The reaction was allowed to stir at room temperature for about 15 hours and the reaction mixture was filtered. The residue obtained was dissolved in water, and basified by NaHCO$_3$ to pH 7~8. The mixture was extracted with EtOAc and the combined organic extracts were concentrated in vacuo and purified using chromatograph (gradient:petroleum ether:EtOAc=50:1, 10:1, 2:1) to afford 14 g crude product which was further purified using HPLC to provide compound Int-14b (4.5 g, 17%). MS (ESI) m/z (M+H)$^+$: 228.

Step C—Synthesis of Compound Int-14c

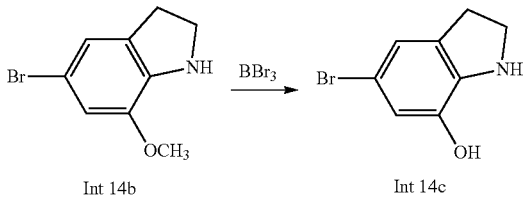

BBr$_3$ (6 mL, 60 mmol) was added dropwise to a solution of compound Int-14b (4.5 g, 19.8 mmol) in dichloromethane at 0° C. and stirred at room temperature for about 15 hours. Ice water was added to quench the reaction and the resulting mixture was extracted twice with dichloromethane. The combined organic extracts were washed with brine, dried over anhydrous Na$_2$SO$_4$, filtered and concentrated in vacuo. The residue obtained was purified using column chromatography on silica to afford product Int-14c (2.4 g, 57%). MS (ESI) m/z (M+H)$^+$:214.

Step D—Synthesis of Compound Int-14d

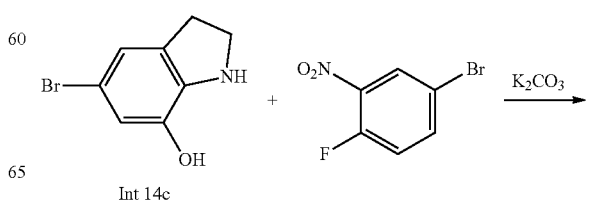

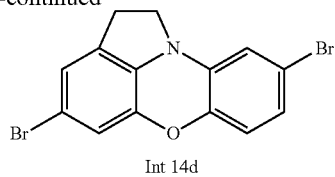

Int 14d

To a mixture of compound Int-14c (500 mg, 2.34 mmol), 2-fluoro-5-bromonitrobenzene (514 mg, 2.34 mmol) and $K_2CO_3$ (969 mg, 7.02 mmol) in DMF (20 mL was allowed to stir at 140° C. for 3 hours. The resulting mixture was concentrated in vacuo and purified using silica gel chromatography (petroleum ether: EtOAc=100:1) to provide compound Int-14d (776 mg, 90%). MS (ESI) m/z (M+H)$^+$: 367.

Step E—Synthesis of Compound Int-14e

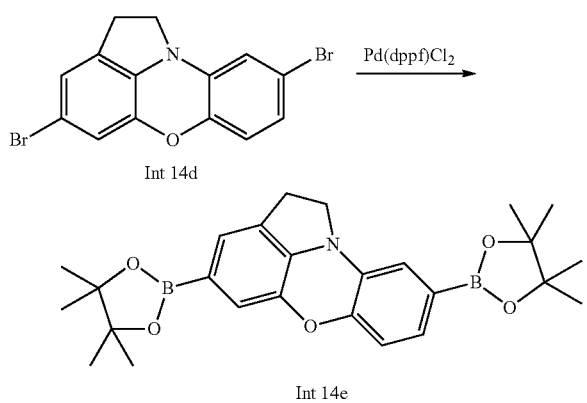

To a solution of compound Int-14d (400 mg, 1.09 mmol) in 1,4-dioxane was added bis(pinacolato)diboron (609 mg, 2.4 mmol) and Pd(dppf)Cl$_2$ (80 mg, 0.1 mmol) and KOAc (320 mg, 3.3 mmol). The reaction mixture was stirred under $N_2$ and heated to 80° C. for 5 hours. The reaction was cooled and concentrated in vacuo and the residue obtained was purified using column chromatography to provide compound Int-14e (270 mg, 53%). MS (ESI) m/z (M+H)$^+$: 461.

Step F—Synthesis of Compound Int-14f

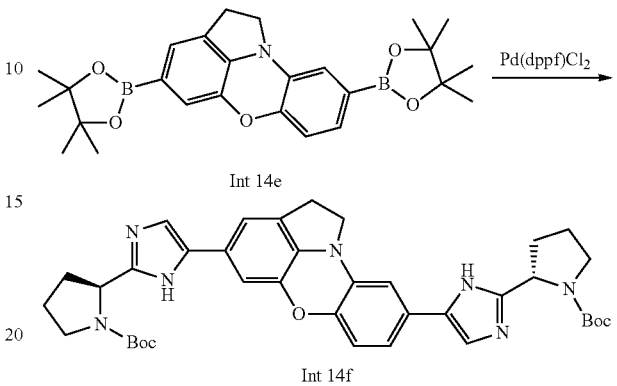

A suspension of compound Int-14e (270 mg, 0.47 mmol), compound Int-4a (300 mg, 0.95 mmol), Pd(dppf)Cl$_2$ (36 mg, 0.05 mmol) and Na$_2$CO$_3$ (159 mg, 1.5 mmol) in THF/H$_2$O (10:1, 35 mL) was heated to reflux and allowed to stir at this temperature for 15 hours under N$_2$ atmosphere. The mixture was cooled and filtered and the filtrate was washed with water (20 mL) and extracted with EtOAc (50 mL). The organic extract was washed with brine, dried over anhydrous sodium sulfate, filtered and concentrated in vacuo. The residue obtained was purified using column chromatography to provide compound Int-14f (127 mg, 39%). MS (ESI) m/z (M+H)$^+$: 680.

Step G—Synthesis of Compound Int-14g

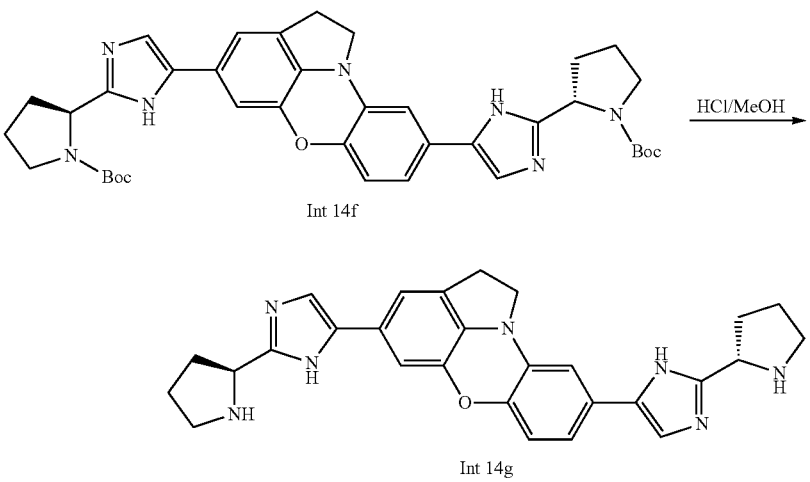 [SMILES: CC(C)(C)OC(=O)N1CCC[C@H]1c1ncc(-c2cc3c4c(c2)Oc2ccc(-c5cnc([C@@H]6CCCN6C(=O)OC(C)(C)C)[nH]5)cc2N4CC3)[nH]1 ; "HCl/MeOH" ; c1cc2c(cc1-c1cnc([C@@H]3CCCN3)[nH]1)N1CCc3cc(-c4cnc([C@@H]5CCCN5)[nH]4)cc(c31)O2]

Compound Int-14f (200 mg, 0.29 mmol) was added into a solution of HCl in CH$_3$OH (10 mL) and the reaction was allowed to stir at room temperature for 2 hours. The mixture was then concentrated in vacuo to provide compound Int-14g (141 mg). MS (ESI) m/z (M+H)$^+$: 480.

Step H—Synthesis of Compound 6

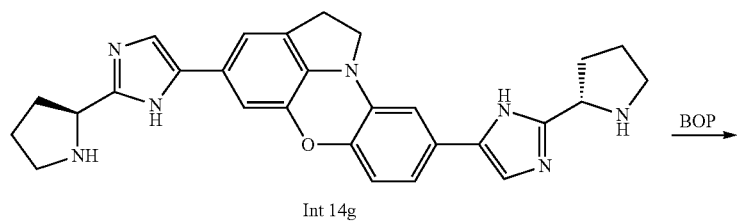

Int 14g

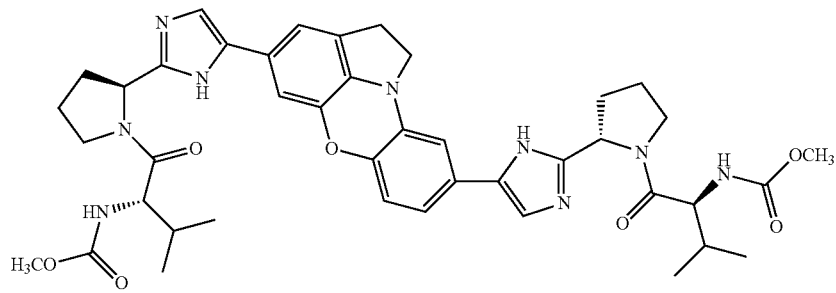

6

To a mixture of compound Int-14g (141 mg, 0.29 mmol), Int-la (105 mg, 0.59 mmol) and DIPEA (2 mmol) in DMF (4 mL) was added BOP reagent (200 mg, 0.59 mmol). The resulting reaction was allowed to stir at room temperature for 5 hours, then was filtered and the filtrate was directly purified using HPLC to provide compound 6 (152 mg, 81%). $^1$H NMR (MeOD) δ: 7.73-7.62 (m, 2H), 7.12-7.02 (m, 2H), 6.88-6.81 (m, 3H), 5.18-5.17 (m, 2H), 4.20-4.19 (m, 2H), 4.08-4.00 (m, 2H), 3.97-3.79 (m, 4H), 3.63 (s, 6H), 2.53-2.49 (m, 2H), 2.28-1.98 (m, 8H), 0.91-0.87 (m, 12H). MS (ESI) m/z (M+H)$^+$: 794.

The following compounds of the present invention were made using the methods above, and substituting the appropriate reactants and/or reagents.

| Compound No. | LCMS (M + 1) |
|---|---|
| 17 | 794.9 |

| Compound No. | LCMS (M + 1) |
|---|---|
| 18 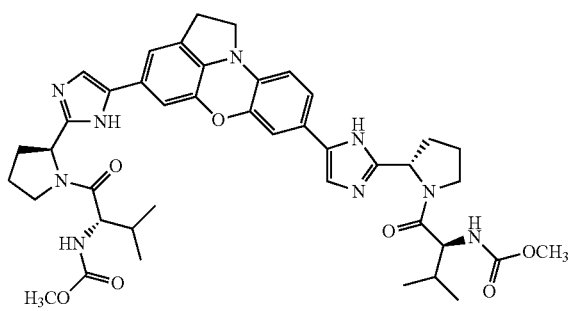 | 866.9 |

Example 15

Preparation of Methyl [(2S)-1-{(2S)-2-[5-(4-{2-[(2S)-1-{(2S)-2-[(methoxycarbonyl)amino]-3-methyl butanoyl}pyrrolidin-2-yl]-1H-imidazol-5-yl}-1,2-dihydropyrrolo[3,2,1-kl]phenoxazin-8-yl)-1H-imidazol-2-yl]pyrrolidin-1-yl}-3-methyl-1-oxobutan-2-yl]carbamate (Compound 7)

7

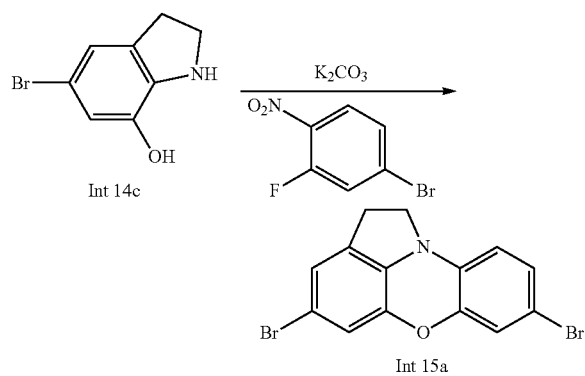

Step A—Synthesis of Compound Int-5a

To a mixture of compound Int-14c (500 mg, 2.34 mmol), 5-bromo-1-fluoro-2-nitrobenzene (514 mg, 2.34 mmol) and K₂CO₃ (969 mg, 7.02 mmol) in 20 mL of dioxane was allowed to stir at 140° C. for 4 hours. The reaction mixture was cooled to room temperature and concentrated in vacuo. The residue obtained was purified using chromatography on silica gel (gradient:petroleum ether:EtOAc=50:1~10:1) to provide compound Int-15a (220 mg, 64%). MS (ESI) m/z (M+H)⁺: 367.

Step B—Synthesis of Compound 7

Int-15a was converted to compound 7 using the methods described in Example 14 Steps E-H. Compound 7: ¹H NMR (MeOD) δ: 7.80-7.62 (On, 2H), 7.41-7.07 (m, 3H), 6.85 (m, 1H), 6.62 (m, 1H), 5.18-5.16 (m, 2H), 4.20-4.18 (m, 2H), 4.08-4.06 (m, 2H), 3.86-3.79 (m, 4H), 3.63 (s, 6H), 2.54-2.53 (m, 2H), 2.24-2.01 (m, 8H), 0.89-0.86 (m, 12H). MS (ESI) m/z (M+H)⁺: 794.

Example 16

Preparation of Methyl [(2S)-1-{(2S)-2-[5-(3-{2-[(2S)-4,4-difluoro-1-{(2S)-2-[(methoxycarbonyl)amino]-3-methylbutanoyl}pyrrolidin-2-yl]-1H-imidazol-5-yl}pyrrolo[3,2,1-kl]phenoxazin-8-yl)-1H-imidazol-2-yl]-4,4-difluoropyrrolidin-1-yl}-3-methyl-1-oxobutan-2-yl]carbamate (Compound 8)

8

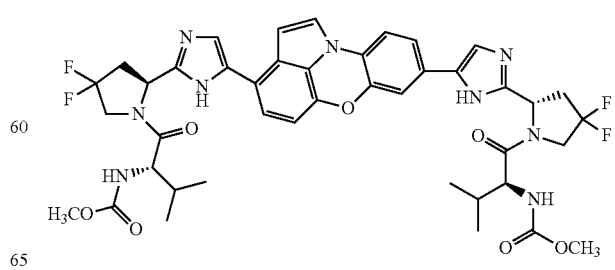

Step A—Synthesis of Compound Int-16a

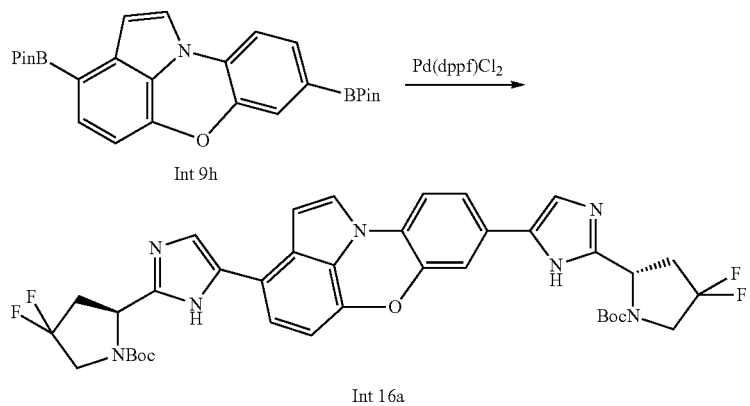

Int 9h

Int 16a

A suspension of compound Int-9h (100 mg, 0.22 mmol), compound Int-6c (138 mg, 0.44 mmol), Pd(dppf)Cl₂ (30 mg, 0.04 mmol) and Na₂CO₃ (93 mg, 0.88 mmol) in THF/H₂O (5:1, 15 mL) was heated to reflux and allowed to stir at this temperature for 15 hours under N₂ atmosphere. The reaction mixture was cooled and filtered and the filtrate was washed with water (20 mL) and extracted with EtOAc (50 mL). The organic extract was washed with brine, dried over anhydrous sodium sulfate, filtered and concentrated in vacuo and the residue obtained was purified using column chromatography to provide compound Int-16a (60 mg, 50%). MS (ESI) m/z (M+H)⁺: 750.

Step B—Synthesis of Compound Int-16b

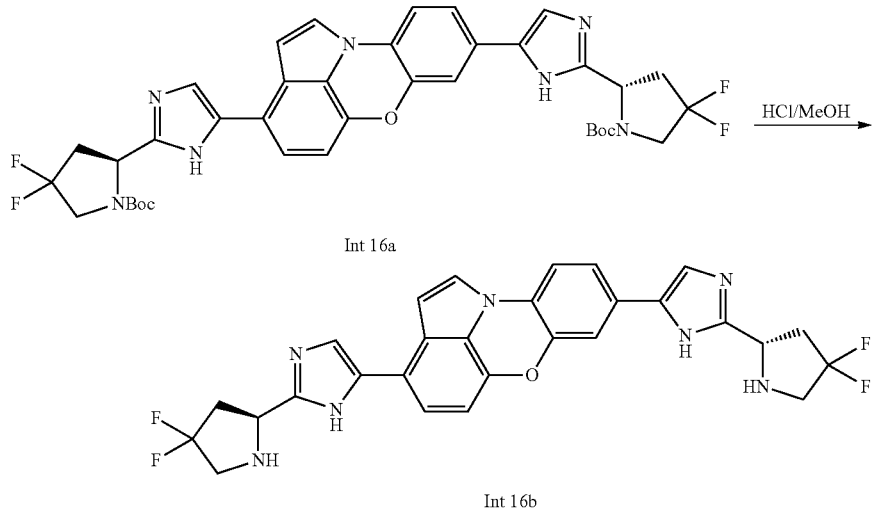

Int 16a

Int 16b

Compound Int-16a (15 mg, 0.02 mmol) was added into HCl/CH₃OH (5 mL) and the mixture was allowed to stir at room temperature for 2 hours. The mixture was concentrated in vacuo to provide compound Int-16b (11 mg, 90%). MS (ESI) m/z (M+H)⁺: 550.

Step C—Synthesis of Compound 8

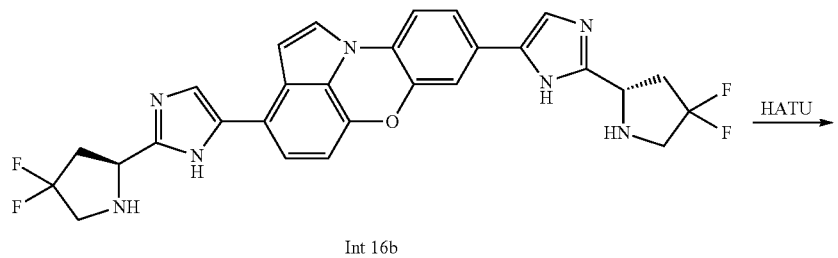

Int 16b

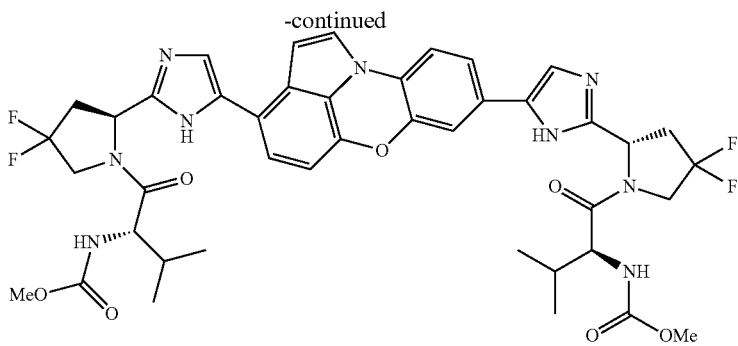

8

To a mixture of compound Int-16b (11 mg, 0.02 mmol), Int-1a (7 mg, 0.04 mmol) and DIPEA (15.5 mg, 0.12 mmol) in CH₃CN (2 mL) was added HATU (15 mg, 0.12 mmol). The resulting mixture was allowed to stir at room temperature for 4 hours then concentrated in vacuo. The residue obtained was purified using HPLC to provide the compound 8 (5 mg, 45%). $^1$H NMR: (MeOD) δ: 7.85 (s, 1H), 7.78 (s, 1H), 7.66 (s, 1H), 7.55-7.53 (d, J=8.4 Hz, 1H), 7.42-7.40 (d, J=6.8 Hz, 2H), 7.24-7.22 (d, J=8 Hz, 1H), 6.83 (s, 1H), 6.63-6.61 (d, J=8 Hz, 1H), 5.50-5.47 (m, 1H), 5.40 (m, 1H), 4.53 (m, 2H), 4.29-4.26 (m, 2H), 4.09-4.05 (t, J=14 Hz, 2H), 3.64 (s, 6H), 3.11 (m, 2H), 2.83-2.78 (m, 2H), 2.01-1.98 (m, 2H), 0.89-0.88 (m, 12H). MS (ESI) m/z (M+H)⁺: 864.

Example 17

Preparation of Methyl [(2S)-1-{(2S,4R)-4-fluoro-2-[5-(3-{2-[(2S,4R)-4-fluoro-1-{(2S)-2-[(methoxycarbonyl)amino]-3-methylbutanoyl}pyrrolidin-2-yl]-1H-imidazol-5-yl}pyrrolo[3,2,1-kl]phenoxazin-8-yl)-1H-imidazol-2-yl]pyrrolidin-1-yl}-3-methyl-1-oxobutan-2-yl]carbamate (Compound 9)

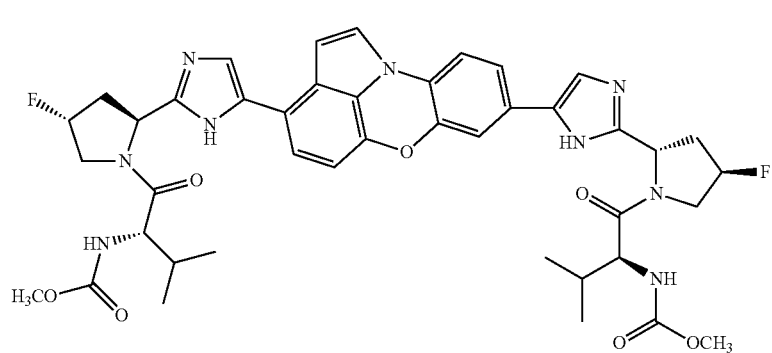

9

Compound 9 was prepared according to the methods described in Example 16 and substituting compound Int-5f for compound Int-6c in step A.

Compound 9: $^1$H NMR (MeOD): δ 7.91 (d, J=3.2 Hz, 1H), 7.90 (s, 1H), 7.72 (s, 1H), 7.62 (d, J=8 Hz, 1H), 7.46-7.45 (m, 2H), 7.2 (d, J=8 Hz, 1H), 6.86 (d, J=4 Hz, 1H), 6.68 (d, J=8 Hz, 1H), 5.65-5.51 (m, 2H), 4.29-4.21 (m, 2H), 4.13-4.09 (m, 2H), 3.68 (s, 6H), 2.86-2.81 (m, 2H), 2.65-2.57 (m, 2H), 2.19-2.13 (m, 2H), 1.01-0.97 (m, 12H). MS (ESI) m/e (M+H)⁺: 828.

Example 18

Preparation of Methyl [(2S)-1-{(2S)-2-[5-(3-{2-[(2S)-1-{(2S)-2-[(methoxycarbonyl)amino]-3-methylbutanoyl}pyrrolidin-2-yl]-1H-imidazol-5-yl}pyrazolo[4,5,1-kl]phenoxazin-8-yl)-1H-imidazol-2-yl]pyrrolidin-1-yl}-3-methyl-1-oxobutan-2-yl]carbamate (Compound 10)

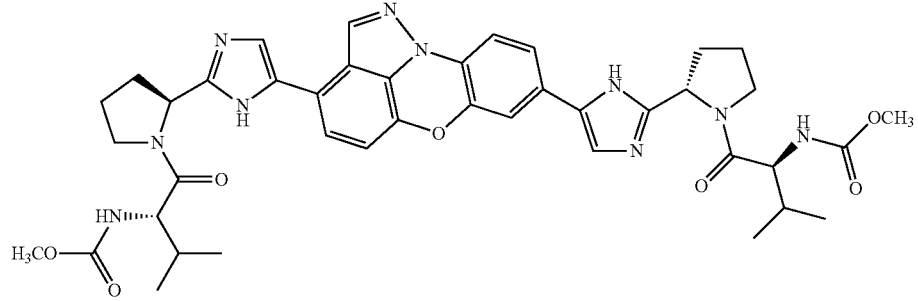

Step A—Synthesis of Compound Int-18a

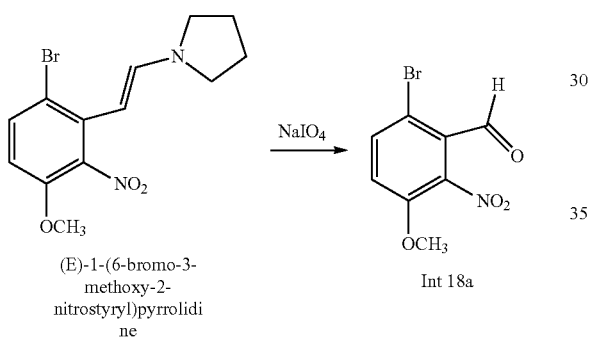

(E)-1-(6-bromo-3-methoxy-2-nitrostyryl)pyrrolidine

Int 18a

To a solution of 16.3 g (50 mmol) of (E)-1-(6-bromo-3-methoxy-2-nitrostyryl)pyrrolidine (prepared as described in US Patent Publication No. US 20070112005) in, THF/water (200 mL/100 mL) was added NaIO$_4$ (42.6 g, 200 mmol) and the reaction was allowed to stir for 16 hours. The reaction mixture was extracted with EtOAc (2×100 mL) and the combined organic extracts were dried over Na$_2$SO$_4$, filtered and concentrated in vacuo and the residue obtained was purified using column chromatography on silica gel to provide compound Int-18a (7.6 g, 60%). $^1$H NMR: (CDCl$_3$) δ: 10.18 (s, 1H), 7.70-7.60 (d, J=8.8 Hz, 1H), 7.14-7.10 (d, J=8.8 Hz, 1H), 3.86 (s, 3H).

Step B—Synthesis of Compound Int-18b

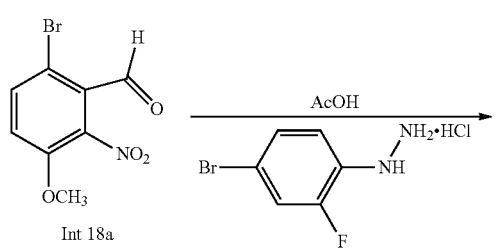

Int 18a

-continued

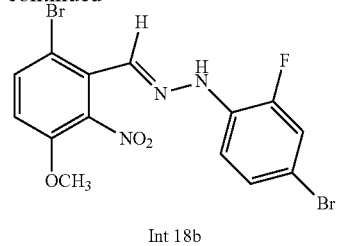

Int 18b

To a suspension of compound Int-18a (5.2 g, 20 mmol) and 4-bromo-2-fluorophenylhydrazide hydrochloride (4.8 g, 20 mmol) in ethanol (15 mL) was added AcOH (5 mL) and the reaction mixture was heated to reflux and allowed to stir at this temperature for 24 hours. The reaction mixture was cooled to room temperature and concentrated in vacuo and the residue obtained was partitioned between EtOAc and water. The organic layer was collected and dried over sodium sulfate then concentrated in vacuo to provide a crude residue which was recrystallized from dichloromethane to provide compound Int-18b (6.2 g, 71%). MS (ESI) m/z (M+H)$^+$: 446, 448 & 450.

Step C—Synthesis of Compound Int-18c

Int 18b

-continued

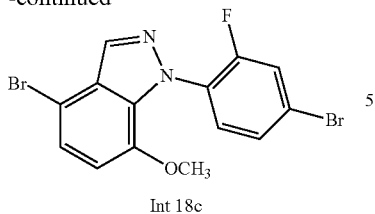
Int 18c

To a suspension of compound Int-18b (6.2 g, 13.9 mmoL) in ethanol (20 mL) was added KOH (2.8 g, 40 mmoL) and the reaction was heated to reflux and allowed to stir at this temperature for about 15 hours. The reaction mixture was cooled to room temperature and partitioned between EtOAc and water. The organic layer was washed with brine, dried over sodium sulfate, filtered and concentrated in vacuo and the residue obtained was purified using column chromatography on silica gel [petroleum ether/EtOAc (200:1~5:1)] to provide compound Int-18c (1.2 g, 21%). MS (ESI) m/z (M+H)$^+$: 399, 401 & 403.

Step D—Synthesis of Compound Int-18d

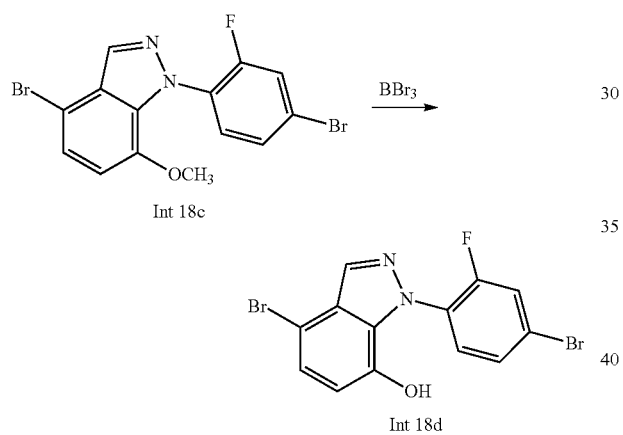

To a solution of compound Int-18c (1.2 g, 3 mmol) in dichloromethane (20 mL) was added BBr$_3$ (3 mL) and the mixture was allowed to stir at room temperature for 20 hours. The reaction was carefully poured into ice and extracted with EtOAc. The extract was washed with brine, dried over sodium sulfate, filtered and concentrated in vacuo to provide compound Int-18d (1.2 g), which was used without further purification. MS (ESI) in/z (M+H)$^+$: 385, 387 & 389.

Step E—Synthesis of Compound Int-18e

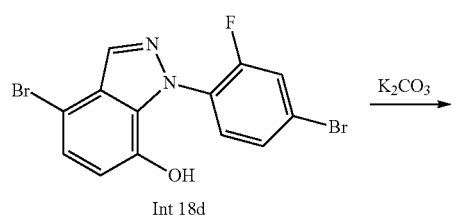

-continued

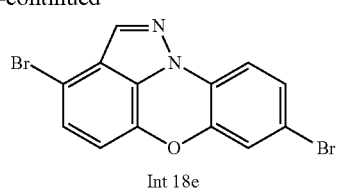
Int 18e

The suspension of compound Int-18d (1.2 g, 3.1 mmol) and K$_2$CO$_3$ (1.38 g, 10 mmol) in DMF (20 mL) was allowed to stir at 120° C. for 1 hour. The reaction mixture was cooled to room temperature then poured into water and the precipitate was collected by filtration. The solid was washed with methanol and then dried to provide compound Int-18e (0.72 g, 67% for two steps). $^1$H NMR: (DMSO) δ: 8.23 (s, 1H), 7.61-7.64 (d, J=8.8 Hz, 1H), 7.54 (s, 1H), 7.42-7.44 (d, J=8.8 Hz, 1H), 7.27-7.29 (d, J=8.8 Hz, 1H), 6.77-6.79 (d, J=8.8 Hz, 1H).

Step F—Synthesis of Compound Int-18f

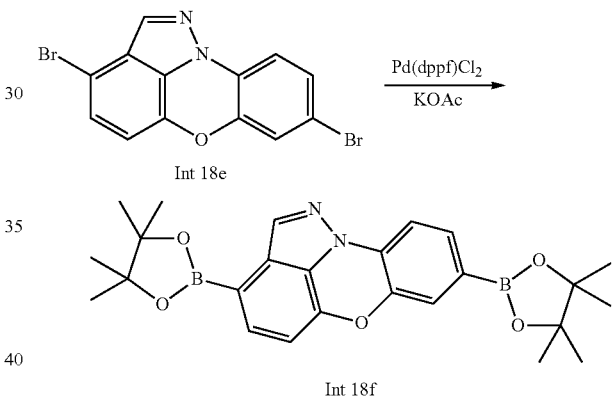

To a solution of compound Int-18e (720 mg, 2 mmol) in 1,4-dioxane was added bis(pinacolato)diboron (1.1 g, 4.4 mmol), Pd(dppf)Cl$_2$ (80 mg) and KOAc (490 mg, 5 mmol). The reaction mixture was degassed, put under N$_2$ atmosphere, then heated to 110° C. allowed to stir at this temperature for about 15 hours. The reaction mixture was cooled to room temperature and concentrated in vacuo and the residue obtained was purified using column chromatography on silica gel to provide compound Int-18f (460 mg, 50%). MS (ESI) m/z (M+H)$^+$: 461.

Step G—Synthesis of Compound Int-18g

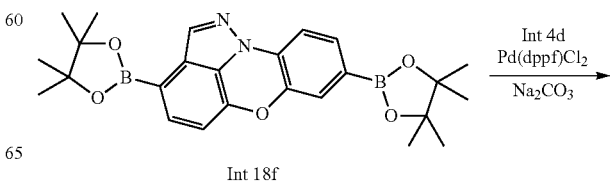

-continued

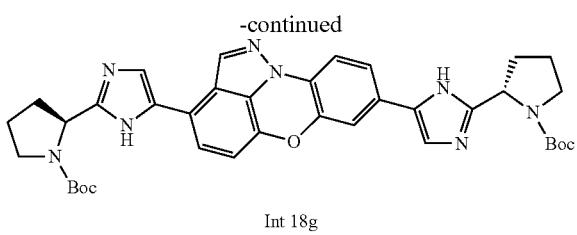

Int 18g

A suspension of compound Int-18f (460 mg, 1 mmol), Int-4d (632 mg, 2 mmol), Pd(dppf)Cl₂ (80 mg) and Na₂CO₃ (424 mg, 4 mmol) in THF/H₂O (5:1, 15 mL) was heated to reflux and allowed to stir at this temperature for 15 hours under N₂ atmosphere. The reaction mixture was cooled to room temperature and partitioned between EtOAc and water and the organic layer was separated, washed with brine, dried over sodium sulfate, filtered and concentrated in vacuo. The residue obtained was purified using column chromatography on silica gel to provide compound Int-18g (150 mg, 25%). MS (ESI) m/z (M+H)⁺: 679.

Step H—Synthesis of Compound Int-18h

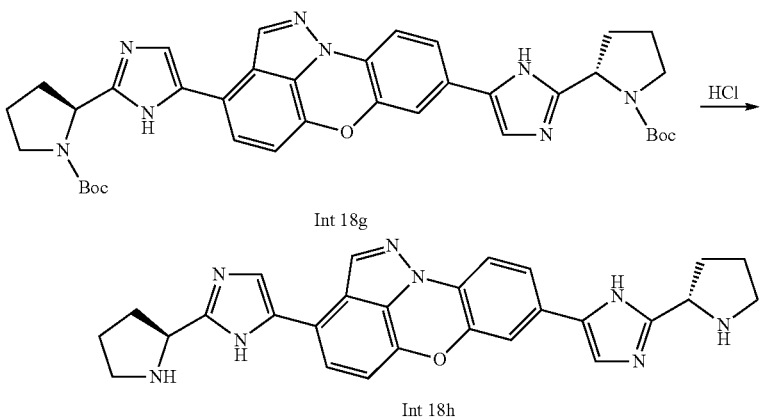

Compound Int-18g (150 mg, 0.22 mmol) was added to HCl/CH₃OH (5 mL) and the mixture was allowed to stir at room temperature for 2 hours. The reaction mixture was then concentrated in vacuo to provide compound Int-18h (150 mg), which was used without further purification. MS (ESI) m/z (M+H)⁺: 479.

Step I—Synthesis of Compound 10

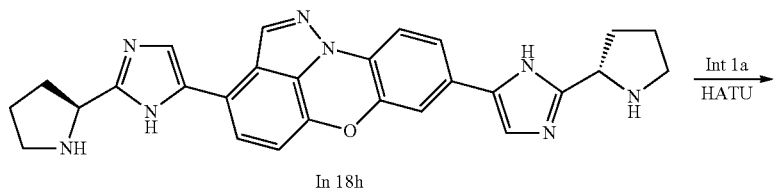

In 18h

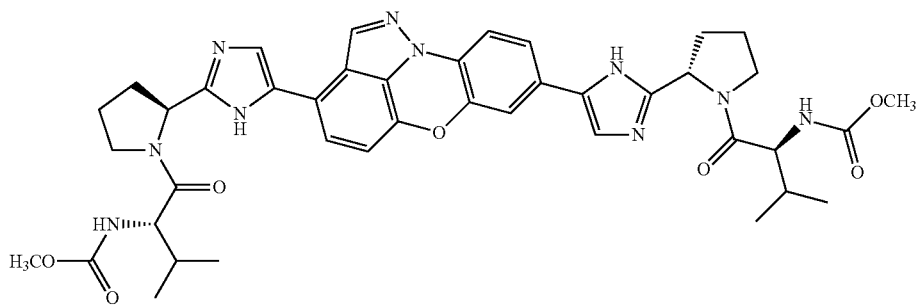

10

To a mixture of compound Int-18h (150 mg, 0.23 mmol), Int-la (81 mg, 0.46 mmol) and DIPEA (155 mg, 1.2 mmol) in CH₃CN (5 mL) was added HATU (175 mg, 0.46 mmol). The resulting reaction was allowed to stir at room temperature for 4 hours, then was filtered. The filtrate was concentrated and the residue was purified using HPLC to provide compound 10 (40 mg, 32% yield). $^1$H NMR: (MeOD) δ: 8.25 (s, 1H), 7.62-7.90 (m, 3H), 7.20-7.48 (m, 3H), 6.70 (s, 1H), 5.10-5.20 (m, 2H), 3.92-4.20 (m, 4H), 3.70-3.88 (m, 2H), 3.56 (s, 6H), 2.38-2.56 (m, 2H), 1.88-2.22 (m, 8H), 0.70-0.92 (m, 12H). MS (ESI) m/z (M+H)$^+$: 793.

Example 19

Preparation of Methyl [(2S)-1-{(2S)-2-[5-(5-{2-[(2S)-1-{(2S)-2-[(methoxycarbonyl)amino]-3-methyl butanoyl}pyrrolidin-2-yl]-1H-imidazol-5-yl}-2,3-dihydro-1H-pyrido[3,2,1-kl]phenoxazin-9-yl)-1H-imidazol-2-yl]pyrrolidin-1-yl}-3-methy-1-oxobutan-2-yl]carbamate (Compound 11)

Step B—Synthesis of Compound Int-19b

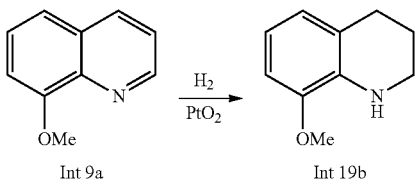

A solution of compound Int-19a (21 g, 0.132 mol) and PtO₂ (2 g, 5 mol %) in 80 mL of MeOH was allowed to stir at room temperature for 4 hours under a H₂ atmosphere (40 psi). The reaction mixture was filtered and the filtrate was concentrated in vacuo to provide compound Int-19b as yellow oil (18 g, 84%). $^1$H NMR: (CDCl₃) δ 6.57-6.64 (m, 3H), 4.25 (br, 1H), 3.84 (s, 3H), 3.35 (s, 2H), 2.79-2.80 (m, 2H), 1.96-1.99 (m, 2H).

11

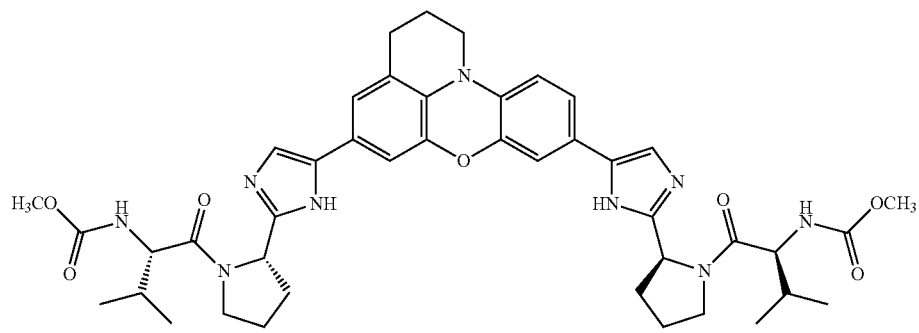

Step A—Synthesis of Compound Int-19a

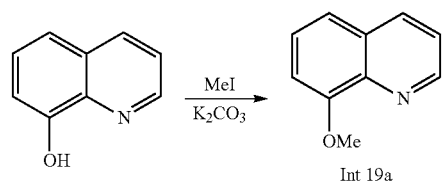

A solution of 8-hydroxyquinoline (25 g, 0.172 mol), KOH (38.5 g, 0.69 mol) and MeI (16.1 mL, 0.26 mol) in THF/DMF (300 mL/50 mL) was allowed to stir for 12 hours at room temperature. 100 mL of water was added and the mixture was concentrated in vacuo to remove THF. The resulting aqueous solution was extracted with EtOAc, and the organic extract was washed with brine, dried over Na₂SO₄, filtered and concentrated in vacuo. The residue obtained was purified using flash chromatography on silica gel (petroleum ether: EtOAc=5:1) to provide compound Int-19a as yellow oil (23 g, 84%), $^1$H NMR: (CDCl₃) δ 8.87 (s, 1H), 8.07 (d, J=7.2 Hz, 1H), 7.33-7.41 (m, 3H), 7.00 (d, 0.1=6.0 Hz, 1H), 4.04 (s, 3H).

Step C—Synthesis of Compound Int-19c

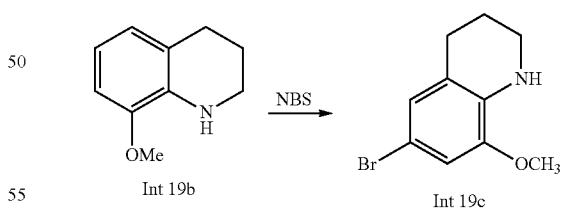

To a solution of compound Int-19b (17 g, 0.104 mol) in THF/DMF (200 mL/100 mL) at −30° C. was added NBS (20 g, 0.115 mol) in portions and the mixture was allowed to stir at −30° C. for 1 hour. The mixture was diluted with water and EtOAc and the water layer was extracted with EtOAc. The organic extract was washed with brine, dried over Na₂SO₄, filtered and concentrated in vacuo to provide a residue which was purified using flash chromatography on silica gel (petroleum ether:EtOAc=10:1) to provide compound Int-19c as yellow oil (20g, 79%).

Step D—Synthesis of Compound Int-19d

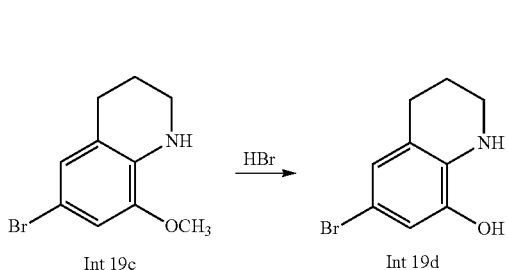 [SMILES: COc1cc(Br)cc2c1NCCC2 ; Br ; Oc1cc(Br)cc2c1NCCC2]

A solution of compound Int-19c (4.84 g, 20 mmol) in 100 mL of 40% aq. HBr was allowed to stir at 100° C. for 12 hours. The mixture was cooled and neutralized with aq. NaOH and excess saturated $Na_2CO_3$ solution. The resulting neutral solution was extracted with EtOAc and the organic extract was washed with brine, dried over $Na_2SO_4$, filtered and concentrated in vacuo to provide compound Int-19d (3.8 g, 83%).

Step E—Synthesis of Compound Int-19e

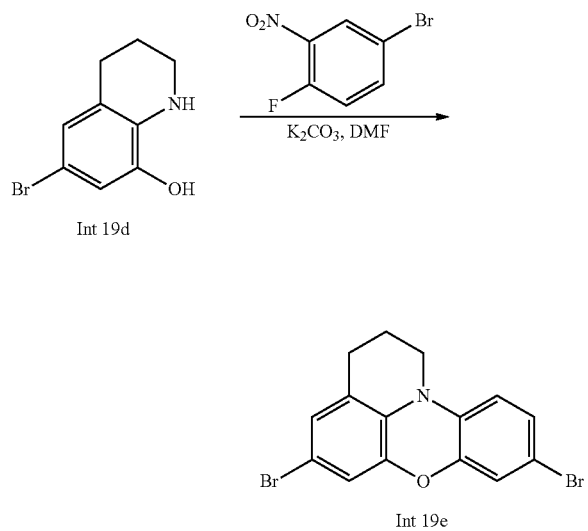

A solution of compound Int-19d (0.125 g, 0.55 mmol), 5-bromo-2-fluoronitrobenzene (0.109 g, 0.5 mmol) and $K_2CO_3$ (0138 g, 1 mmol) in 5 mL of DMF was heated to 120° C. and allowed to stir at this temperature for 3 hours. The reaction mixture was cooled and diluted with EtOAc then washed with water (5×) and brine. The mixture was dried over $Na_2SO_4$, filtered and concentrated in vacuo and the resulting residue was purified using flash chromatography on silica gel (petroleum ether: EtOAc=10:1) to provide compound Int-19e as yellow solid (0.124 g, 65%). $^1H$ NMR: ($CDCl_3$) δ 6.89 (d, J=6.0 Hz, 1H), 6.73 (s, 1H), 6.68 (s, 1H), 6.60 (s, 1H), 6.25 (d, J=8.4 Hz, 1H), 3.19-3.22 (m, 2H), 2.58-2.61 (m, 2H), 2.01-2.05 (m, 2H).

Step F—Synthesis of Compound Int-19f

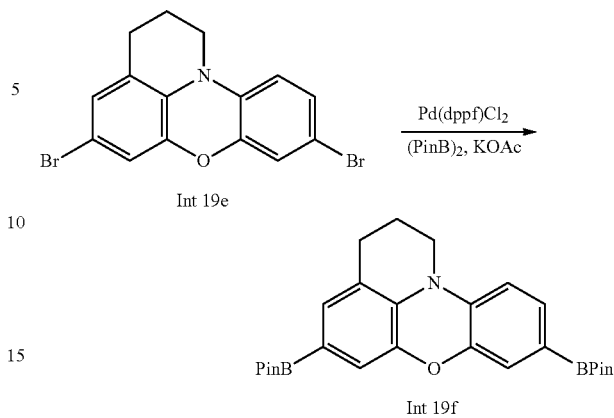

A solution of compound Int-19e (0.3 g, 0.79 mmol), bis(pinacolato) diboron (0.508 g, 2.0 mmol), Pd(dppf)Cl$_2$ (0.115 g, 0.158 mmol) and KOAc (0.232 g, 2.4 mmol) in 5 mL of 1,4-dioxane was heated to 80° C. and allowed to stir at this temperature for 2 hours, under $N_2$ atmosphere. The reaction mixture was cooled to room temperature, diluted with EtOAc, washed with water and brine, dried over $Na_2SO_4$, filtered and concentrated in vacuo. The residue obtained was purified using flash chromatography on silica gel (petroleum ether: EtOAc=10:1) to provide compound Int-19f as yellow solid (150 mg, 40%). $^1H$ NMR: ($CDCl_3$) δ 7.24 (d, J 6.8 Hz, 1H), 7.00 (s, 2H), 6.87 (s, 1H), 6.42 (d, J=8.8 Hz, 1H), 3.30 (t, J=5.6 Hz, 2H), 2.61-2.64 (m, 2H), 2.02-2.03 (m, 2H), 1.29 (s, 12).

Step G—Synthesis of Compound Int-19g

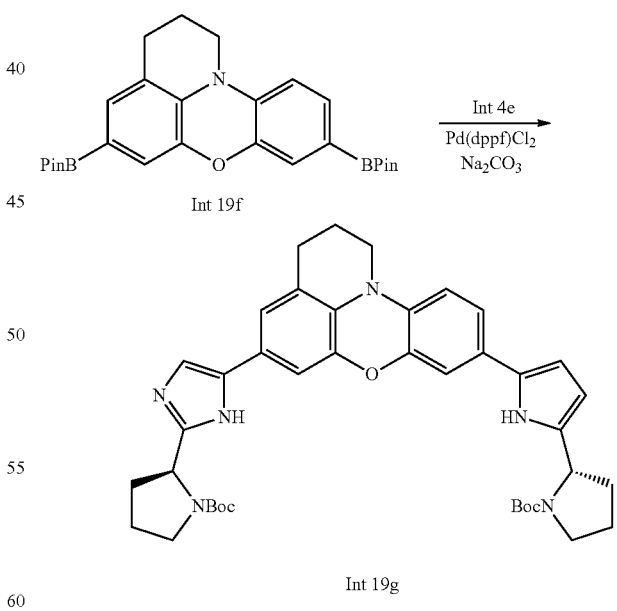

A solution of compound Int-19f (0.475 g, 1.00 mmol), compound Int 4e (0.7 g, 2.2 mmol), Pd(dppf)Cl$_2$ (0.146g, 0.2 mmol) and $Na_2CO_3$ (0.424 g, 4 mmol) in THF/$H_2O$ (25 mL/5 mL) was heated to 80° C. and allowed to stir at this temperature for 12 hours under $N_2$ atmosphere. The reaction mixture was cooled to room temperature and extracted with EtOAc and the organic extract was washed with water and brine, dried over Na$_2$SO$_4$, filtered and concentrated in vacuo. The residue obtained was purified using flash chromatography on silica gel (petroleum ether: EtOAc (gradient)=5:1 to 1:5) to provide compound Int-19g (0.130 g, 19%). MS (ESI) m/z (M+H)$^+$: 693

Step H—Synthesis of Compound Int-19h

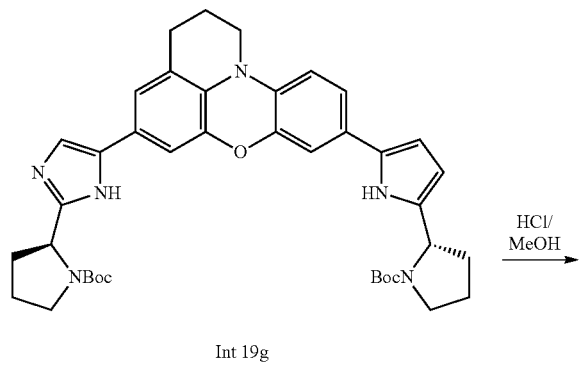

Int 19g

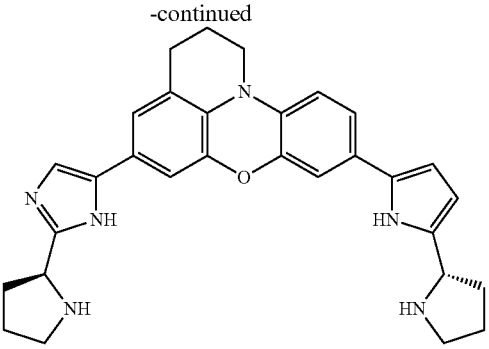

Int 19h

A solution of compound Int-19g (130 mg, 0.19 mmol) in 2 mL of HCl/MeOH was allowed to stir at room temperature for 0.5 hours. The reaction mixture was then concentrated in vacuo to provide compound Int-19h (90 mg, 96%) which was used in the next step without further purification.

Step I—Synthesis of Compound 11

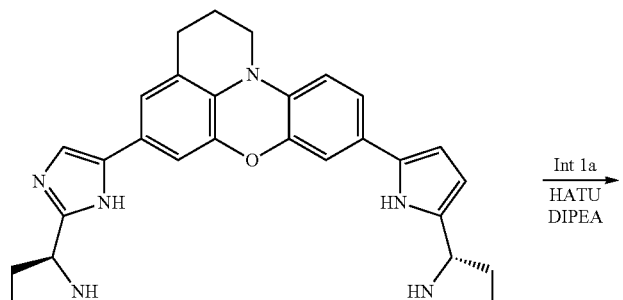

Int 19h

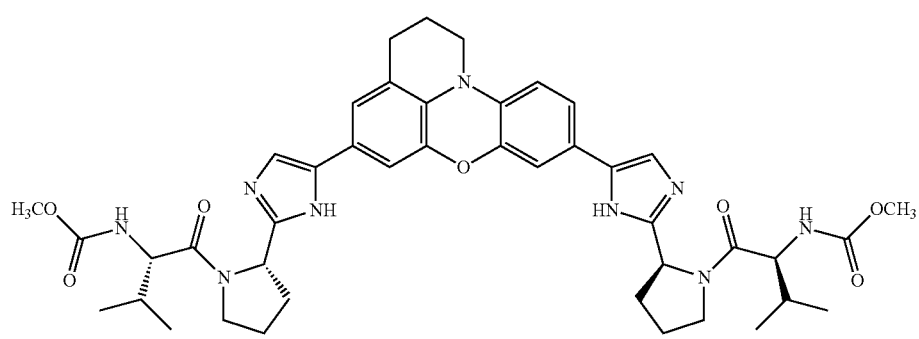

11

A solution of compound Int-19h (90 mg, 0.18 mmol), Int-1a (63 mg, 0.36 mmol), HATU (137 mg, 0.36 mmol) and i-Pr₂NEt (232 mg, 1.8 mmol) in 2 mL of CH₃CN was allowed to stir at room temperature for about 15 hours. The reaction mixture was concentrated in vacuo and 2 mL of DMF was added to dissolve the resulting residue. The solution obtained was purified using HPLC to provide compound 11 as yellow solid (30 mg, 21%). ¹H NMR: (CD₃OD) δ 7.67 (d, J=8.4 Hz, 2H), 7.22 (d, J=7.6 Hz, 1H), 7.01 (d, J=4.4 Hz, 2H), 6.88 (s, 1H), 6.76 (d, J=8.4 Hz, 1H), 5.19 (s, 2H), 4.21 (d, J=7.2 Hz, 2H), 4.10 (s, 2H), 3.81-3.87 (m, 2H), 3.66 (s, 6H), 3.45 (s, 2H), 2.76 (s, 2H), 2.51-2.57 (m, 2H), 2.25-2.26 (m, 2H), 2.13-2.19 (m, 6H), 2.00-2.07 (m, 2H), 0.90-0.97 (m, 12H). MS (ESI) m/z (M/2+H)⁺: 404.8.

The following compounds of the present invention were made using the methods above, and substituting the appropriate reactants and/or reagents.

Example 20

Preparation of Methyl [(2S)-1-{(2S)-2-[5-(5-{2-[(2S)-1-{(2S)-2-[(methoxycarbonyl)amino]-3-methylbutanoyl}pyrrolidin-2-yl]-1H-imidazol-5-yl}-2,3-dihydro-1H-pyrido[3,2,1-kl]phenoxazin-10-yl)-1H-imidazol-2-yl]pyrrolidin-1-yl}-3-methyl-1-oxobutan-2-yl]carbamate (Compound 12)

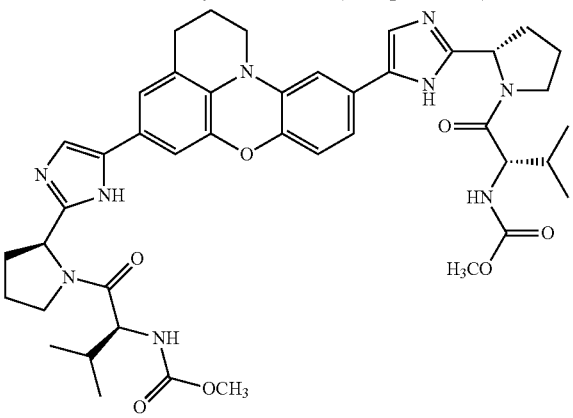

| Compound No. | LCMS (M + 1) |
|---|---|
| 19 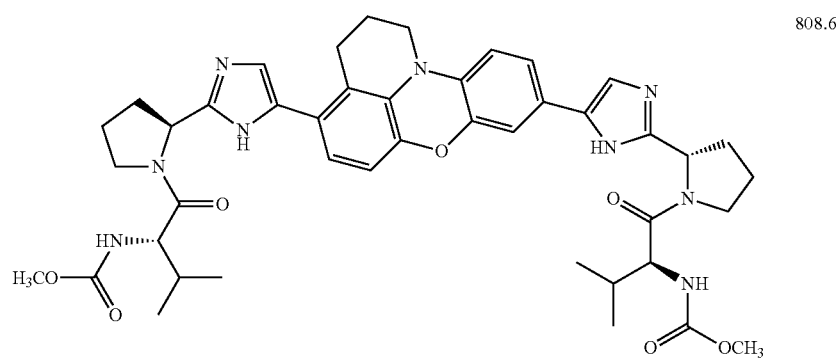 | 880.9 |
| 20 | 808.6 |

-continued

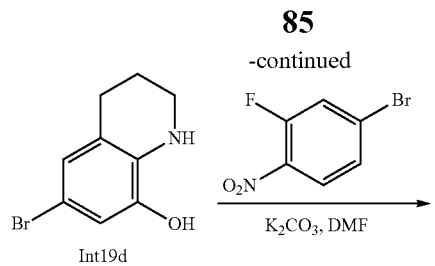

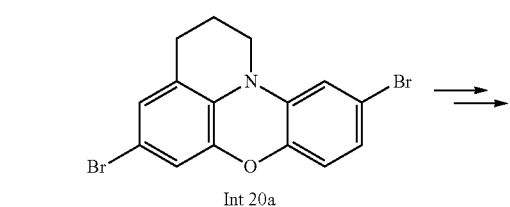

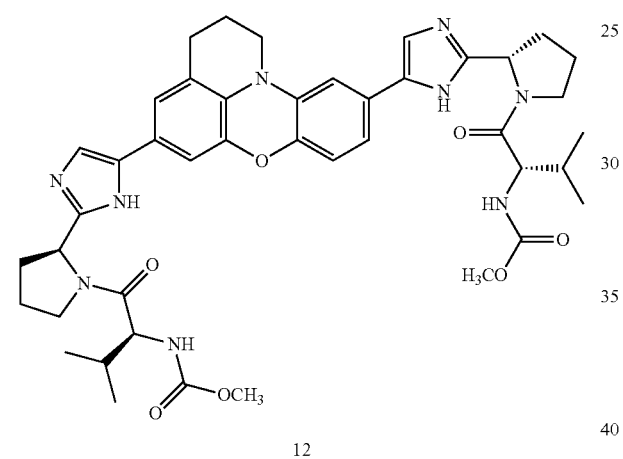

12

Step A—Synthesis of Compound Int-20a

A solution of compound Int-19d (2.5 g, 11 mmol) and 4-bromo-2-fluoronitrobenzene (2.4 g, 11 mmol) was reacted using the method described in Example 19, Step E, to provide compound Int-20a as yellow solid (2.9 g, 70%). $^1$H NMR: (CDCl$_3$) δ 6.76 (d, J=6.8 Hz, 1H), 6.70 (d, J=0.8 Hz, 1H), 6.64 (s, 1H), 6.54 (s, 1H), 6.49 (d, J=8.4 Hz, 1H), 3.25 (s, 2H), 2.62 (s, 2H), 2.02-2.08 (m, 2H).

Step B—Synthesis of Compound 12

Compound Int-20a was converted to compound 12 using the methods described in Example 19, steps F-I. $^1$H NMR: (CD$_3$OD) δ 7.74 (s, 1H), 7.64 (s, 1H), 7.05 (d, J=8.4 Hz, 1H), 7.01 (s, 1H), 6.94 (s, 1H), 6.88 (s, 1H), 6.77 (d, J=8.0 Hz, 1H), 5.17-5.23 (m, 2H-1), 4.22 (d, J=7.2 Hz, 2H), 4.10 (s, 2H), 3.84-3.85 (m, 2H), 3.66 (s, 6H), 3.45-3.47 (m, 2H-1), 2.75-2.77 (m, 2H), 2.55 (s, 2H), 2.25 (s, 2H), 2.15 (s, 6H), 2.01-2.06 (m, 2H), 0.89-0.93 (m, 12H). MS (ESI) m/z (M/2+H)$^+$: 404.7.

Example 21

Preparation of Methyl [(2S)-1-{(2S)-2-[5-(5-{2-[(2S)-1-{(2S)-2-[(methoxycarbonyl)amino]-3-methyl butanoyl}pyrrolidin-2-yl]-1H-imidazol-5-yl}-1,2-dihydro[1,4]oxazino[2,3,4-kl]phenoxazin-10-yl)-1H-imidazol-2-yl]pyrrolidin-1-yl}-3-methyl-1-oxobutan-2-yl]carbamate (Compound 13)

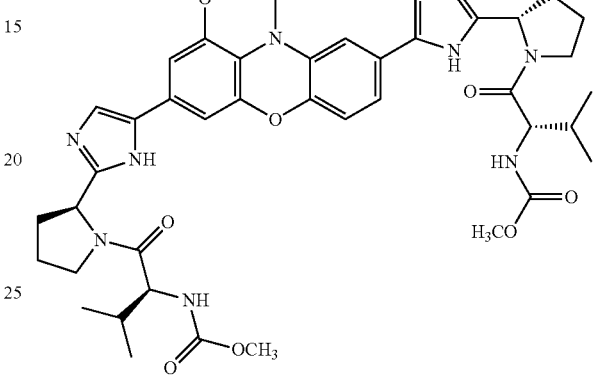

13

Step A—Synthesis of Compound Int-21a

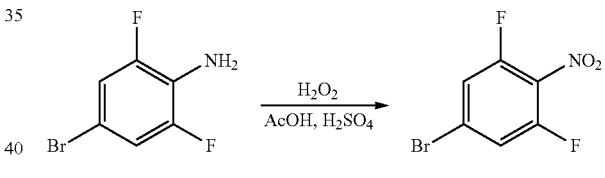

To a solution of compound 4-bromo-2,6-difluoroaniline (20 g, 0.1 mol) in acetic acid (120 mL) was added 30% H$_2$O$_2$ (80 mL) and concentrated sulfuric acid (4 mL). The reaction mixture was heated to 85° C. and allowed to stir at this temperature for 1 hour, then was cooled to room temperature and partitioned between EtOAc and water. The organic phase was separated and concentrated in vacuo. The residue obtained was purified using chromatography on silica gel [petroleum ether/EtOAc (gradient: 50/1-5/1)] to provide compound Int-21a (10.0 g, 42%). $^1$H NMR: (CDCl$_3$) δ: 7.31-7.29 (d, J=7.6 Hz, 2H).

Step B—Synthesis of Compound Int-21b

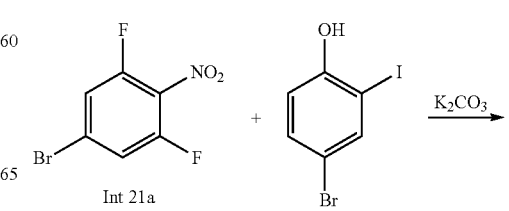

-continued

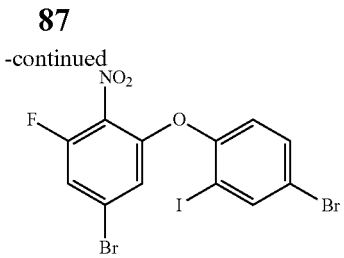

Int 21b

To a suspension of compound Int-21a (9.5 g, 40 mmol) and 4-bromo-2-iodophenol (11.9 g, 40 mmol) in DMF (200 mL) was added $K_2CO_3$ (11 g, 80 mmol) and the mixture was heated to 100° C. and allowed to stir at this temperature for 1 hour. The reaction mixture was cooled to room temperature and poured into water and extracted with EtOAc. The organic extract was washed with water, dried over sodium sulfate, filtered and concentrated in vacuo to provide compound Int-21b (20 g) which was used without further purification.

Step C—Synthesis of Compound Int-21c

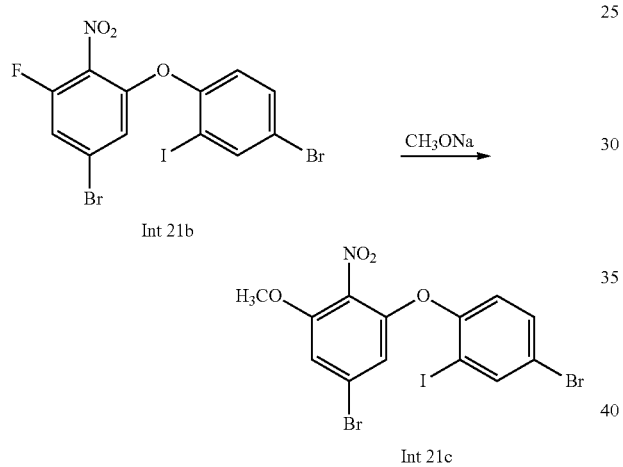

To a suspension of compound Int-21b (20 g) in DMF (100 mL) was added $CH_3ONa$ (10 g, 0.2 mol) and the reaction was allowed to stir for about 15 hours. The reaction mixture was partitioned between EtOAc and water and the organic layer was washed with water, dried over sodium sulfate, filtered and concentrated in vacuo. The residue obtained was purified using chromatography on silica gel to provide compound Int-21c (12 g). $^1$H NMR: ($CDCl_3$) δ: 7.94 (s, 1H), 7.45-7.43 (d, J=8.8 Hz, 1H), 6.90-6.85 (m, 2H), 6.36 (s, 1H), 3.86 (s, 3H).

Step D—Synthesis of Compound Int-21d

-continued

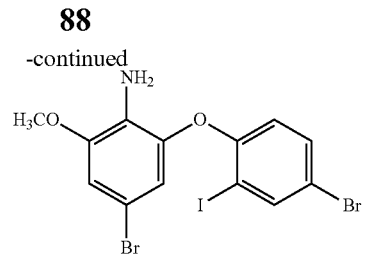

Int 21d

To a solution of compound Int-21c (10.6 g, 20 mmol) in ethanol (200 mL) was added HCl (conc., 1 mL) and then $SnCl_2$ (0.1 mol) and the suspension mixture was heated to reflux and allowed to stir at this temperature for about 15 hours. The reaction mixture was cooled and aqueous NaOH (20%, 500 mL) was added and extracted with dichloromethane. The extract was washed with brine and dried over sodium sulfate. The solvent was removed and the crude was purified using chromatography on silica gel [petroleum ether/EtOAc (gradient: 50/1-5/1)] to provide compound Int-21d (7.5 g, 75%). MS (ESI) m/z (M+H)$^+$: 498, 500 & 502.

Step E—Synthesis of Compound Int-21e

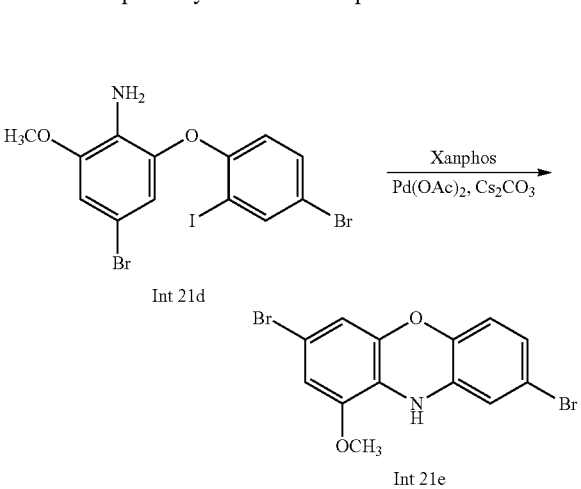

The suspension of compound Int-21d (2.5 g, 5 mmol), $Cs_2CO_3$ (3.25 g, 10.0 mmol), Xantphos (0.25 mmol) and Pd(OAc)$_2$ (0.25 mmol) in THF (250 mL) was degassed, refilled with $N_2$ then the reaction mixture was heated to reflux and allowed to stir at this temperature for 2 hours. The reaction was cooled and the solvent was removed and the crude was purified using chromatography on silica gel eluted with petroleum ether/EtOAc (gradient: 10/1-3/1) to provide compound Int-21e (1.2 g, yield: 64%). MS (ESI) m/z (M+H)$^+$: 370, 372 & 374.

Step F—Synthesis of Compound Int-21f

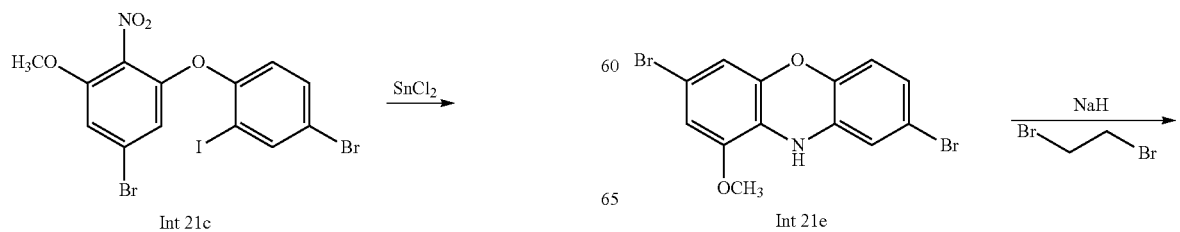

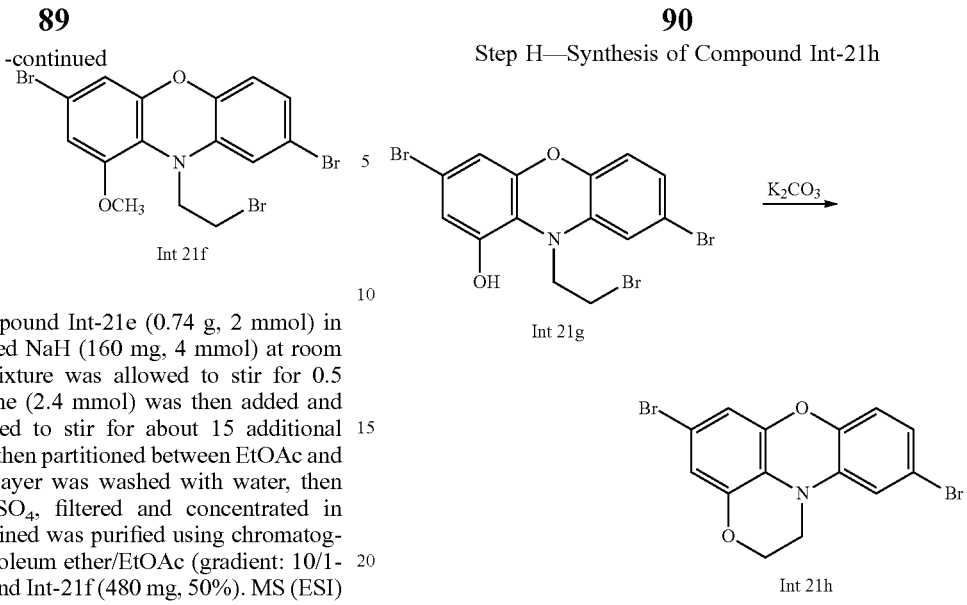

To a solution of compound Int-21e (0.74 g, 2 mmol) in DMF (20 mL) was added NaH (160 mg, 4 mmol) at room temperature and the mixture was allowed to stir for 0.5 hours. 1,2-dibromoethane (2.4 mmol) was then added and the reaction was allowed to stir for about 15 additional hours. The mixture was then partitioned between EtOAc and water and the organic layer was washed with water, then brine, dried over $Na_2SO_4$, filtered and concentrated in vacuo. The residue obtained was purified using chromatography on silica gel [petroleum ether/EtOAc (gradient: 10/1-3/1)] to provide compound Int-21f (480 mg, 50%). MS (ESI) m/z (M+H)$^+$: 476, 478, 480 & 482.

Step G—Synthesis of Compound Int-21g

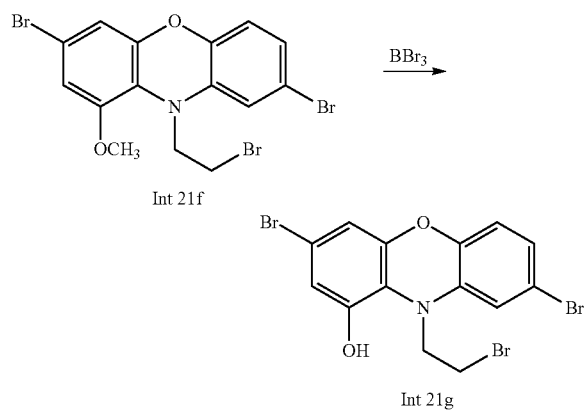

To a solution of compound Int-21f (480 mg, 1 mmol) in dichloromethane (10 mL) was added $BBr_3$ (1 mL) and the reaction was allowed to stir at room temperature for 24 hours. The reaction mixture was then poured onto ice and extracted with EtOAc. The extract was washed with brine, dried over $Na_2SO_4$, filtered and concentrated in vacuo to provide compound Int-21g (500 mg, crude) which was used without further purification. MS (ESI) m/z (M+H)$^+$: 462, 464, 466 & 468.

Step H—Synthesis of Compound Int-21h

The suspension of compound Int-21g (0.5 g) and $K_2CO_3$ (0.5 g) in DMF (10 mL) was allowed to stir at 60° C. for 1 hour. The reaction mixture was cooled and poured into water then extracted with EtOAc. The extract was washed with water then brine, dried over $Na_2SO_4$, filtered and concentrated in vacuo. The residue obtained was purified using preparative TLC to provide Int-21 h (280 mg, 70% for two steps). MS (ESI) m/z (M+H)$^+$: 382, 384 & 386.

Step I—Synthesis of Compound 13

Compound 13 was prepared from compound Int-21h using the method and reagents described in Example 19 steps F-I. Compound 13: $^1$H NMR: (MeOD) δ: 7.72 (s, 1 H), 7.64 (s, 1H), 6.91-7.09 (m, 2H), 6.65-6.88 (m, 3H), 5.10-5.24 (m, 2H), 4.32-4.48 (m, 2H), 4.12-4.22 (m, 2H), 4.01-4.12 (m, 2H), 3.74-3.89 (m, 2H), 3.48-3.72 (m, 8H), 2.40-2.60 (m, 2H), 1.94-2.28 (m, 8H), 0.80-1.00 (m, 12H). MS (ESI) m/z (M+H)$^+$: 810.

Example 22

Methyl [(2S)-1-{(2S)-2-[5-(3-{2-[(2S)-1-{(2S)-2-[(methoxycarbonyl)amino]-3-methyl butanoyl}pyrrolidin-2-yl]-1H-imidazol-5-yl}furo[2,3,4-kl]xanthen-8-yl)-1H-imidazol-2-yl]pyrrolidin-1-yl}-3-methyl-1-oxobutan-2-yl]carbamate (Compound 14)

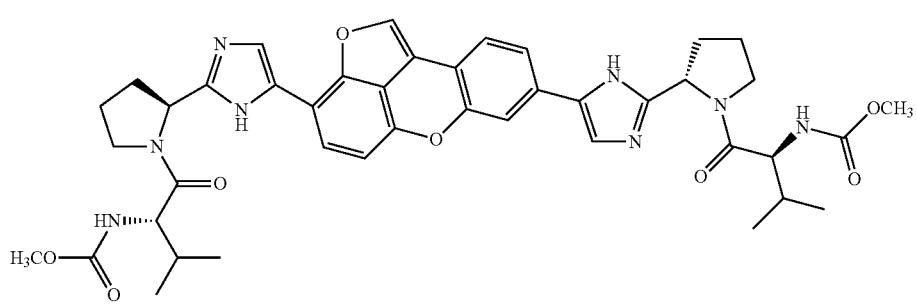

Step A—Synthesis of Compound Int-22a

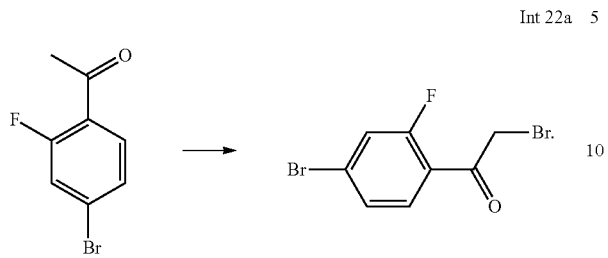

To a solution of compound 4-bromo-2-fluoroacetophenone (8.0 g, 37.04 mmol) in CHCl$_3$ (100 mL) was added bromine dropwise at 0° C. and the mixture was allowed to stir at room temperature for 20 hours. The reaction was quenched with aqueous NaSO$_3$ and the reaction mixture was washed with water then dried over sodium sulfate, filtered and concentrated in vacuo. The residue obtained was purified using flash chromatography on silica gel to provide compound Int-22a (7.2 g, 66%). $^1$H NMR: (CDCl$_3$) δ: 4.46 (s, 2H), 7.37-7.47 (m, 2H), 7.80-7.87 (m, 1H).

Step B—Synthesis of Compound Int-22b

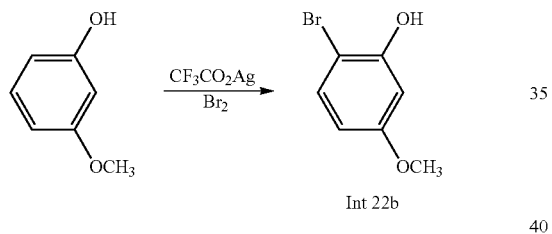

To a suspension of 3-methoxyphenol (3.0 g, 24.18 mmol) and CF$_3$COOAg (5.3 g, 24.2 mmol) in CHCl$_3$ (15 mL) was added Br$_2$ in CHCl$_3$ (20 mL) dropwise and the mixture was allowed to stir at room temperature for 20 hours. The reaction was quenched with aqueous NaSO$_3$ and washed with water. The organic phase was dried over sodium sulfate, filtered and concentrated in vacuo to provide a residue that was purified using flash chromatography on silica gel to provide compound Int-22b (3.1 g, 63%). $^1$H NMR: (CDCl$_3$) δ:3.77 (s, 3H), 5.47 (s, 1H), 6.40-6.42 (m, 1H), 6.60 (s, 1H), 7.30-7.32 (m, 1H).

Step C—Synthesis of Compound Int-22c

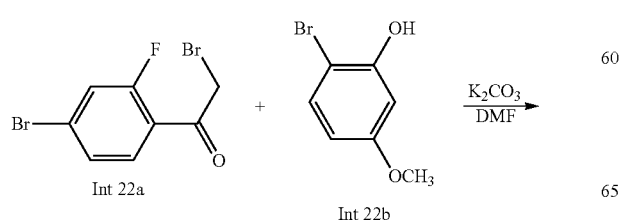

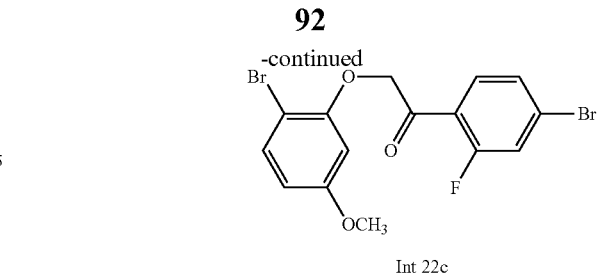

A suspension of compound Int-22a (3.0 g, 10.24 mmoL), compound Int-22b (2.05 g, 10.24 mmoL) and K$_2$CO$_3$ (2.8 g, 20.4 mmol) in DMF (20 mL) was allowed to stir for 3 hours. The reaction mixture was then partitioned between EtOAc and water and the organic layer was separated and washed with water, then dried over sodium sulfate, filtered and concentrated in vacuo. The residue obtained was purified using flash chromatography on silica gel [petroleum ether/EtOAc (gradient: 200/1-10/1)] to provide to provide compound Int-22c (1.6 g, 40%). $^1$H NMR: (CDCl$_3$) δ: 3.79 (s, 3H), 7.95 (s, 1H), 6.60-6.63 (d, J=8.8 Hz, 1H), 7.27-7.43 (m, 4H), 7.69 (s, 1H).

Step D—Synthesis of Compound Int-22d

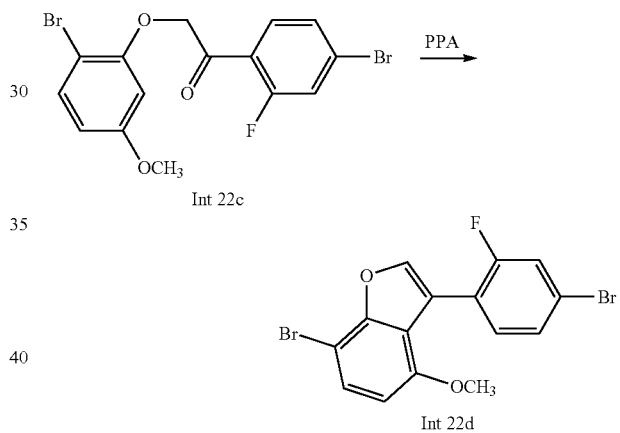

To PPA (15 mL) was added compound Int-22c (2.3 g, 5.53 mmol) and the resulting reaction was heated to 120° C. and allowed to stir at this temperature for 3 hours. The reaction was cooled and poured into ice and extracted with EtOAc. The extract was washed with brine and dried over sodium sulfate. The solvent was removed to provide the crude Compound Int-22d (1.5 g, 68%) $^1$H NMR: (CDCl$_3$) δ: 3.79 (s, 3H), 7.95 (s, 1H), 6.60-6.63 (d, J=8.8 Hz, 1H), 7.27-7.43 (m, 4H), 7.69 (s, 1H).

Step E—Synthesis of Compound Int-22e

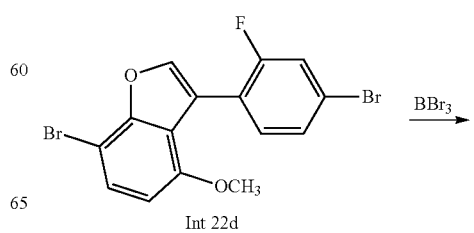

-continued

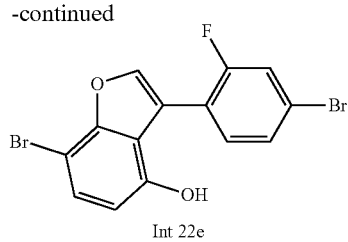
Int 22e

To a solution of compound Int-22d (1.2 g, 3.0 mmol) in dichloromethane (20 mL) was added BBr$_3$ (6.0 mmol) in portions and the mixture was allowed to stir at room temperature for about 15 hours. The reaction mixture was poured onto ice and extracted with dichloromethane. The extract was washed with brine and dried over sodium sulfate. The solvent was removed to provide crude Compound Int-22e (1.1 g) which was directly used in next reaction.

Step G—Synthesis of Compound 14

Compound Int-22f was converted to compound 14 using the method and reagents described in Example 19 steps F-I. Compound 14: $^1$H NMR: (MeOD) δ: 7.48-8.00 (m, 7H), 6.74-6.82 (m, 1H), 5.21-5.27 (m, 2H), 3.88-4.23 (m, 6H), 3.64 (s, 6H), 2.54 (s, 2H), 2.07-2.28 (m, 8H), 0.91-0.96 (m, 12H). MS (ESI) m/z (M+H)$^+$: 793.

Example 23

Preparation of Methyl [(2S)-1-{(2S)-2-[5-(4-{2-[(2S)-1-{(2S)-2-[(methoxycarbonyl)amino]-3-methyl butanoyl}pyrrolidin-2-yl]-1H-imidazol-5-yl}-1,10b-dihydrofuro[2,3,4-kl]xanthen-9-yl)-1H-imidazol-2-yl]pyrrolidin-1-yl}-3-methyl-1-oxobutan-2-yl]carbamate (Compound 15)

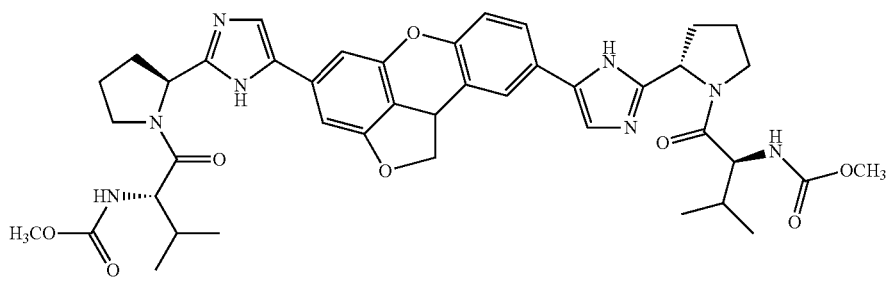

Step F—Synthesis of Compound Int-22f

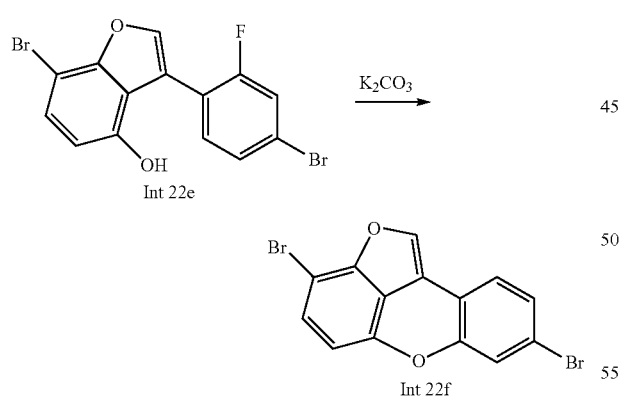

The suspension of compound Int-22e (0.9 g, 2.34 mmoL) and K$_2$CO$_3$ (0.65 g, 4.68 mmol) in DMF (10 mL) was allowed to stir at 120° C. for 6 hours. The reaction was then cooled and poured into water and extract with EtOAc. The organic extract was washed with brine and dried over sodium sulfate. The solvent was removed and the crude was washed with methanol to provide Compound Int-22f (0.8 g, 94%). $^1$H NMR: (CDCl$_3$) δ: 6.62-6.64 (m, 1H), 7.24-7.36 (m, 4H), 7.61 (s, 1H).

Step A—Synthesis of Compound Int-23a

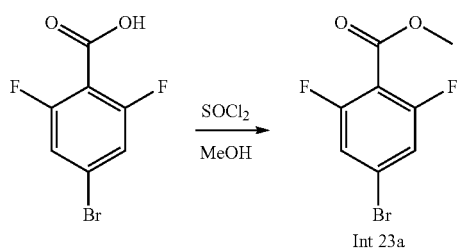

To a stirred solution of 4-bromo-2,6-dibromobenzoic acid (47 g, 0.2 mol) in methanol (500 mL) was added SOCl$_2$ (36 g, 0.30 mol) dropwise at room temperature and the reaction mixture was heated to reflux and allowed to stir at this temperature for 3 hours, then the reaction was cooled to room temperature. The solvent was removed and the residue obtained was purified using the chromatography on silica gel [gradient: petroleum ether/EtOAc (50/1-5/1)] to provide compound Int-23a (45 g, 90%). MS (ESI) m/z (M+H)$^+$: 251.

Step B—Synthesis of Compound Int-23b

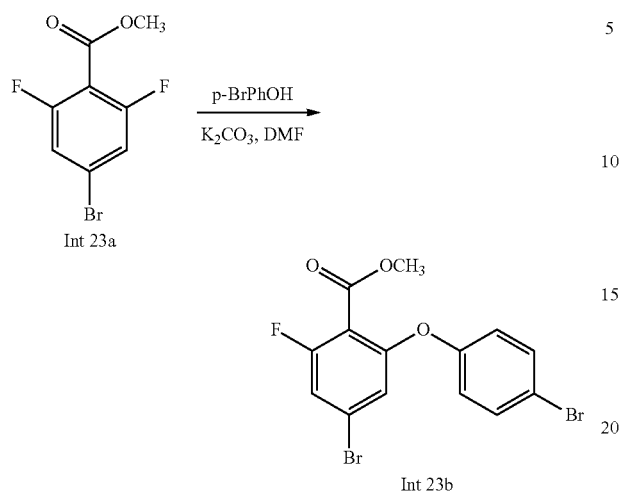

To a solution of compound Int-23a (45 g, 0.18 mol) and 4-bromophenol (31g, 0.18 mol) in DMF (500 mL) was added $K_2CO_3$ (30 g, 0.2 mol) and the mixture was allowed to stir at 80-100° C. for 1 hour. The reaction mixture was cooled and partitioned between EtOAc and water. The organic layer was separated, washed with water and dried over sodium sulfate. The solvent was removed to provide crude compound Int-23b (70 g), which was used in next step without further purification. MS (ESI) m/z $(M+F1)^+$: 402.9, 404.9 & 406.9.

Step C—Synthesis of Compound Int-23c

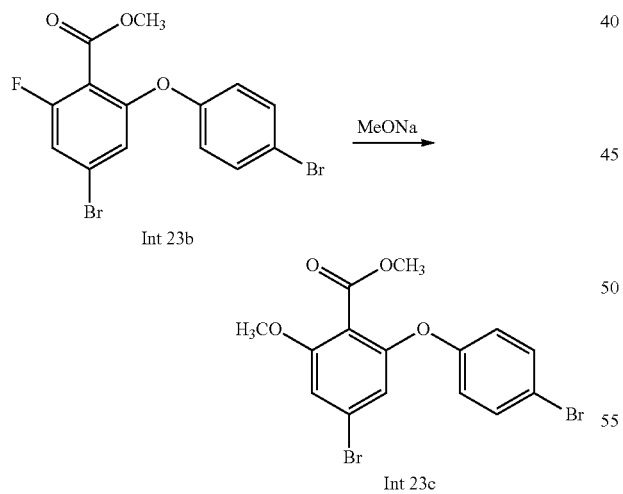

The solution of compound Int-23b (70 g) in DMF (500 mL) was added $NaOCH_3$ (20 g, 0.4 mol) and the mixture was allowed to stir at 80° C. for 4 hours. The reaction mixture was cooled then partitioned between water and EtOAc. The organic layer was separated, washed with water and dried over sodium sulfate. After removing the solvent the crude was purified using the chromatography on silica gel eluted [gradient: petroleum ether/EtOAc (20/1-5/1)] to provide Compound Int-23c (32 g, Yield: 45% for two steps). MS (ESI) m/z $(M+H^+)$: 414.9, 416.9 & 418.9.

Step D—Synthesis of Compound Int-23d

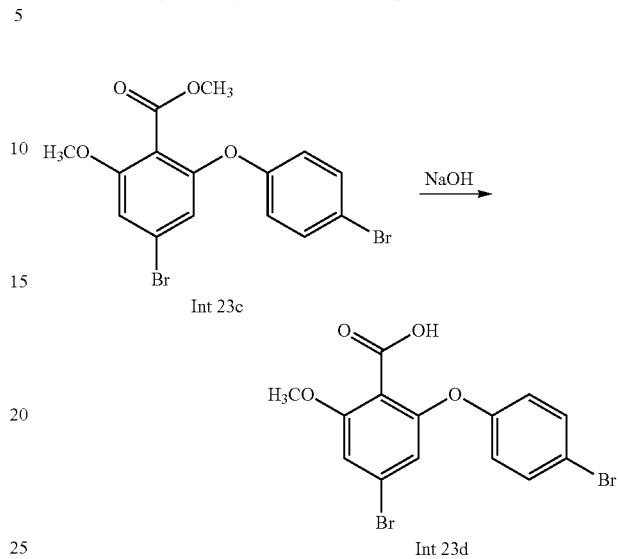

To a solution of compound Int-23c (32 g, 0.08 mol) in THF (500 mL)/$H_2O$ (100 mL) was added NaOH (16 g, 0.4 mol) and the mixture was allowed to stir at room temperature for about 15 hours. The reaction mixture was acidified with HCl to pH=3 and extracted with EtOAc. The extract was washed with brine and dried over sodium sulfate. The solvent was removed to provide compound Int-23d (30 g, crude), which was used in next step without further purification.

Step E—Synthesis of Compound Int-23e

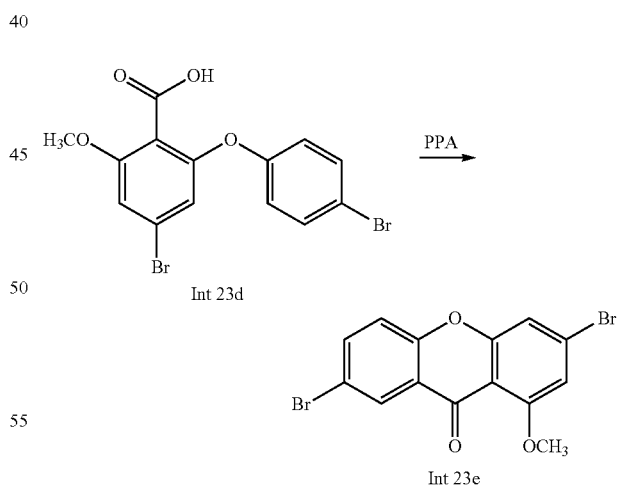

To PPA (300 mL) was added compound Int-23d (30 g, crude). The resulting slurry was degassed and refilled with $N_2$. The suspension was allowed to stir at 100° C. for 2 hours. The reaction mixture was cooled and partitioned between EtOAc and water. The organic layer was separated, washed with brine and dried over sodium sulfate. The solvent was removed and the crude was washed with methanol to provide compound Int-23e (12 g, 39% for two steps).

¹H NMR (CDCl₃) δ: 8.37 (s, 1H), 7.73-7.77 (d, J=8.8 Hz, 1H), 7.25-7.32 (m, 2H), 6.94 (s, 1H), 4.02 (s, 3H).

Step F Synthesis of Compound Int-23g

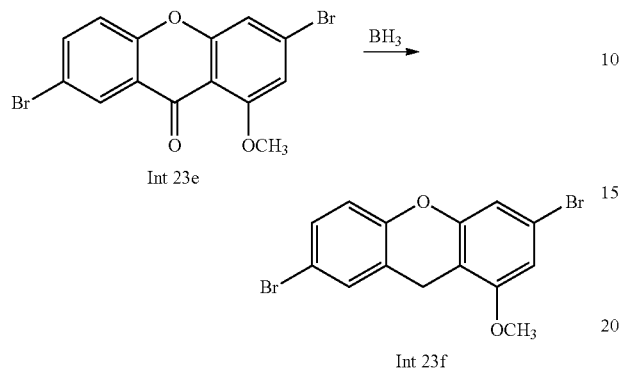

To a stirred solution of compound Int-23e (12 g, 31 mmol) in THF (100 mL) was added BH₃.SMe₂ (100 mmol) dropwise at room temperature and the reaction mixture was heated to reflux and allowed to stir at this temperature for 6 hours. The reaction was quenched with methanol and the solvent was removed. The crude was washed with methanol to provide compound Int-23f (10 g, 87%). ¹H NMR (CDCl₃) δ 7.19-7.22 (m, 2H), 7.79-6.87 (d, J=8.8 Hz, 1H), 6.77 (s, 1H), 6.61 (s, 1H), 3.78 (s, 3H), 3.75 (s, 2H).

Step G—Synthesis of Compound Int-23g

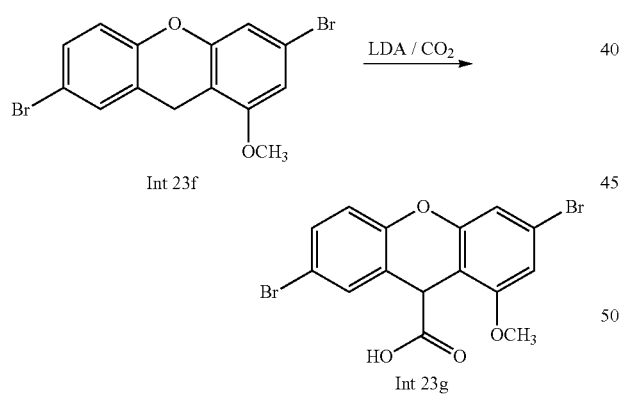

To a stirred solution of compound Int-23f (10 g, 27 mmol) in anhydrous THF (100 mL) was added LDA (54 mmol) dropwise at −78° C. under N₂ and the mixture was allowed to stir at room temperature for 0.5 hours. Thereto was added 5 g of dry-ice and the mixture was allowed to stir for an additional 1 hour. The reaction was quenched with saturated ammonium chloride, extracted with EtOAc and the solvent was removed. The crude was washed with petroleum ether/EtOAc (5/1) to provide compound Int-23g (6 g, yield: 53%). ¹H NMR: (CDCl₃) δ 12.70-13.12 (br, 1H), 7.62 (s, 1H), 7.48-7.50 (d, J=8.8 Hz, 1H), 7.09-7.12 (d, J=8.8 Hz, 1H), 6.99 (s, 2H), 4.92 (s, 1H), 3.84 (s, 3H).

Step H—Synthesis of Compound Int-23h

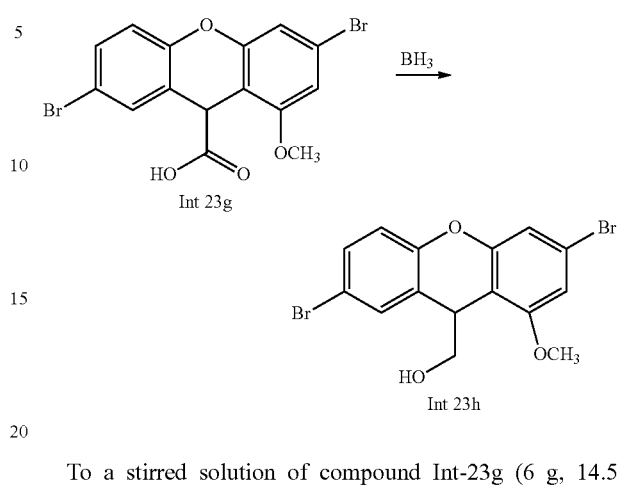

To a stirred solution of compound Int-23g (6 g, 14.5 mmol) in THF (100 mL) was added BH₃.SMe₂ (50 mmol) dropwise at room temperature and the reaction mixture was heated to reflux and allowed to stir at this temperature for 6 hours. The reaction was quenched with methanol and the solvent was removed. The crude was purified using chromatography on silica gel [gradient: petroleum ether/EtOAc (20/1-5/1)] to provide compound Int-23h (4.4 g, 76%). ¹H NMR: (CDCl₃) δ 7.39 (s, 1H), 7.31-7.35 (d, J=8.8 Hz, 1H), 6.93-6.75 (d, J=8.8 Hz, 1H), 6.90 (s, 1H), 6.75 (s, 1H), 4.22-4.25 (t, J=4.8 Hz, 2H), 3.85 (s, 3H), 3.36-3.38 (m, 2H), 1.54-1.58 (t, J=6.4 Hz, 1H).

Step I—Synthesis of Compound Int-23i

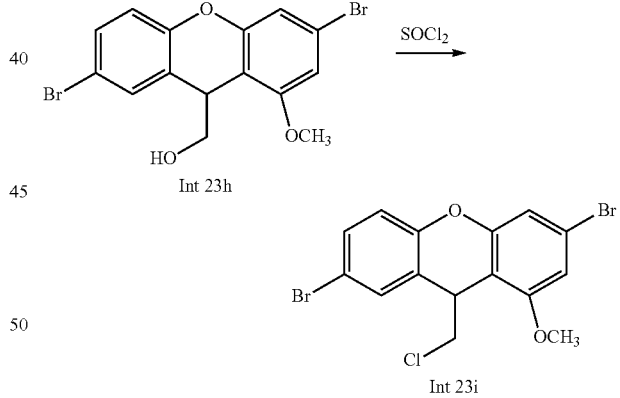

To a stirred solution of compound Int-23h (4 g, 10 mmol) in THF (40 mL) was added pyridine (20 mmol) and then SOCl₂ (1.5 g, 12 mmol) and the reaction mixture was heated to reflux and allowed to stir at this temperature for 8 hours. The reaction was cooled to room temperature, poured into water and extracted with EtOAc. The extract was washed with brine and dried over Na₂SO₄. The solvent was removed and the crude was purified using chromatography on silica gel [gradient: petroleum ether/EtOAc (50/1-5/1)] to provide compound Int-23i (2.4 g, 60%). ¹H NMR: (DMSO-d₆) δ 7.36 (s, 1H), 7.29-7.32 (d, J=8.8 Hz, 1H), 7.86-6.92 (s, 2H), 6.70 (s, 1H), 4.41-4.43 (t, J=8.8 Hz, 1H), 3.81 (s, 3H), 3.64 (s, 2H).

Step J—Synthesis of Compound Int-23j

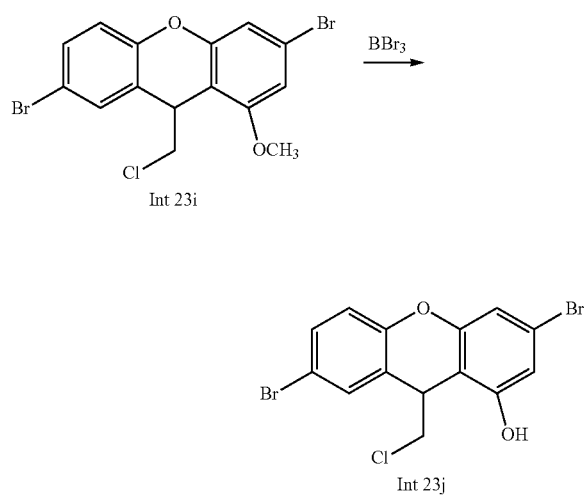

To a stirred solution of compound Int-23i (2.4 g, 6.0 mmol) in dichloromethane (50 mL) was added BBr$_3$ (30 mmol) dropwise at 0° C. and the mixture was allowed to stir at room temperature for 24 hours, then poured into ice and extracted with EtOAc. The extract was washed with brine and dried over Na$_2$SO$_4$. The solvent was removed in vacuo and the residue obtained was purified using chromatography on silica gel [gradient: petroleum ether/EtOAc (20/1-2/1)] to provide compound Int-23j (2 g, 82%). $^1$H NMR (DMSO-d$_6$) δ 10.69 (s, 1H), 7.71 (s, 1H), 7.43-7.46 (d, J=8.8 Hz, 1H), 7.02-7.05 (d, J=8.8 Hz, 1H), 6.76-6.79 (m, 2H), 4.63 (s, 1H), 3.91-3.98 (m, 2H).

Step K—Synthesis of Compound Int-23k

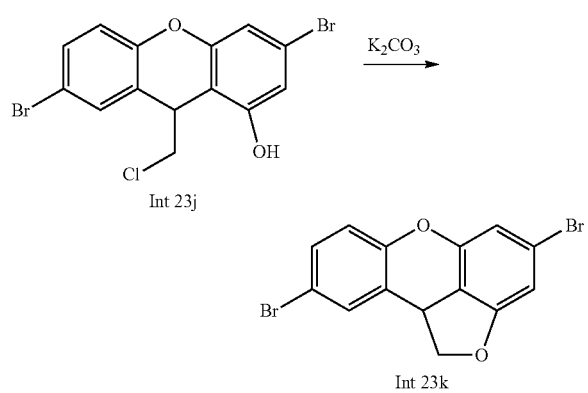

To a stirred solution of compound Int-23j (2 g, 5 mmol) in DMF (50 mL) was added K$_2$CO$_3$ (1.38 g, 10 mmol) and the resulting suspension was heated to 80° C. and allowed to stir at this temperature for about 15 hours. The reaction mixture was cooled to room temperature and partitioned between EtOAc and water. The organic phase was washed with water then brine, dried over Na$_2$SO$_4$, filtered and concentrated in vacuo. The residue obtained was purified using chromatography on silica gel [gradient: petroleum ether/EtOAc (50/1-5/1)] to provide compound Int-23k (280 mg, 15%). $^1$H NMR (CDCl$_3$) δ 7.35-7.38 (d, J=8.8 Hz, 1H), 7.17 (s, 1H), 7.07-7.09 (d, J=8.8 Hz, 1H), 6.84 (s, 1H), 6.76 (s, 1H), 5.21 (s, 1H), 4.51 (s, 2H).

Step L—Synthesis of Compound 15

Compound 15 was made from compound Int-23k using the methods described in Example 19 steps F-I. $^1$H NMR (MeOD) δ 7.78-7.80 (m, 2H), 7.63-7.65 (d, J=8.4 Hz 1H), 7.59 (s, 1H), 7.35-7.37 (d, J=8.4 Hz, 1H), 7.06 (s, 1H), 6.95 (s, 1H), 5.36-5.49 (m, 1H), 5.15-5.24 (m, 2H), 4.79-4.88 (m, 1H), 4.79-4.88 (m, 1H), 4.52-4.63 (m, 1H), 4.18-4.20 (d, J=7.2 Hz, 1H), 4.02-4.12 (m, 2H), 3.78-3.89 (m, 2H), 3.63 (s, 6H), 2.42-2.60 (m, 2H), 1.96-2.30 (m, 8H), 0.82-1.00 (m, 12H). MS (ESI) m/z (M+H)$^+$: 795.

Example 24

Cell-Based HCV Replicon Assay

To measure cell-based anti-HCV activity of selected compounds of the present invention, replicon cells were seeded at 5000 cells/well in 96-well collagen I-coated Nunc plates in the presence of the test compound. Various concentrations of test compound, typically in 10 serial 2-fold dilutions, were added to the assay mixture, with the starting concentration ranging from 250 μM to 1 μM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA (SEQ. ID. NO. 1); 5B.2R, TTGATGGGCAGCTTGGTTTC (SEQ. ID. NO. 2); the probe sequence was FAM-labeled CACGCCAT-GCGCTGCGG (SEQ. ID. NO. 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 minutes, 95° C. for 10 minutes, 40 cycles of 95° C. for 15 sec, 60° C. for 1 minutes. The ΔCT values (CT$_{5B}$-CT$_{GAPDH}$) were plotted against the concentration of test compound and fitted to the sigmoid dose-response model using XLfit4 (MDL). EC$_{50}$ was defined as the concentration of inhibitor necessary to achieve ΔCT=1 over the projected baseline; EC$_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV replicon assay data was calculated for selected compounds of the present invention using this method and is provided in the table below. Replicon EC$_{50}$ data for selected compounds of the present invention is provided in the table below.

| Compound | 1a WT (nM) | 1a Y93H (nM) | 1b WT (nM) | 1b Y93H (nM) | 2a WT (nM) | 2b WT (nM) | 3a WT (nM) | 4a WT (nM) |
|---|---|---|---|---|---|---|---|---|
| 1 | 0.01071 | 41.72 | 0.009 | 0.56 | 0.004 | NA | 0.323 | 0.044 |
| 2 | 0.07357 | 454.4 | 0.00443 | NA | 0.018 | NA | 1.26 | 4.91 |
| 3 | 0.097 | 347.8 | 0.007 | NA | 0.006 | NA | 0.019 | 0.040 |
| 4 | 0.007 | 64.4 | 0.006 | NA | 0.012 | NA | 1.9 | 3.12 |
| 5 | >26 | NA | 19 | NA | 20 | NA | NA | NA |
| 6 | 0.037 | 43.53 | 0.005 | 0.303 | 0.011 | 18.9 | 0.22 | 0.22 |
| 7 | 0.1 | 263 | 0.044 | NA | 0.063 | NA | 1.1 | 1.05 |
| 8 | 0.004 | 11.5 | 0.001 | NA | NA | NA | 0.31 | 0.019 |
| 9 | 0.01 | 27.5 | 0.005 | NA | NA | NA | 1.5 | 0.10 |
| 10 | 0.027 | 35.1 | 0.005 | NA | 0.003 | 49 | 0.69 | 0.37 |
| 11 | 0.1 | 504 | 0.031 | NA | 0.345 | NA | 10 | 1.022 |
| 12 | 0.056 | 115.2 | 0.003 | NA | 0.002 | NA | 0.375 | 0.130 |
| 13 | 0.002 | 143 | 0.005 | 19 | 0.01 | 19.3 | 1.63 | 0.48 |
| 14 | 0.011 | 31.5 | 0.002 | 0.278 | 0.002 | 34.5 | 0.161 | 0.056 |
| 15 | 0.06 | 83 | 0.004 | NA | NA | NA | 0.52 | 0.39 |
| 16 | 0.1 | 50.9 | 0.009 | 9.1 | 0.104 | 9.074 | 9.61 | 1.31 |
| 17 | 0.006 | 19.5 | 0.001 | 19.6 | 0.007 | 19.62 | 0.067 | 0.026 |
| 18 | 0.009 | 32 | 0.002 | NA | NA | 40 | 0.936 | 0.056 |
| 19 | 0.1 | NA | 0.003 | NA | 0.53 | 122 | 10 | 0.17 |

NA = not available

Uses of the Tetracyclic Xanthene Derivatives

The Tetracyclic Xanthene Derivatives are useful in human and veterinary medicine for treating or preventing a viral infection in a patient. In one embodiment, the Tetracyclic Xanthene Derivatives can be inhibitors of viral replication. In another embodiment, the Tetracyclic Xanthene Derivatives can be inhibitors of HCV replication. Accordingly, the Tetracyclic Xanthene Derivatives are useful for treating viral infections, such as HCV. In accordance with the invention, the Tetracyclic Xanthene Derivatives can be administered to a patient in need of treatment or prevention of a viral infection.

Accordingly, in one embodiment, the invention provides methods for treating a viral infection in a patient comprising administering to the patient an effective amount of at least one Tetracyclic Xanthene Derivative or a pharmaceutically acceptable salt thereof.

Treatment or Prevention of a Flaviviridae Virus

The Tetracyclic Xanthene Derivatives can be useful for treating or preventing a viral infection caused by the Flaviviridae family of viruses.

Examples of Flaviviridae infections that may be treated or prevented using the present methods include one or more of dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The Tetracyclic Xanthene Derivatives are useful in the inhibition of HCV (e.g., HCV NS5A), the treatment of HCV infection and/or reduction of the likelihood or severity of symptoms of HCV infection and the inhibition of HCV viral replication and/or HCV viral production in a cell-based system. For example, the Tetracyclic Xanthene Derivatives are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Tetracyclic Xanthene Derivative or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Tetracyclic Xanthene Derivatives are also useful in the preparation and execution of screening assays for antiviral compounds. For example the Tetracyclic Xanthene Derivatives are useful for identifying resistant HCV replicon cell lines harboring mutations within NS5A, which are excellent screening tools for more powerful antiviral compounds. Furthermore, the Tetracyclic Xanthene Derivatives are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not Tetracyclic Xanthene Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Tetracyclic Xanthene Derivative, or a pharmaceutically acceptable salt thereof, and (ii) at least one additional therapeutic agent that is other than a Tetracyclic Xanthene Derivative, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tetracyclic Xanthene Derivative and an additional therapeutic agent may be present in fixed amounts (dosage amounts) in a single dosage unit (e.g., a capsule, a tablet and the like).

In one embodiment, the at least one Tetracyclic Xanthene Derivative is administered during a time when the additional therapeutic agent(s) exert their prophylactic or therapeutic effect, or vice versa.

In another embodiment, the at least one Tetracyclic Xanthene Derivative and the additional therapeutic agent(s) are administered in doses commonly employed when such agents are used as monotherapy for treating a viral infection.

In another embodiment, the at least one Tetracyclic Xanthene Derivative and the additional therapeutic agent(s) are administered in doses lower than the doses commonly employed when such agents are used as monotherapy for treating a viral infection.

In still another embodiment, the at least one Tetracyclic Xanthene Derivative and the additional therapeutic agent(s) act synergistically and are administered in doses lower than the doses commonly employed when such agents are used as monotherapy for treating a viral infection.

In one embodiment, the at least one Tetracyclic Xanthene Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Tetracyclic Xanthene Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Tetracyclic Xanthene Derivative and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin. HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759/VX-759 (ViroChem Pharma/Vertex), HCV-371 (Wyeth/VirroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), 81479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222NX-222 (ViroChemNertex), VCH-916 (ViroChem), VCH-716 (ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (1denix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, those disclosed in Landro et al., *Biochemistry*, 36(31):9340-9348 (1997); Ingallinella et al., *Biochemistry*, 37(25):8906-8914 (1998); Llinas-Brunet et al., *Bioorg Med Chem Lett*, 8(13):1713-1718 (1998); Martin et al., *Biochemistry*, 37(33):11459-11468 (1998); Dimasi et al., *J Virol*, 71(101:7461-7469 (1997); Martin et al., *Protein Eng*, 10(51:607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

107
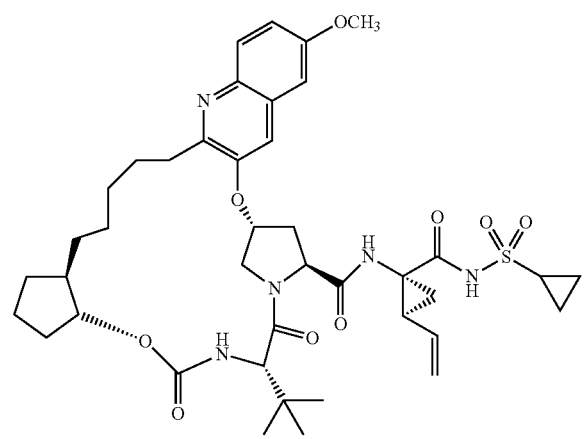
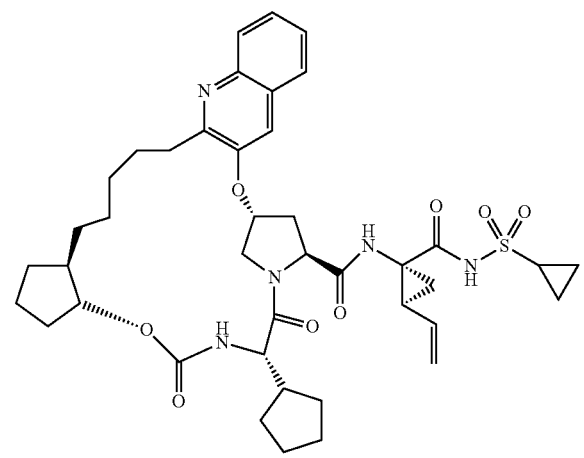
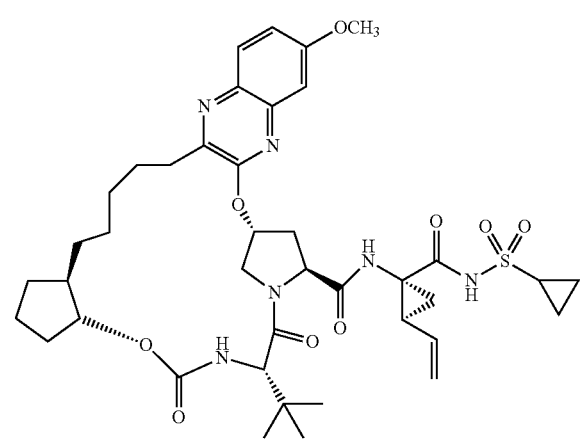
108
-continued
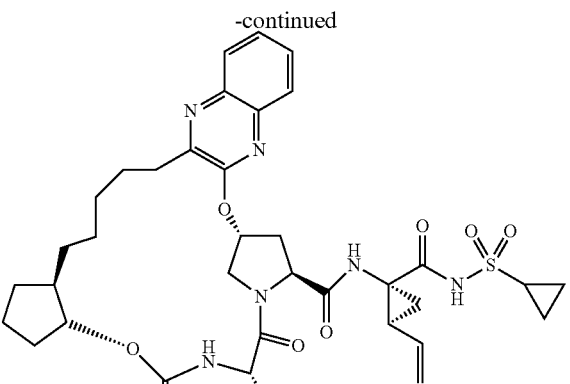
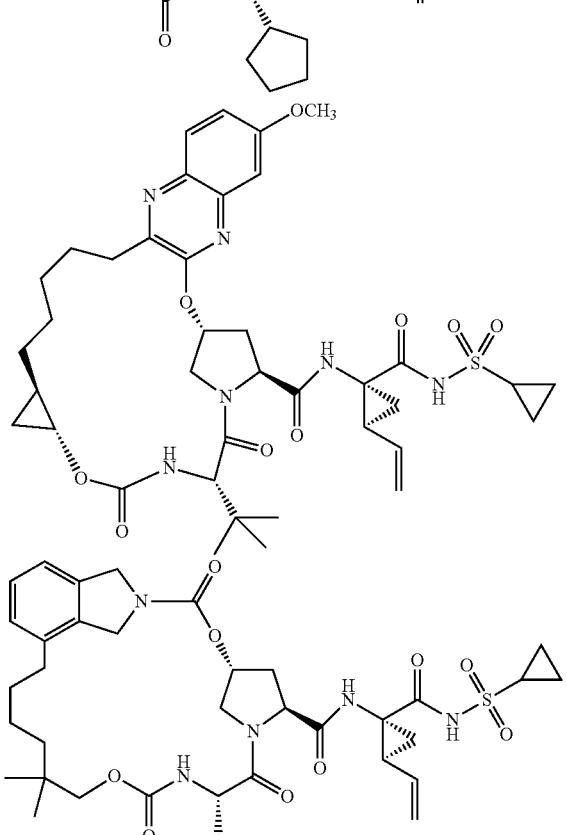
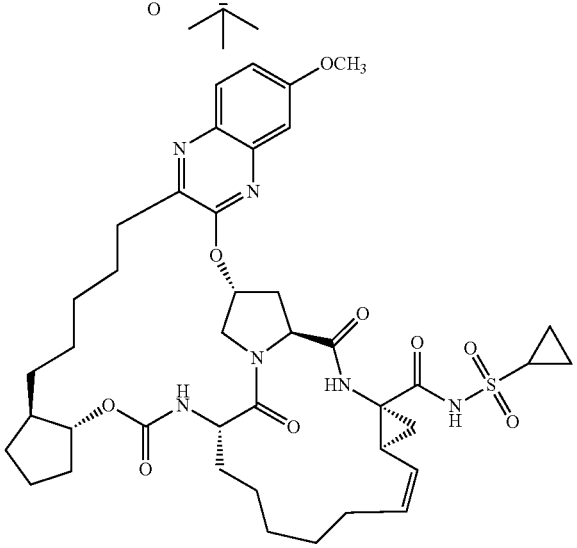

109
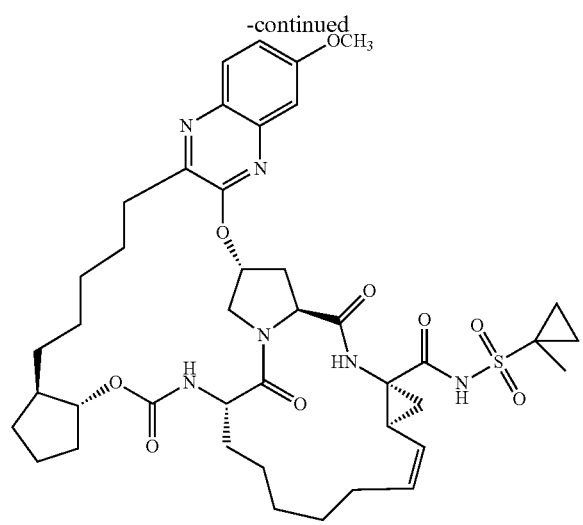
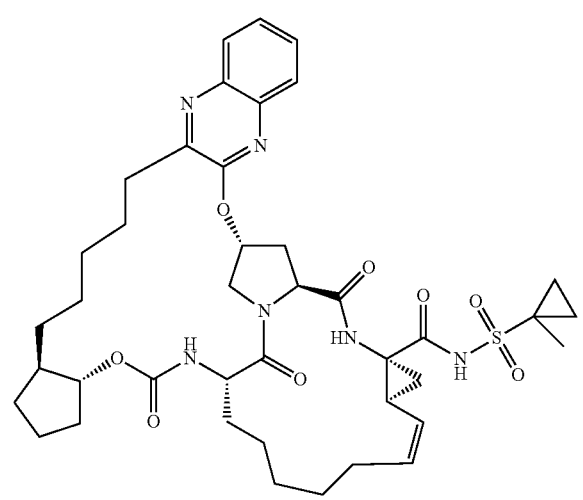
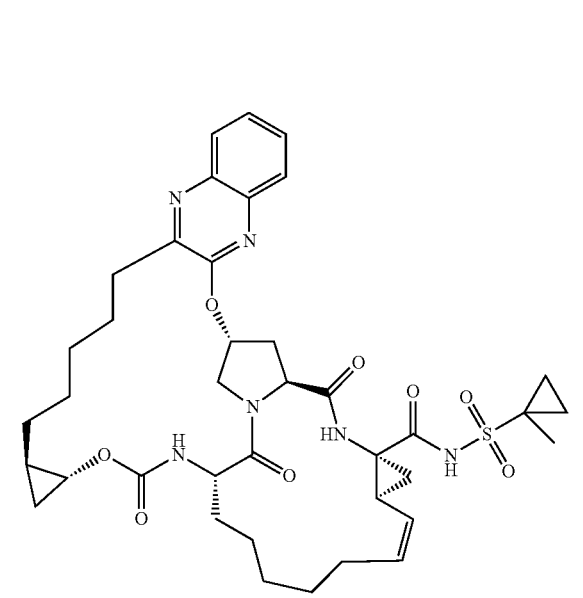
110
-continued
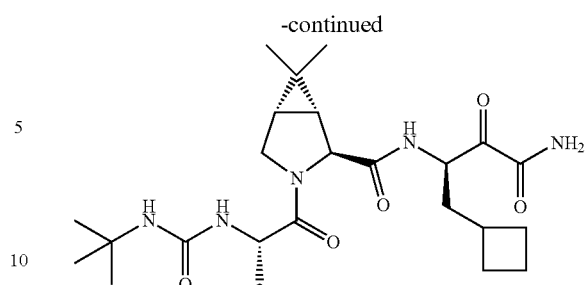
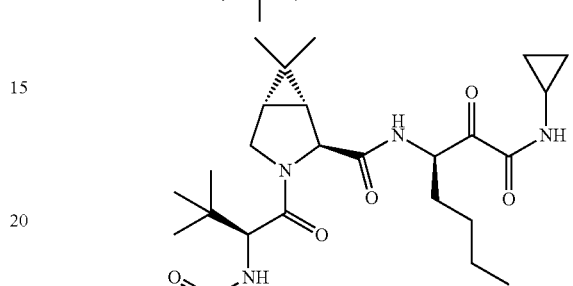
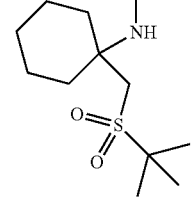
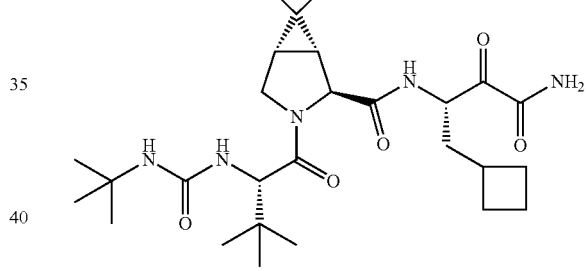
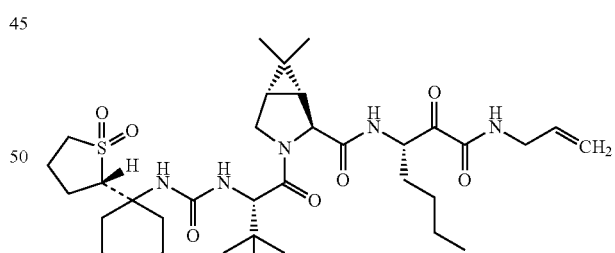
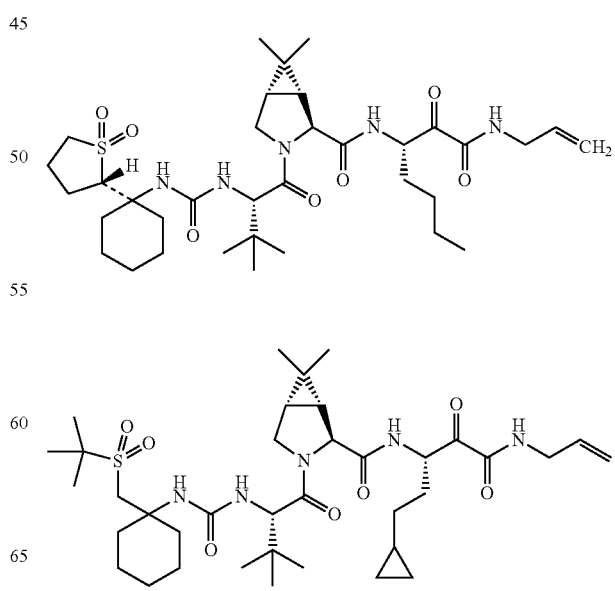

111
-continued
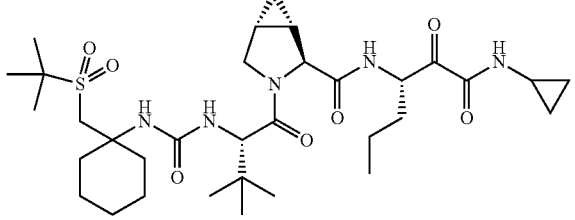
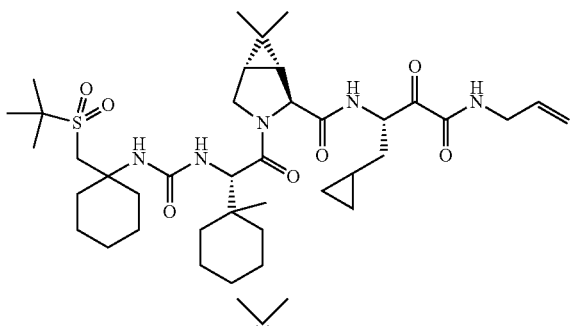
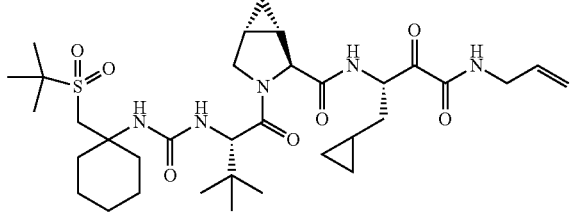
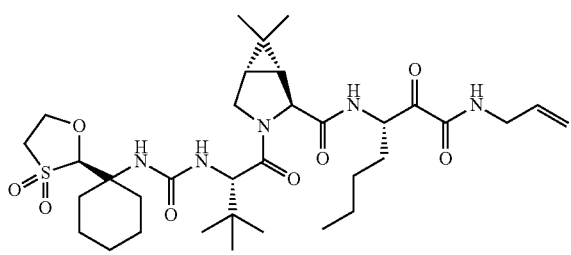
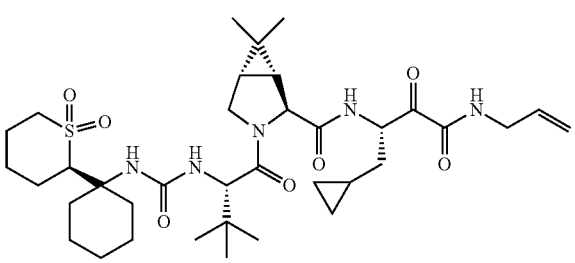
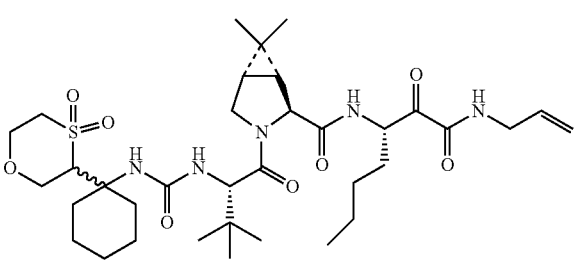
112
-continued
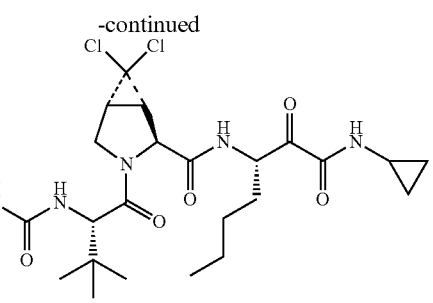
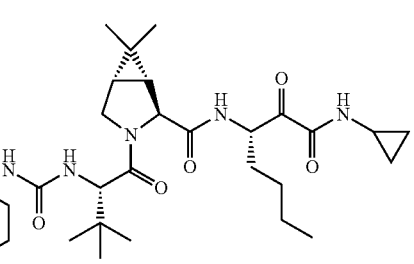
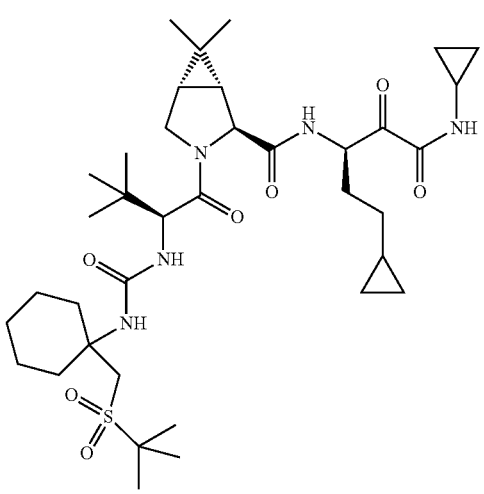
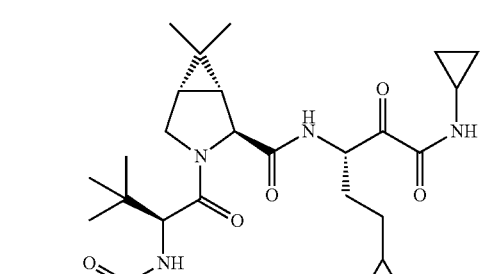
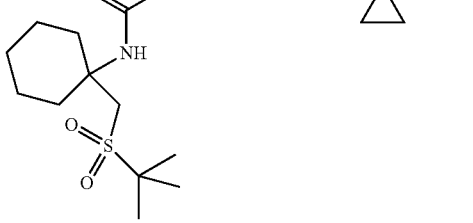

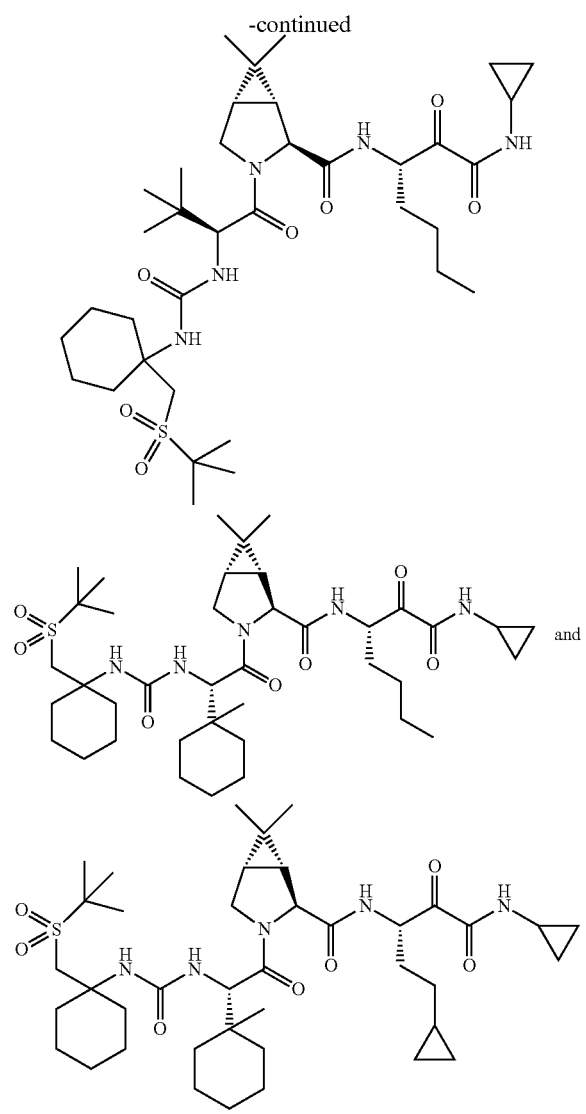

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

Viral entry inhibitors useful as second additional therapeutic agents in the present compositions and methods include, but are not limited to, PRO-206 (Progenics), REP-9C (REPICor), SP-30 (Samaritan Pharmaceuticals) and ITX-5061 (iTherx).

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful as second additional therapeutic agents in the present compositions and methods include, but are not limited to, AZD2836 (Astra Zeneca), ACH-1095 (Achillion) and ACH-806 (Achillion).

HCV NS5A inhibitors useful in the present compositions and methods include, but are not limited to, A-832 (Arrow Therapeutics), PPI-461 (Presidio), PPI-1301 (Presidio) and BMS-790052 (Bristol-Myers Squibb).

HCV replicase inhibitors useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis), MBL-HCV 1 (MassBiologics), GI-5005 (GlobeImmune), CT-011 (CureTech/Teva) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO 206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Remark); Debio 025 (Debiophaml); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Tetracyclic Xanthene Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one Tetracyclic Xanthene Derivative(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3MIU (12 mcg)/0.5 mL/TIW for 24 weeks or 48 weeks for first time treatment.

In another embodiment, when the additional therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/I mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an interferon, a pegylated interferon and ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and ribavirin.

In one embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

Compositions and Administration

Due to their activity, the Tetracyclic Xanthene Derivatives are useful in veterinary and human medicine. As described above, the Tetracyclic Xanthene Derivatives are useful for treating or preventing HCV infection in a patient in need thereof.

When administered to a patient, the Tetracyclic Xanthene Derivatives can be administered as a component of a composition that comprises a pharmaceutically acceptable carrier or vehicle. The present invention provides pharmaceutical compositions comprising an effective amount of at least one Tetracyclic Xanthene Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Tetracyclic Xanthene Derivatives are administered orally.

In another embodiment, the one or more Tetracyclic Xanthene Derivatives are administered intravenously.

In one embodiment, a pharmaceutical preparation comprising at least one Tetracyclic Xanthene Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Tetracyclic Xanthene Derivative(s) by weight or volume. In various embodiments, the present compositions can contain, in one embodiment, from about 1% to about 70% or from about 5% to about 60% of the Tetracyclic Xanthene Derivative(s) by weight or volume.

The quantity of Tetracyclic Xanthene Derivative in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Tetracyclic Xanthene Derivatives will be regulated according to the judgment of the attending clinician considering such factors as age, condition and size of the patient as well as severity of the symptoms being treated. Generally, a total daily dosage of the Tetracyclic Xanthene Derivatives range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Tetracyclic Xanthene Derivative or a pharmaceutically acceptable salt thereof; (ii) one or more additional therapeutic agents that are not a Tetracyclic Xanthene Derivative; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and to additional therapeutic agents, each of which are independently selected from the group consisting of HCV antiviral agents, immunomodulators, and anti-infective agents.

Kits

In one aspect, the present invention provides a kit comprising a therapeutically effective amount of at least one Tetracyclic Xanthene Derivative, or a pharmaceutically acceptable salt, solvate, ester or prodrug of said compound and a pharmaceutically acceptable carrier, vehicle or diluent.

In another aspect the present invention provides a kit comprising an amount of at least one Tetracyclic Xanthene Derivative, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Tetracyclic Xanthene Derivatives and the one or more additional therapeutic agents are provided in the same container. In one embodiment, the one or more Tetracyclic Xanthene Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

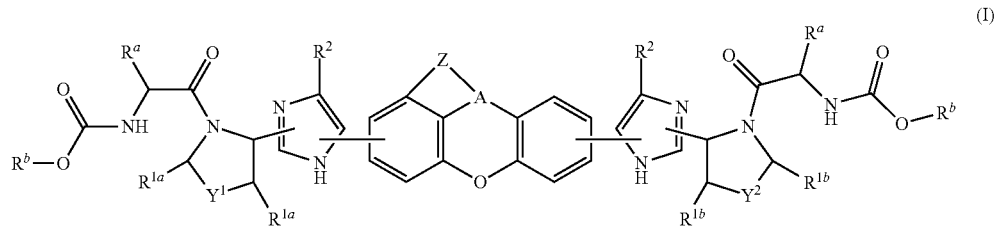

or a pharmaceutically acceptable salt thereof,
wherein:
A is N or CH;
each of $Y^1$ and $Y^2$ is independently —[C($R^1$)$_2$]$_w$— or —Si($R^b$)$_2$;
Z is —C($R^a$)=C($R^a$)—, —[C($R^a$)$_3$]$_t$—, —O—C($R^a$)=, —N($R^a$)—C($R^a$)=, —C($R^a$)=N—, —O—[C($R^a$)$_2$]$_w$— or —N($R^a$)—C($R^a$)$_2$—C($R^a$)$_2$—, such that when Z is —O—C($R^a$)= or —N($R^a$)—C($R^a$)=, then A is carbon;
each occurrence of $R^a$ is independently H, $C_1$-$C_6$ alkyl, $C_3$-$C_7$ cycloalkyl, $C_6$-$C_{10}$ aryl, 4- to 7-membered heterocycloalkyl or 5- to 6-membered heteroaryl;
each occurrence of $R^b$ is independently $C_1$-$C_6$ alkyl, $C_3$-$C_7$ cycloalkyl, 4- to 7-membered heterocycloalkyl or 5- to 6-membered heteroaryl;
each occurrence of $R^1$ is independently H, $C_1$-$C_6$ alkyl, halo, $C_1$-$C_6$ haloalkyl, —O—$C_1$-$C_6$ alkyl or —CN, or two $R^1$ groups that are attached to the same carbon atom, together with the common carbon atom to which they are attached, can join to form a spirocyclic $C_3$-$C_6$ cycloalkyl group or a spirocyclic 4- to 7-membered heterocycloalkyl group;
each occurrence of $R^{1a}$ is independently H, $C_1$-$C_6$ alkyl, CN, halo, $C_1$-$C_6$ haloalkyl, —OH, —O—($C_1$-$C_6$ alkyl), —O—($C_1$-$C_6$ haloalkyl), or two $R^{1a}$ groups, together with the carbon atoms to which they are attached, join to form a $C_3$-$C_6$ cycloalkyl group or a 4- to 7-membered heterocycloalkyl group, or when $Y^1$ is carbon, one $R^{1a}$ group and $Y^1$, together with the carbon atoms to which they are attached, join to form a $C_3$-$C_6$ cycloalkyl group or a 4- to 7-membered heterocycloalkyl group;
each occurrence of $R^{1b}$ is independently H, $C_1$-$C_6$ alkyl, CN, halo, $C_1$-$C_6$ haloalkyl, —OH, —O—($C_1$-$C_6$ alkyl), —O—($C_1$-$C_6$ haloalkyl), or two $R^{1b}$ groups, together with the carbon atoms to which they are attached, join to form a $C_3$-$C_6$ cycloalkyl group or a 4- to 7-membered heterocycloalkyl group, or when $Y^2$ is carbon, one $R^{1b}$ group and $Y^2$, together with the carbon atoms to which they are attached, join to form a $C_3$-$C_6$ cycloalkyl group or a 4- to 7-membered heterocycloalkyl group;
each occurrence of $R^2$ is independently H, halo, or alkyl;
t is 1, 2 or 3; and
each occurrence of w is independently 1 or 2.

2. The compound of claim 1 having the formula:

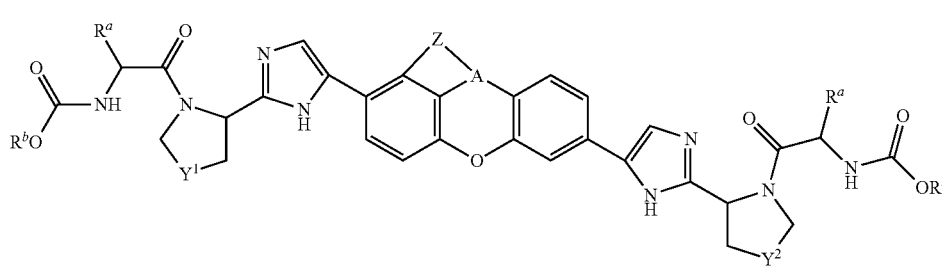

or a pharmaceutically acceptable salt thereof,
wherein:
A is N or CH;
each of $Y^1$ and $Y^2$ is independently —CH$_2$—, —CF$_2$— or —CHF—;
Z is —OCH$_2$—, —OCH$_2$CH$_2$—, —O—CH=, —CH$_2$CH$_2$—, —CH$_2$CH$_2$CH$_2$—, —CH=CH— or —CH=N—, such that when Z is —O—CH=, then A is carbon;
each occurrence of $R^a$ is independently $C_1$-$C_6$ alkyl, $C_6$-$C_{10}$ aryl or $C_3$-$C_7$ cycloalkyl; and
each occurrence of $R^b$ is independently $C_1$-$C_6$ alkyl.

3. The compound of claim 1 having the formula:

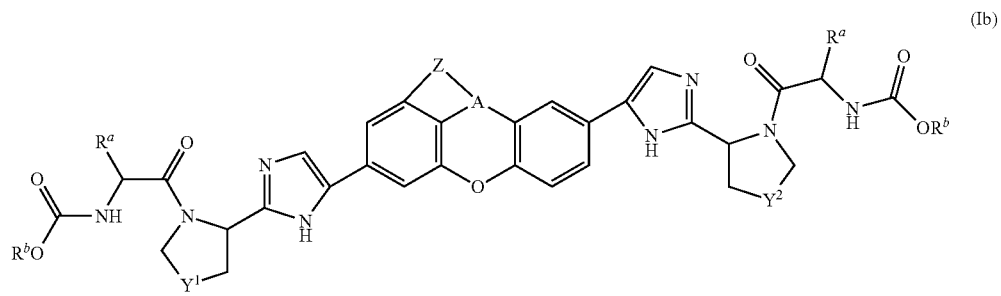

or a pharmaceutically acceptable salt thereof,
wherein:
  A is N or CH;
  each of $Y^1$ and $Y^2$ is independently —$CH_2$—, —$CF_2$— or —CHF—;
  Z is —$OCH_2$—, —$OCH_2CH_2$—, —$CH_2CH_2$—, —$CH_2CH_2CH_2$—, —CH═CH— or —CH═N such that when Z is —O—CH═, then A is carbon;
  each occurrence of $R^a$ is independently $C_1$-$C_6$ alkyl, $C_6$-$C_{10}$ aryl or $C_3$-$C_7$ cycloalkyl; and
  each occurrence of $R^b$ is independently $C_1$-$C_6$ alkyl.

4. The compound of claim 1, wherein A is N and Z is —CH═CH—, —$CH_2$—$CH_2$— or —$CH_2$—$CH_2$—$CH_2$—.

5. The compound of claim 4, wherein $Y^1$ and $Y^2$ are each independently selected from —$CH_2$—, —$CF_2$— and —CHF—.

6. The compound of claim 5, wherein each occurrence of $R^a$ is $C_1$-$C_6$ alkyl or $C_3$-$C_7$ cycloalkyl; and each occurrence of $R^b$ is $C_1$-$C_6$ alkyl.

7. The compound of claim 6, wherein each occurrence of $R^a$ is independently isopropyl, t-butyl or cyclopropyl.

8. The compound of claim 7, wherein each occurrence of $R^a$ is isopropyl.

9. The compound of claim 8, wherein each occurrence of $R^b$ is methyl.

10. The compound of claim 9, wherein each occurrence of $R^{1a}$, $R^{1b}$ and $R^2$ is H.

11. The compound of claim 1 having the structure:

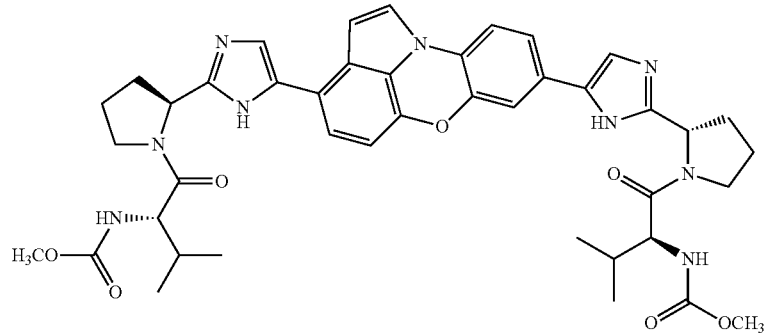

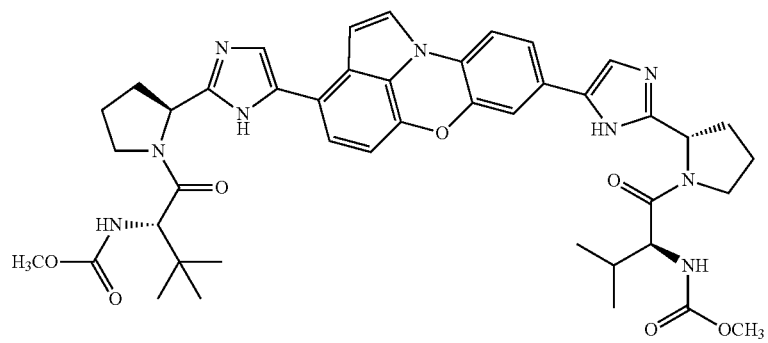

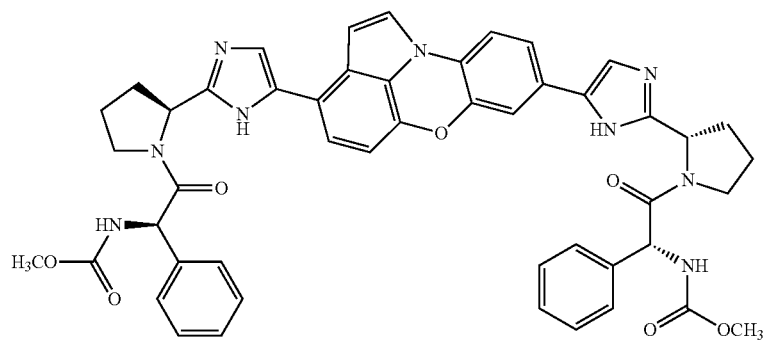
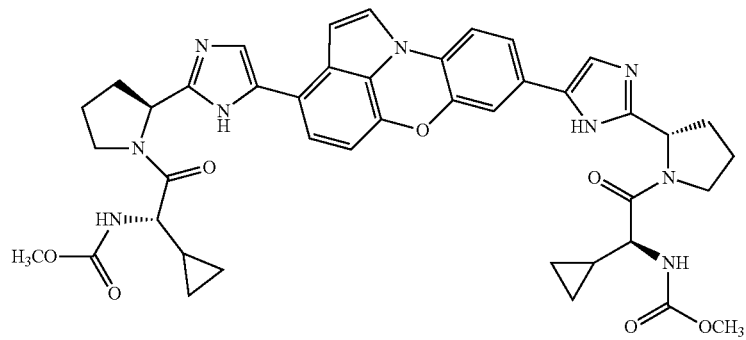
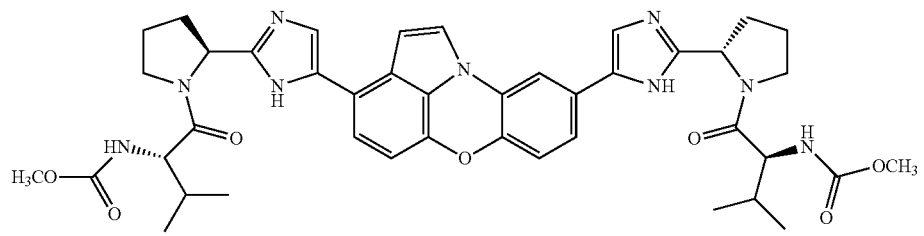
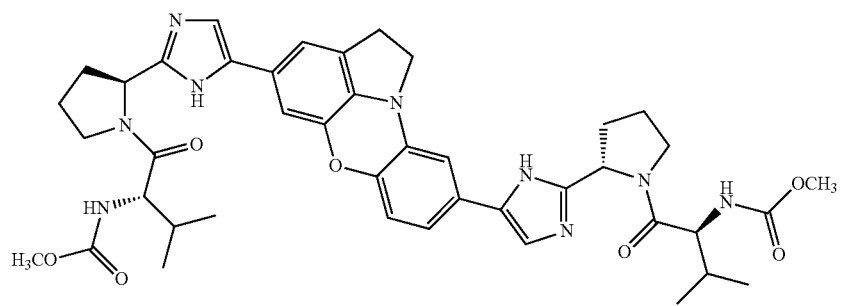
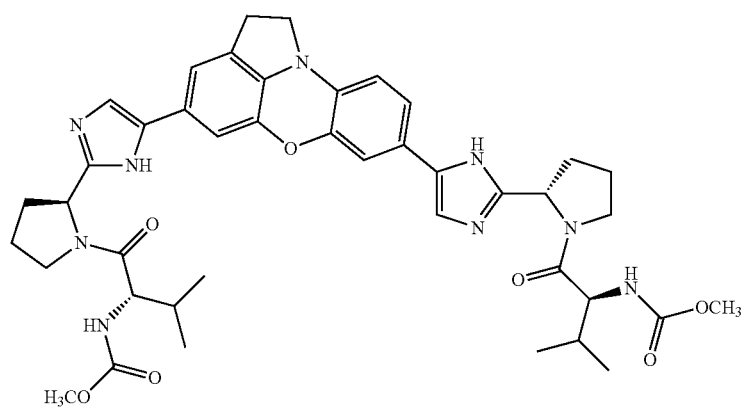

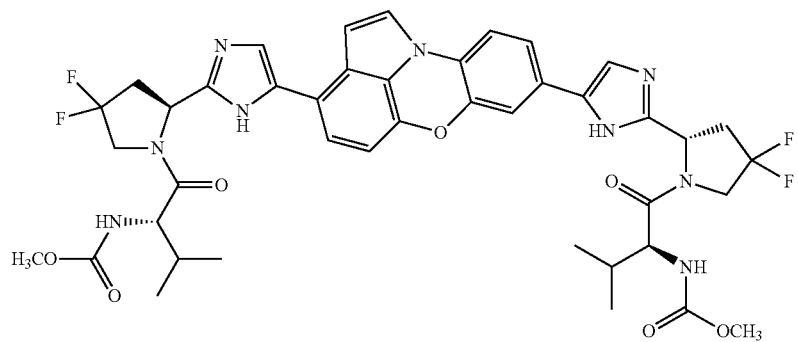
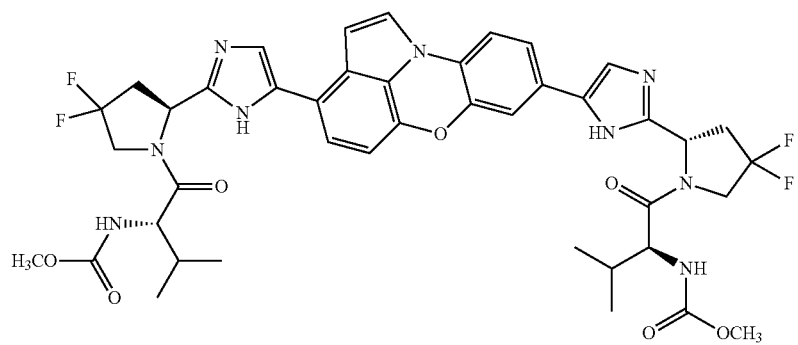
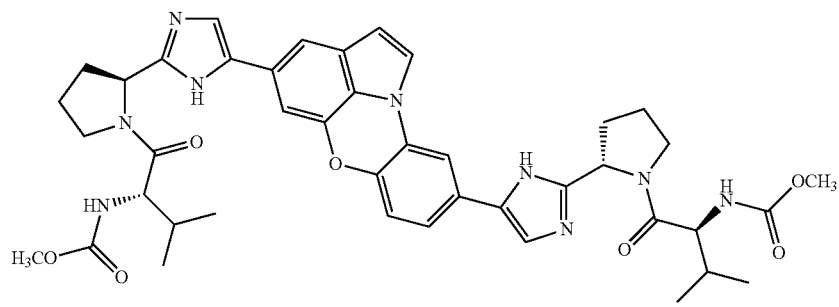
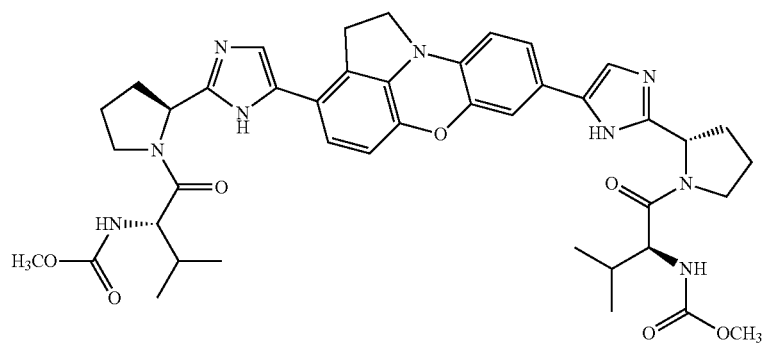
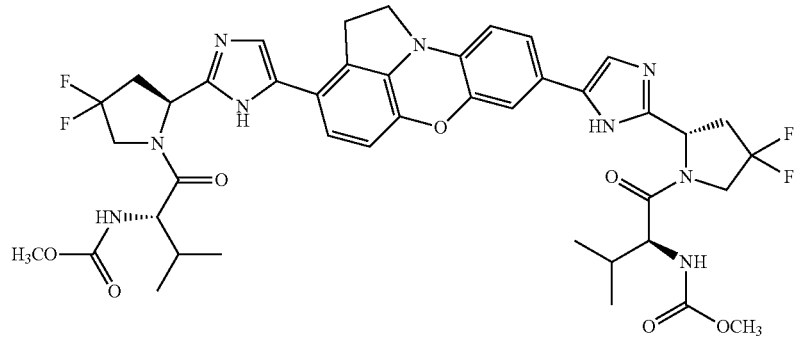

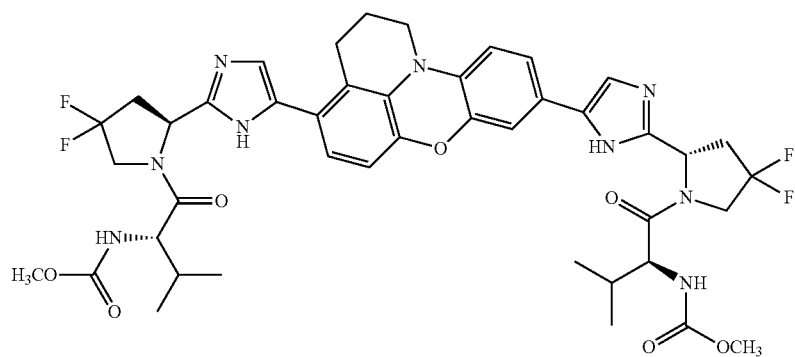
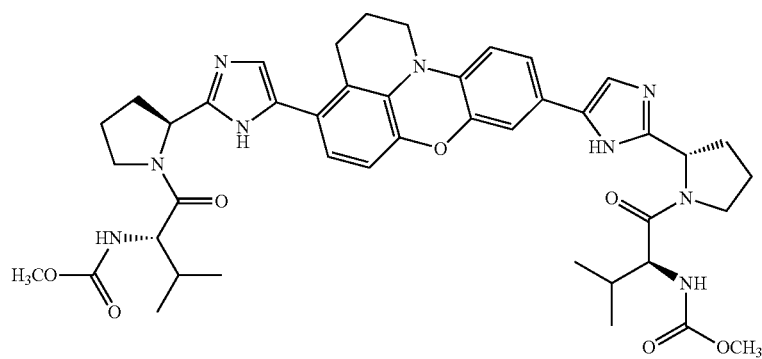
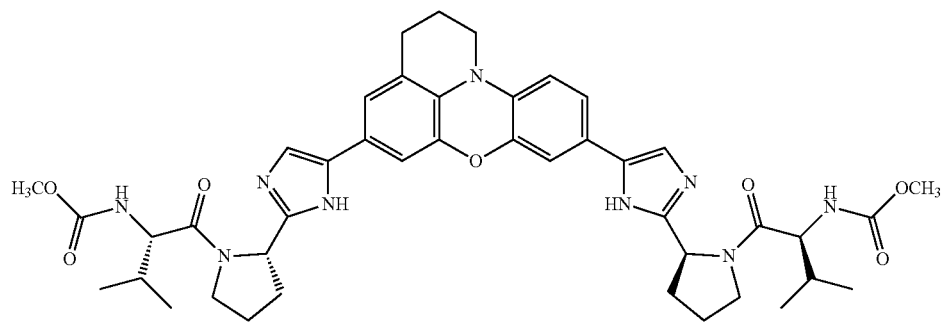
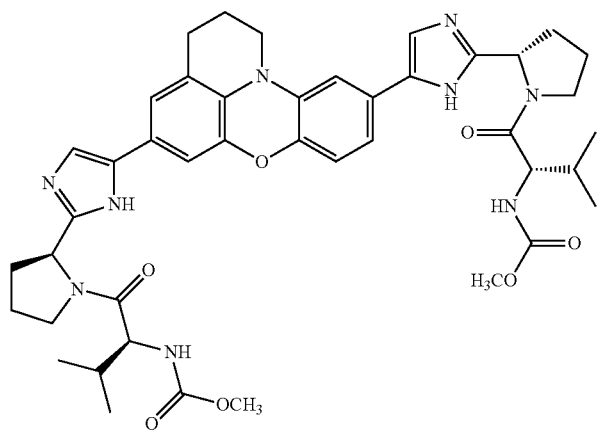

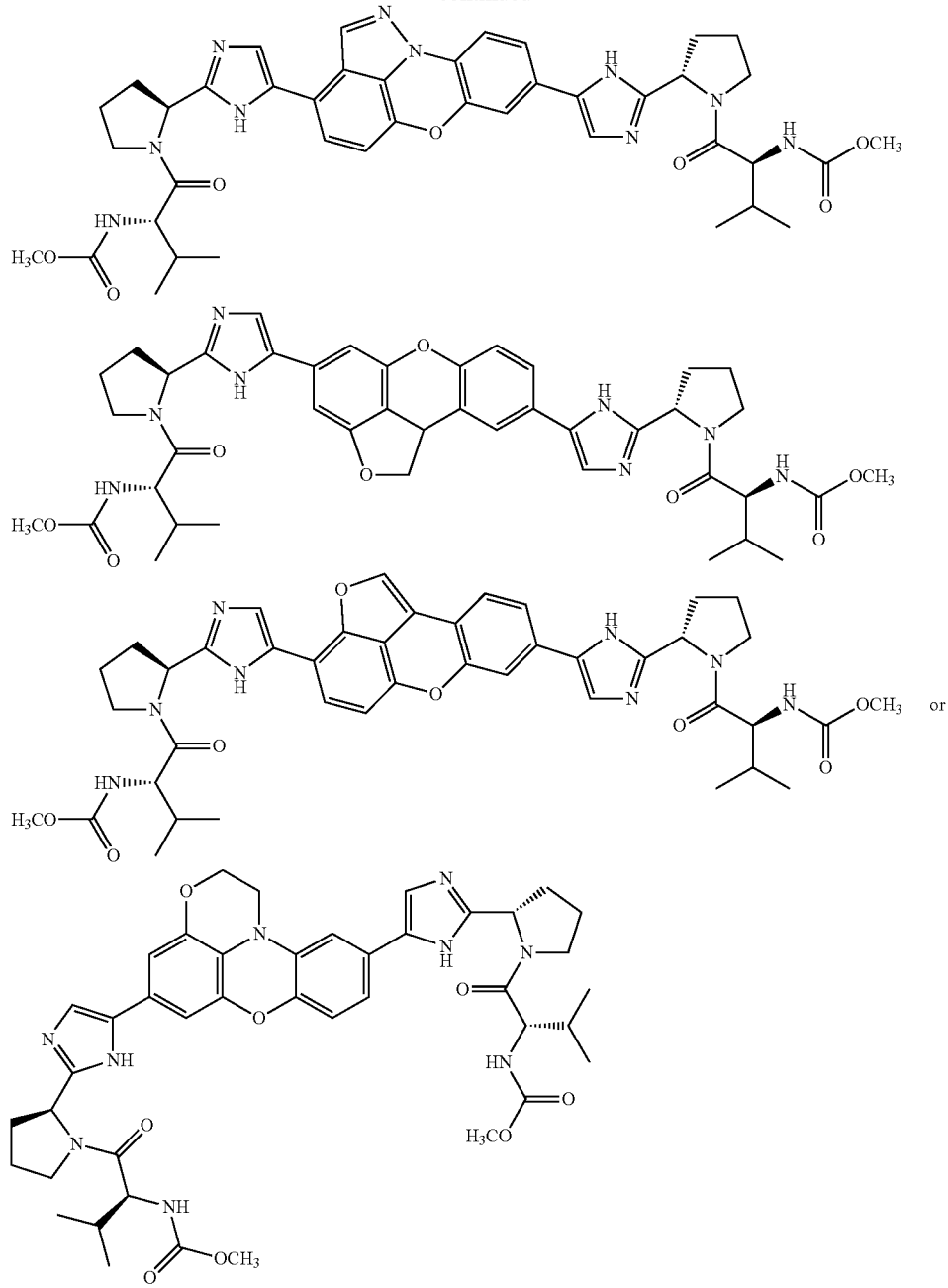

or a pharmaceutically acceptable salt thereof.

12. A method of treating a patient infected with HCV comprising the step of administering an amount of the compound according to claim 1, or a pharmaceutically acceptable salt thereof, effective to treat infection by HCV in said patient.

13. The method according to claim 12, further comprising the step of administering an HCV protease inhibitor to said patient.

14. The method according to claim 12, further comprising the step of administering an HCV polymerase inhibitor to said patient.

* * * * *

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: 5B.2F Primer

<400> SEQUENCE: 1
atggacaggc gccctga                                                 17

<210> SEQ ID NO 2
<211> LENGTH: 20
<212> TYPE: DNA
<213> ORGANISM: Artificial Sequence
<220> FEATURE:
<223> OTHER INFORMATION: 5B.2R Primer

<400> SEQUENCE: 2
ttgatgggca gcttggtttc                                              20

<210> SEQ ID NO 3
<211> LENGTH: 17
<212> TYPE: DNA
<213> ORGANISM: Artificial Sequence
<220> FEATURE:
<223> OTHER INFORMATION: FAM labeled probe

<400> SEQUENCE: 3
cacgccatgc gctgcgg                                                 17
```